(12) United States Patent
Or et al.

(10) Patent No.: US 10,080,743 B2
(45) Date of Patent: Sep. 25, 2018

(54) ISOXAZOLE DERIVATIVES AS FXR AGONISTS AND METHODS OF USE THEREOF

(71) Applicant: Enanta Pharmaceuticals, Inc., Watertown, MA (US)

(72) Inventors: Yat Sun Or, Watertown, MA (US); Bin Wang, Brighton, MA (US); Xuechao Xing, Wilmington, MA (US); Ruichao Shen, West Roxbury, MA (US); Brett Granger, Sudbury, MA (US); Jun Ma, Belmont, MA (US); Jing He, Somerville, MA (US); Yong He, Lexington, MA (US); Jiang Long, Wayland, MA (US); Guoqiang Wang, Belmont, MA (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 0 days.

(21) Appl. No.: 15/497,359

(22) Filed: Apr. 26, 2017

(65) Prior Publication Data

US 2017/0304272 A1    Oct. 26, 2017

Related U.S. Application Data

(60) Provisional application No. 62/327,914, filed on Apr. 26, 2016.

(51) Int. Cl.
| | | |
|---|---|---|
| *C07D 261/08* | (2006.01) | |
| *C07D 413/12* | (2006.01) | |
| *A61K 31/42* | (2006.01) | |
| *A61K 31/422* | (2006.01) | |

(52) U.S. Cl.
CPC .......... *A61K 31/42* (2013.01); *A61K 31/422* (2013.01); *C07D 261/08* (2013.01); *C07D 413/12* (2013.01)

(58) Field of Classification Search
CPC .................. C07D 261/08; C07D 413/12
See application file for complete search history.

(56) References Cited

U.S. PATENT DOCUMENTS

| | | |
|---|---|---|
| 5,571,809 A | 11/1996 | Hargrave et al. |
| 6,974,830 B2 | 12/2005 | Bauer et al. |
| 7,319,109 B2 | 1/2008 | Boggs et al. |
| 7,846,960 B2 | 12/2010 | Bell et al. |
| 7,863,302 B2 | 1/2011 | Bell et al. |
| 7,897,773 B2 | 3/2011 | Aletru et al. |
| 7,902,373 B2 | 3/2011 | Blake et al. |
| 8,952,042 B2 | 2/2015 | Kremoser et al. |
| 9,751,874 B2 | 9/2017 | Gege et al. |
| 2004/0048316 A1 | 3/2004 | Haffner et al. |
| 2007/0054902 A1 | 3/2007 | Fukui et al. |
| 2008/0167356 A1 | 7/2008 | Caldwell et al. |
| 2009/0163474 A1 | 6/2009 | Zhang et al. |
| 2010/0015063 A1 | 1/2010 | Carter et al. |
| 2010/0063697 A1 | 3/2010 | Lindgren et al. |
| 2010/0099703 A1 | 4/2010 | Garcia-Lopez et al. |
| 2010/0120775 A1 | 5/2010 | Bass, III et al. |
| 2010/0152166 A1 | 6/2010 | Genin et al. |
| 2010/0184809 A1 | 7/2010 | Kremoser et al. |
| 2010/0210660 A1 | 8/2010 | Kremoser et al. |
| 2010/0249179 A1 | 9/2010 | Deaton et al. |
| 2010/0292212 A1 | 11/2010 | Ackermann et al. |
| 2011/0034507 A1 | 2/2011 | Akwabi-Ameyaw et al. |
| 2011/0275595 A1 | 11/2011 | Eckhardt et al. |
| 2012/0004164 A1 | 1/2012 | Dales et al. |
| 2013/0261108 A1 | 10/2013 | Tully et al. |
| 2014/0038947 A1 | 2/2014 | Glick et al. |
| 2014/0221659 A1 | 8/2014 | Kinzel et al. |
| 2015/0299210 A1 | 10/2015 | Bailey et al. |
| 2015/0366856 A1 | 12/2015 | Tully et al. |
| 2016/0130297 A1 | 5/2016 | Or et al. |
| 2017/0298068 A1 | 10/2017 | Gege et al. |
| 2017/0333399 A1 | 11/2017 | Or et al. |
| 2017/0334893 A1 | 11/2017 | Or et al. |
| 2017/0334894 A1 | 11/2017 | Or et al. |
| 2017/0368038 A1 | 12/2017 | Badman et al. |

(Continued)

FOREIGN PATENT DOCUMENTS

| | | |
|---|---|---|
| WO | 2004046162 A2 | 6/2004 |
| WO | 2009149795 A2 | 12/2009 |

(Continued)

OTHER PUBLICATIONS

U.S. Appl. No. 15/497,268, filed Apr. 26, 2017.

(Continued)

*Primary Examiner* — Laura L Stockton

(74) *Attorney, Agent, or Firm* — Elmore Patent Law Group PC; Edgar Harlan; Carolyn Elmore

(57) ABSTRACT

The present invention provides compounds of Formula I,

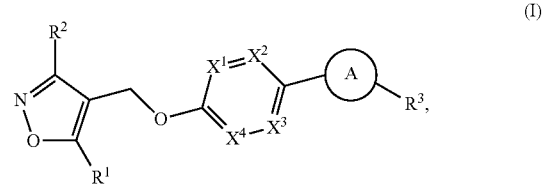

(I)

pharmaceutical compositions comprising these compounds and methods of using these compounds to treat or prevent a disease or disorder mediated as FXR modulators. Specifically, the present invention relates to isoxazole derivatives useful as agonists for FXR, and methods for their preparation and use.

22 Claims, No Drawings

(56) References Cited

U.S. PATENT DOCUMENTS

| | | |
|---|---|---|
| 2018/0030003 A1 | 2/2018 | Wang et al. |
| 2018/0099957 A1 | 4/2018 | Ma et al. |

FOREIGN PATENT DOCUMENTS

| | | |
|---|---|---|
| WO | 2011020615 A1 | 2/2011 |
| WO | 2011021645 A1 | 2/2011 |
| WO | 2012087519 A1 | 6/2012 |
| WO | 2012087520 A1 | 6/2012 |
| WO | 2012087521 A1 | 6/2012 |
| WO | 2013007387 A1 | 1/2013 |
| WO | 2013037482 A1 | 3/2013 |
| WO | 2013166176 A1 | 11/2013 |
| WO | 2015036442 A1 | 3/2015 |
| WO | 2017118294 A1 | 7/2017 |
| WO | 2017128896 A1 | 8/2017 |
| WO | 2017133521 | 8/2017 |
| WO | 2017145041 | 8/2017 |

OTHER PUBLICATIONS

U.S. Appl. No. 15/497,307, filed Apr. 26, 2017.
U.S. Appl. No. 15/597,431, filed May 17, 2017.
U.S. Appl. No. 15/597,417, filed May 17, 2017.
U.S. Appl. No. 15/597,423, filed May 17, 2017.
Crawley, "Farnesoid X Receptor Modulators: a patent review," Expert Opinion on Therapeutic Patents, 20(8): 1047-1057, 2010.
Sepe, et al., "Farnesoid X receptor modulators (2011-2014): a patent review," Expert Opinion on Therapeutic Patents, 25:8, 885-896, 2015.
Buijsman, et al., "Non-Steroidal Steroid Receptor Modulators," Current Medicinal Chemistry, 12:1017-1075, 2005.
U.S. Appl. No. 15/793,554, filed Oct. 25, 2017.
Ali, et al., "Recent advances in the development of farnesoid X receptor agonists," Ann Transl Med, 3(1):5, pp. 1-16, 2015.

ISOXAZOLE DERIVATIVES AS FXR AGONISTS AND METHODS OF USE THEREOF

RELATED APPLICATIONS

This application claims the benefit of U.S. Provisional Application No. 62/327,914, filed on Apr. 26, 2016. The entire teachings of the above applications are incorporated herein by reference.

TECHNICAL FIELD

The present invention relates generally to compounds and pharmaceutical compositions useful as FXR modulators. Specifically, the present invention relates to isoxazole derivatives useful as agonists for FXR, and methods for their preparation and use.

BACKGROUND OF THE INVENTION

Farnesoid X Receptor (FXR, NR1H4) is a member of the nuclear receptor family of ligand-activated transcription factors that includes receptors for the steroid, retinoid, and thyroid hormones (D. J. Mangelsdorf, et al., *Cell*, 1995, 83(6), 841-850). FXR was originally identified from a rat liver cDNA library. Farnesol and derivatives, collectively termed farnesoids, activate the rat ortholog at high concentration, but they do not modulate the human or mouse receptors. FXR is primarily expressed in the liver, kidney, and intestine (W. Seol, et al., *Mol. Endocrinol.*, 1995, 9(1), 72-85; B. M. Forman, et al., *Cell*, 1995, 81(5), 687-693). The relevant physiological ligands of FXR include the primary bile acids cholic acid (CA) and chenodeoxycholic acid (CDCA) and the secondary bile acids deoxycholic acid (DCA) and lithocholic acid (LCA) (D. Parks, et al., *Science*, 1999, 284(5418), 1362-1365). The most potent physiological ligand for FXR is CDCA, which plays a key role in regulating the expression of several genes that participate in bile acid homeostasis. FXR functions as a heterodimer with the retinoid X receptor (RXR) and binds to response elements in the promoter region of target genes to regulate gene transcription. FXR seems to be also involved in paracrine and endocrine signaling by upregulating the expression of the cytokine Fibroblast Growth Factor (J. Holt, et al., *Genes Dev.*, 2003, 17(13), 1581-1591; T. Inagaki, et al., *Cell Metab.*, 2005, 2(4), 217-225).

Small molecule compounds which act as FXR modulators have been disclosed in the following publications: WO 2000/037077, WO 2002/072598, WO 2003/015771, WO 2003/099821, WO 2004/00752, WO 2004/048349, WO 2005/009387, WO 2005/082925, US 2005/0054634, WO 2007/052843, WO 2007/070796, WO 2007/076260, WO 2007/092751, WO 2007/095174, WO 2007/140174, WO 2007/140183, US 2007/0142340, WO 2008/000643, WO 2008/002573, WO 2008/025539, WO 2008/025540, WO 2008/051942, WO 2008/073825, WO 2008/157270, US 2008/0299118, US 2008/0300235, WO 2009/005998, WO 2009/012125, WO 2009/027264, WO 2009/062874, WO 2009/127321, WO 2009/149795, US 2009/0131409, US 2009/0137554, US 2009/0163474, US 2009/0163552, US 2009/0215748, WO 2010/043513, WO 2011/020615, WO 2011/117163, WO 2012/087519, WO 2012/087520, WO 2012/087521, WO 2013/007387, WO 2013/037482, WO 2013/166176, WO 2013/192097, WO 2014/184271, US 2014/0186438, US 2014/0187633, and WO 2015/017813. Further small molecule FXR modulators have been recently reviewed (R. C. Buijsman, et al., *Curr. Med. Chem.* 2005, 12(9), 1017-1075; Crawley, M. L. *Expert Opin. Ther. Patents* 2010, 20(8), 1047-1057; V. Sepe, et al., *Expert Opin. Ther. Patents* 2015, 25(8), 885-896 Y. Xu, *J. Med. Chem.* 2016, DOI: 10.1021/acs.jmedchem.5b00342).

There is a need for the development of FXR modulators for the treatment and prevention of disease.

SUMMARY OF THE INVENTION

In one aspect, the invention provides compounds represented by Formula I, or a pharmaceutically acceptable salt thereof:

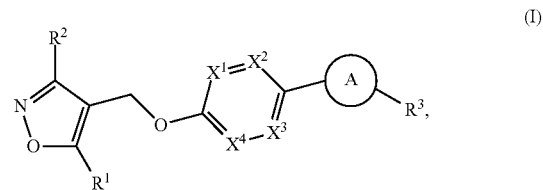
(I)

wherein $R^1$ is hydrogen, halogen, cyano, optionally substituted $C_1$-$C_6$ alkyl, optionally substituted $C_2$-$C_6$ alkenyl, optionally substituted $C_2$-$C_6$ alkynyl, optionally substituted $C_3$-$C_6$ cycloalkyl or optionally substituted 3- to 6-membered heterocycloalkyl. Preferably, $R^1$ is isopropyl, tert-butyl, and cyclopropyl;

$R^2$ is an optionally substituted aryl, optionally substituted heteroaryl, optionally substituted arylalkyl or optionally substituted heteroarylalkyl;

$X^1$, $X^2$, $X^3$, and $X^4$ are independently selected from N or C(Y); wherein Y is selected from hydrogen, halo, cyano, $C_1$-$C_6$ alkyl, $C_2$-$C_6$ alkenyl, $C_2$-$C_6$ alkynyl, $C_3$-$C_6$ cycloalkyl, heterocycloalkyl, haloalkyl, alkoxy, or haloalkoxy; preferably no more than 1, 2 or 3 of $X^1$, $X^2$, $X^3$, and $X^4$ are N;

is aryl, heterocyclic, heteroaryl, bicyclic fused arylheterocyclic or bicyclic fused heteroarylheterocyclic, wherein said aryl, heterocyclic, heteroaryl, bicyclic fused arylheterocyclic or bicyclic fused heteroarylheterocyclic is optionally substituted with one or two substituents independently selected from optionally substituted —$C_1$-$C_8$ alkyl, halo, and halo-$C_1$-$C_8$-alkyl; preferably

is a bicyclic fused aryl, bicyclic fused heteroaryl or bicyclic fused heteroaryl heterocyclic;

$R^3$ is

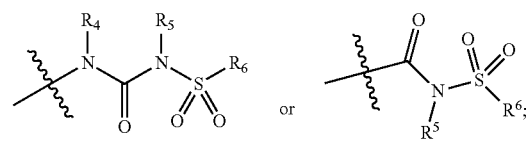

$R^4$ and $R^5$ are independently selected from the group consisting of:
1) Hydrogen;
2) Optionally substituted —$C_1$-$C_8$ alkyl;
3) Optionally substituted —$C_2$-$C_8$ alkenyl;
4) Optionally substituted —$C_2$-$C_8$ alkynyl; and
5) Optionally substituted —$C_3$-$C_8$ cycloalkyl;

$R^6$ is selected from the group consisting of:
1) Optionally substituted —$C_1$-$C_8$ alkyl
2) Optionally substituted —$C_2$-$C_8$ alkenyl;
3) Optionally substituted —$C_2$-$C_8$ alkynyl;
4) Optionally substituted —$C_3$-$C_8$ cycloalkyl;
5) Optionally substituted aryl;
6) Optionally substituted arylalkyl;
7) Optionally substituted 3- to 8-membered heterocycloalkyl;
8) Optionally substituted heteroaryl;
9) Optionally substituted heteroaryl alkyl; and
10) $NR^7R^8$; wherein $R^7$ and $R^8$ are each independently selected from hydrogen, optionally substituted —$C_1$-$C_8$ alkyl, optionally substituted —$C_2$-$C_8$ alkenyl, optionally substituted —$C_2$-$C_8$ alkynyl, optionally substituted —$C_3$-$C_8$ cycloalkyl, optionally substituted aryl, optionally substituted arylalkyl, optionally substituted 3- to 8-membered heterocycloalkyl, optionally substituted heteroaryl, optionally substituted heteroarylalkyl, or $R^7$ and $R^8$ are taken together with the nitrogen atom to which they are attached to form an optionally substituted heterocyclic ring.

In another embodiment, the present invention provides a pharmaceutical composition comprising a therapeutically effective amount of a compound or combination of compounds of the present invention, or a pharmaceutically acceptable salt form, stereoisomer, solvate, hydrate or combination thereof, in combination with a pharmaceutically acceptable carrier or excipient.

In another embodiment, the present invention provides a method for the prevention or treatment of an FXR mediated disease or condition. The method comprises administering a therapeutically effective amount of a compound of Formula (I). The present invention also provides the use of a compound of Formula (I) for the preparation of a medicament for the prevention or treatment of an FXR mediated disease or condition.

DETAILED DESCRIPTION OF THE INVENTION

A first embodiment of the invention is a compound represented by Formula I as described above, or a pharmaceutically acceptable salt, ester, stereoisomer, tautomer, solvate, hydrate or combination thereof.

In certain embodiments, the present invention relates to compounds of Formula (I), or a pharmaceutically acceptable salt, ester, stereoisomer, tautomer, solvate, hydrate or combination thereof, wherein $R^1$ is isopropyl, tert-butyl, or cyclopropyl.

In certain embodiments, the present invention relates to compounds of Formula (I), or a pharmaceutically acceptable salt thereof, wherein $R^2$ includes, but is not limited to:

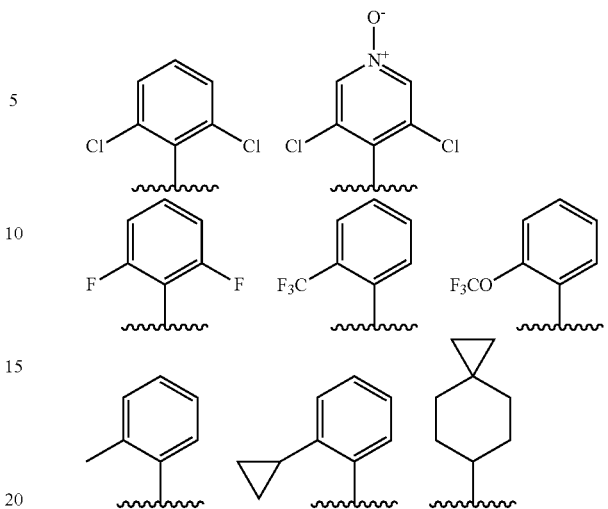

In certain embodiments, the present invention relates to compounds of Formula (I), or a pharmaceutically acceptable salt wherein $R^3$ is

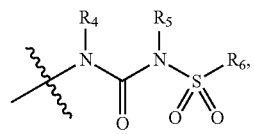

where $R^4$, $R^5$, and $R^6$ are as previously defined. In another embodiment, the present invention relates to compounds of Formula (I), or a pharmaceutically acceptable salt thereof, wherein $R^3$ is

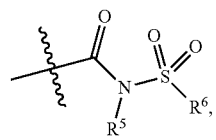

wherein $R^5$ and $R^6$ are as previously defined.

In certain embodiments, the present invention relates to compounds of Formula (I), or a pharmaceutically acceptable salt thereof,

is a group derived from a fused bicyclic aryl or heteroaryl group by removal of two hydrogen atoms. In one embodiment,

is derived from a fused bicyclic aryl or 6/6- or 5/6-fused bicyclic heteroaryl group. Preferably,

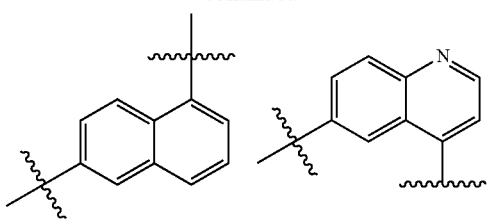

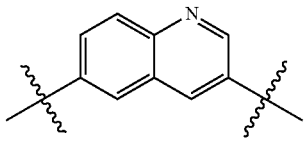

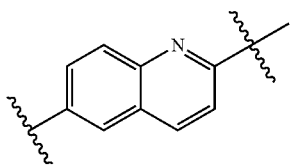

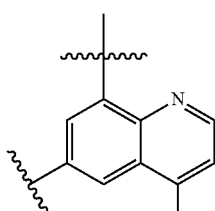

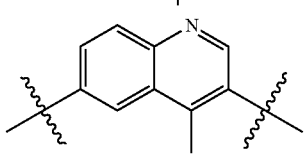

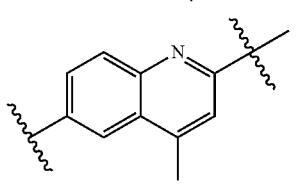

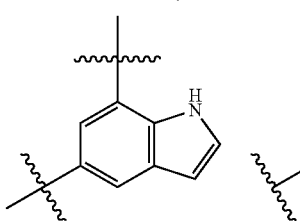

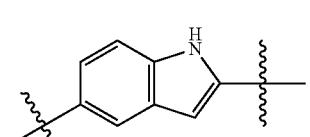

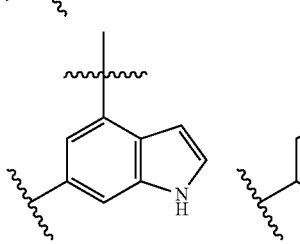

is derived from one of the following by removal of two hydrogen atoms:

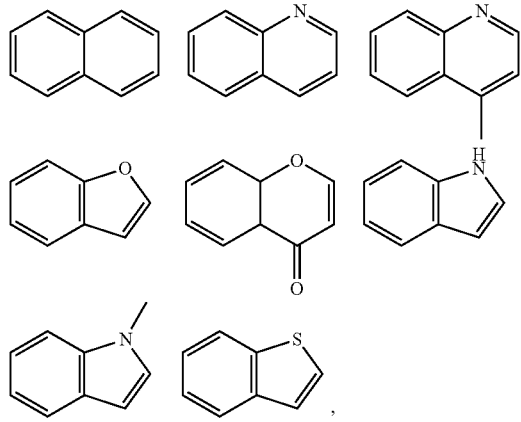

wherein each of the above shown groups is optionally substituted when possible. In embodiments in which

Ⓐ is a fused bicyclic group, the ring comprising $X_1$-$X_4$ and $R_3$ can be connected to atoms of the same ring of

Ⓐ or to atoms of different rings.

In certain embodiments,

Ⓐ is selected from the groups below:

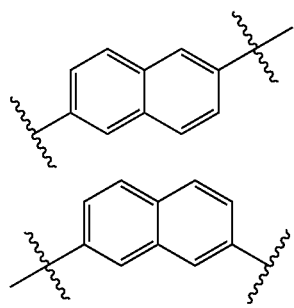

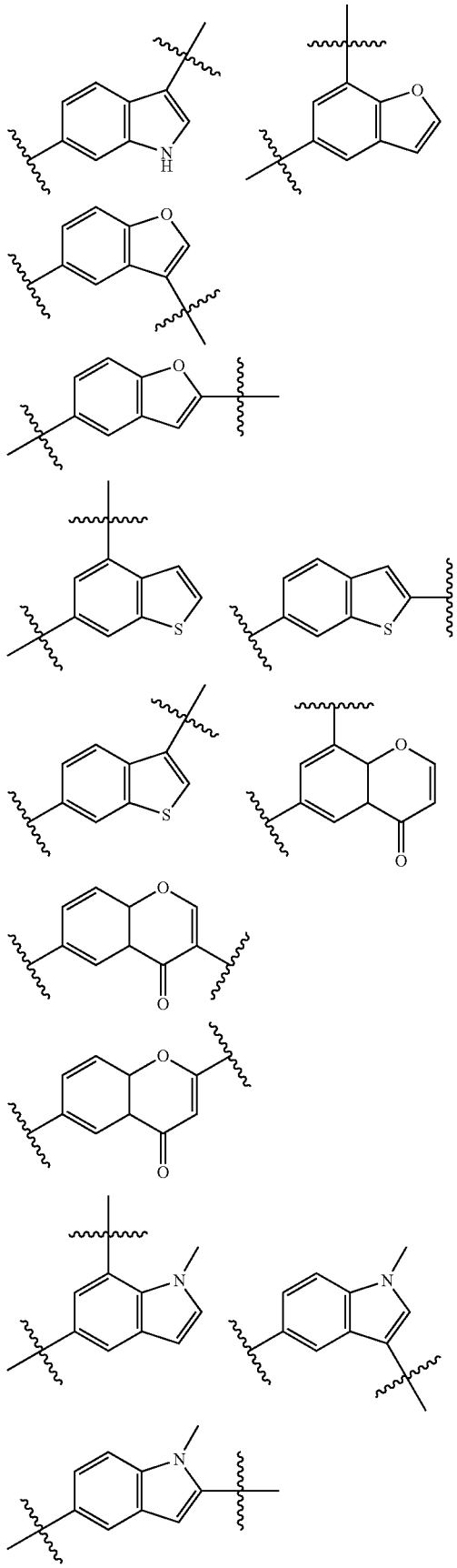

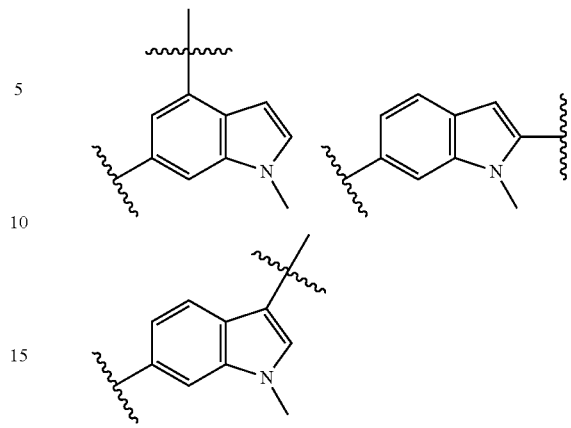

In certain embodiments, the compounds of the invention of the invention are represented by Formula II or III and pharmaceutically acceptable salts thereof:

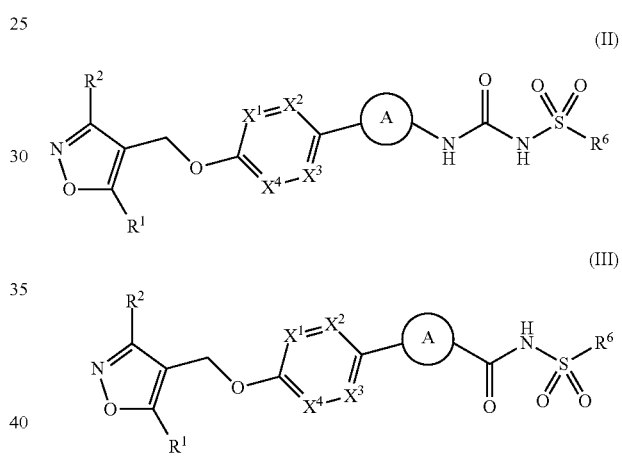

wherein $R^1$, $R^2$, $X^1$, $X^2$, $X^3$, $X^4$,

and $R^6$ are as previously defined.

In certain embodiments, the compounds of the invention are represented by Formula IV or V and pharmaceutically acceptable salts thereof:

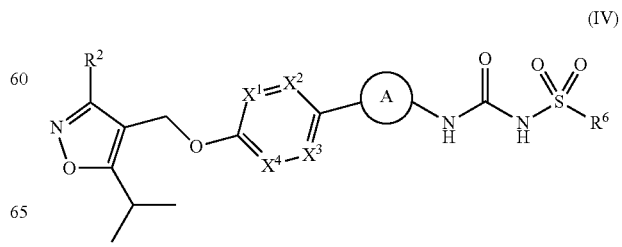

(V)

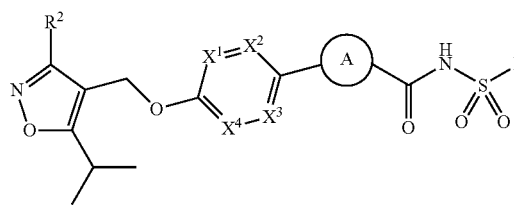

wherein R², X¹, X², X³, X⁴,

and R⁶ are as previously defined.

In certain embodiments, the compounds of the invention are represented by Formula VI or VII and pharmaceutically acceptable salts thereof:

(VI)

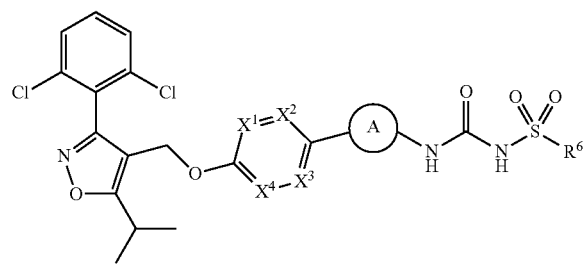

(VII)

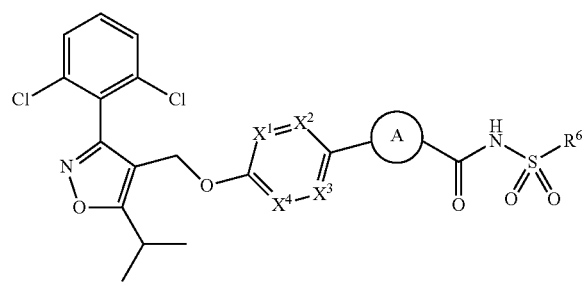

wherein X¹, X², X³, X⁴,

and R⁶ are as previously defined.

In certain embodiments, the compounds of the invention are represented by Formula VIII or IX and pharmaceutically acceptable salts thereof:

(VIII)

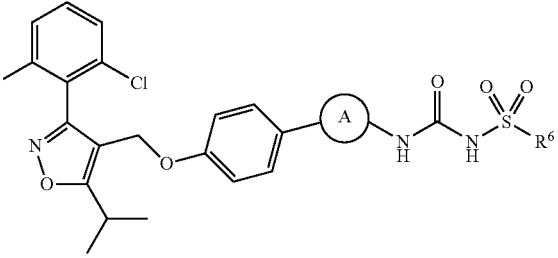

(IX)

wherein, (A)

and R⁶ are as previously defined.

In certain embodiments, the compounds of the invention are represented by Formula X or XI and pharmaceutically acceptable salts thereof:

(X)

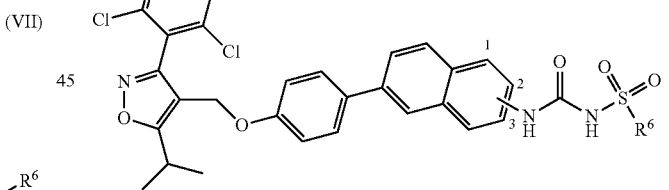

(XI)

wherein R⁶ is as previously defined, and the urea group in Formula (X) or carbonyl group in Formula (XI) is attached to naphthyl at position 1, 2 or 3.

Representative compounds of the invention include, but are not limited to, the following compounds (compound 1 to compound 87 in Table 1) according to Formula X, and pharmaceutically acceptable salts thereof, wherein $R^6$ and the substitution position for the sulfonyl urea are delineated for each compound in Table 1.

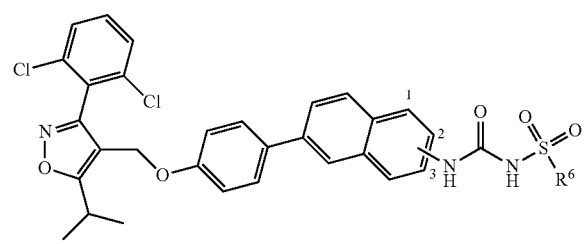

(X)

TABLE 1

| Compound | $R^6$ | Position |
|---|---|---|
| 1 | Methyl | 1 |
| 2 | Ethyl | 1 |
| 3 | Isopropyl | 1 |
| 4 | Butyl | 1 |
| 5 | t-Butyl | 1 |
| 6 | Propyl | 1 |
| 7 | Benzyl | 1 |
| 8 | Vinyl | 1 |
| 9 | Allyl | 1 |
| 10 | —CF$_3$ | 1 |
| 11 | cyclopropyl | 1 |
| 12 | cyclopropyl | 1 |
| 13 | cyclopropylmethyl | 1 |
| 14 | cyclopentyl | 1 |
| 15 | cyclohexyl | 1 |
| 16 | phenyl | 1 |
| 17 | o-tolyl | 1 |
| 18 | p-tolyl | 1 |
| 19 | 4-OCF$_3$-phenyl | 1 |
| 20 | 4-t-butyl-phenyl | 1 |
| 21 | 2-OCF$_3$-phenyl | 1 |
| 22 | 2-F-phenyl | 1 |
| 23 | naphthyl | 1 |
| 24 | —NH$_2$ | 1 |
| 25 | —NHCH$_3$ | 1 |
| 26 | —N(CH$_3$)$_2$ | 1 |
| 27 | pyrrolidinyl | 1 |
| 28 | piperidinyl | 1 |
| 29 | morpholinyl | 1 |
| 30 | Methyl | 2 |
| 31 | Ethyl | 2 |
| 32 | Isopropyl | 2 |
| 33 | Butyl | 2 |
| 34 | t-Butyl | 2 |
| 35 | Propyl | 2 |
| 36 | Benzyl | 2 |
| 37 | Vinyl | 2 |
| 38 | Allyl | 2 |
| 39 | —CF$_3$ | 2 |
| 40 | cyclopropyl | 2 |
| 41 | cyclopropyl | 2 |
| 42 | cyclopropylmethyl | 2 |
| 43 | cyclopentyl | 2 |
| 44 | cyclohexyl | 2 |
| 45 | phenyl | 2 |
| 46 | o-tolyl | 2 |

TABLE 1-continued

| Compound | R⁶ | Position |
|---|---|---|
| 47 | 4-methylphenyl | 2 |
| 48 | 4-(OCF₃)phenyl | 2 |
| 49 | 4-(t-butyl)phenyl | 2 |
| 50 | 2-(OCF₃)phenyl | 2 |
| 51 | 2-fluorophenyl | 2 |
| 52 | naphthalen-2-yl | 2 |
| 53 | —NH₂ | 2 |
| 54 | —NHCH₃ | 2 |
| 55 | —N(CH₃)₂ | 2 |
| 56 | pyrrolidin-1-yl | 2 |
| 57 | piperidin-1-yl | 2 |
| 58 | morpholin-4-yl | 2 |
| 59 | Methyl | 3 |
| 60 | Ethyl | 3 |
| 61 | Isopropyl | 3 |
| 62 | Butyl | 3 |
| 63 | t-Butyl | 3 |
| 64 | Propyl | 3 |
| 65 | Benzyl | 3 |
| 66 | Vinyl | 3 |
| 67 | Allyl | 3 |
| 68 | —CF₃ | 3 |
| 69 | cyclopropyl | 3 |
| 70 | cyclopropyl | 3 |
| 71 | cyclopropylmethyl | 3 |
| 72 | cyclopentyl | 3 |
| 73 | cyclohexyl | 3 |
| 74 | phenyl | 3 |
| 75 | 2-methylphenyl | 3 |
| 76 | 4-methylphenyl | 3 |
| 77 | 4-(OCF₃)phenyl | 3 |
| 78 | 4-(t-butyl)phenyl | 3 |
| 79 | 2-(OCF₃)phenyl | 3 |
| 80 | 2-fluorophenyl | 3 |
| 81 | naphthalen-2-yl | 3 |
| 82 | —NH₂ | 3 |
| 83 | —NHCH₃ | 3 |
| 84 | —N(CH₃)₂ | 3 |
| 85 | pyrrolidin-1-yl | 3 |
| 86 | piperidin-1-yl | 3 |
| 87 | morpholin-4-yl | 3 |

Representative compounds of the invention include, but are not limited to, the following compounds (compound 88 to compound 105 in Table 2) according to Formula XI, and pharmaceutically acceptable salts thereof, wherein $R^6$ and the substitution position for the acylsulfonamide are delineated for each compound in Table 2.

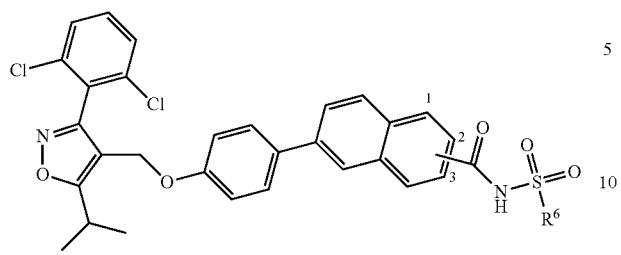
(XI)

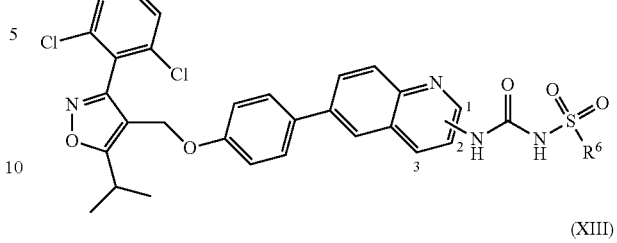
(XII)

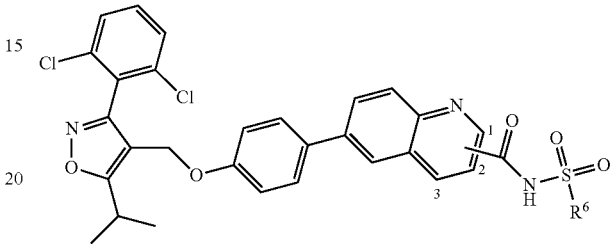
(XIII)

wherein $R^6$ is as previously defined, and the urea group in Formula (XII) or carbonyl group in Formula (XIII) is attached to quinolinyl at position 1, 2 or 3. Representative compounds of the invention include, but are not limited to, the following compounds (compound 106 to compound 192 in Table 3) according to Formula XII, and pharmaceutically acceptable salts thereof, wherein $R^6$ and the substitution position for the sulfonyl urea are delineated for each compound in Table 3.

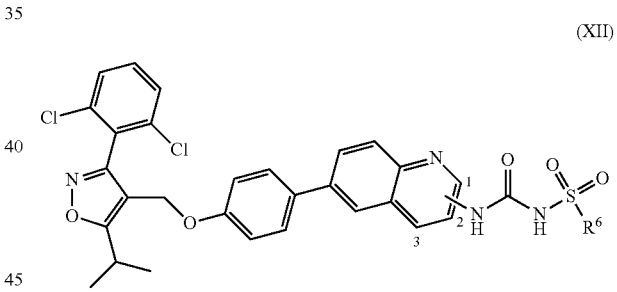
(XII)

TABLE 2

| Compound | $R^6$ | Position |
|---|---|---|
| 88 | —NH₂ | 1 |
| 89 | —NHCH₃ | 1 |
| 90 | —N(CH₃)₂ | 1 |
| 91 | pyrrolidinyl | 1 |
| 92 | piperidinyl | 1 |
| 93 | morpholinyl | 1 |
| 94 | —NH₂ | 2 |
| 95 | —NHCH₃ | 2 |
| 96 | —N(CH₃)₂ | 2 |
| 97 | pyrrolidinyl | 2 |
| 98 | piperidinyl | 2 |
| 99 | morpholinyl | 2 |
| 100 | —NH₂ | 3 |
| 101 | —NHCH₃ | 3 |
| 102 | —N(CH₃)₂ | 3 |
| 103 | pyrrolidinyl | 3 |
| 104 | piperidinyl | 3 |
| 105 | morpholinyl | 3 |

In certain embodiments, the compounds of the invention are represented by Formula XII or XIII and pharmaceutically acceptable salts, esters, stereoisomers, tautomers, solvates, hydrates and combinations thereof:

TABLE 3

| Compound | $R^6$ | Position |
|---|---|---|
| 106 | Methyl | 1 |
| 107 | Ethyl | 1 |
| 108 | Isopropyl | 1 |
| 109 | Butyl | 1 |
| 110 | t-Butyl | 1 |
| 111 | Propyl | 1 |
| 112 | Benzyl | 1 |
| 113 | Vinyl | 1 |
| 114 | Allyl | 1 |
| 115 | —CF₃ | 1 |
| 116 | cyclopropyl | 1 |
| 117 | cyclopropyl | 1 |

TABLE 3-continued
| Compound | R⁶ | Position |
|---|---|---|
| 118 | 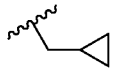 | 1 |
| 119 | 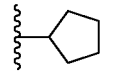 | 1 |
| 120 | 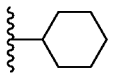 | 1 |
| 121 | 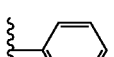 | 1 |
| 122 | 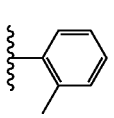 | 1 |
| 123 |  | 1 |
| 124 | 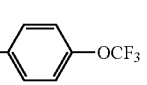 | 1 |
| 125 | 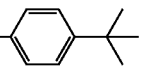 | 1 |
| 126 | 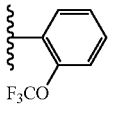 | 1 |
| 127 | 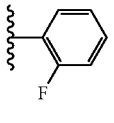 [SMILES: *c1ccccc1F] | 1 |
| 128 | 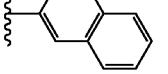 | 1 |
| 129 | —NH₂ | 1 |
| 130 | —NHCH₃ | 1 |
| 131 | —N(CH₃)₂ | 1 |
| 132 | 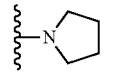 | 1 |
| 133 | 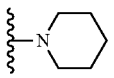 | 1 |
| 134 | 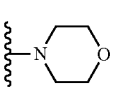 | 1 |
| 135 | Methyl | 2 |
| 136 | Ethyl | 2 |
| 137 | Isopropyl | 2 |
| 138 | Butyl | 2 |
| 139 | t-Butyl | 2 |
| 140 | Propyl | 2 |
| 141 | Benzyl | 2 |
| 142 | Vinyl | 2 |
| 143 | Allyl | 2 |
| 144 | —CF₃ | 2 |
| 145 |  | 2 |
| 146 |  | 2 |
| 147 |  | 2 |
| 148 |  | 2 |
| 149 |  | 2 |
| 150 |  | 2 |
| 151 |  | 2 |
| 152 |  | 2 |
| 153 |  | 2 |
| 154 |  | 2 |
| 155 |  | 2 |
| 156 |  | 2 |
| 157 |  | 2 |
| 158 | —NH₂ | 2 |
| 159 | —NHCH₃ | 2 |
| 160 | —N(CH₃)₂ | 2 |
| 161 |  | 2 |

TABLE 3-continued

| Compound | R⁶ | Position |
|---|---|---|
| 162 | piperidin-1-yl | 2 |
| 163 | morpholin-4-yl | 2 |
| 164 | Methyl | 3 |
| 165 | Ethyl | 3 |
| 166 | Isopropyl | 3 |
| 167 | Butyl | 3 |
| 168 | t-Butyl | 3 |
| 169 | Propyl | 3 |
| 170 | Benzyl | 3 |
| 171 | Vinyl | 3 |
| 172 | Allyl | 3 |
| 173 | —CF₃ | 3 |
| 174 | cyclopropyl | 3 |
| 175 | cyclopropyl | 3 |
| 176 | cyclopropylmethyl | 3 |
| 177 | cyclopentyl | 3 |
| 178 | cyclohexyl | 3 |
| 179 | phenyl | 3 |
| 180 | 2-methylphenyl | 3 |
| 181 | 4-methylphenyl | 3 |
| 182 | 4-trifluoromethoxyphenyl | 3 |
| 183 | 4-t-butylphenyl | 3 |
| 184 | 2-trifluoromethoxyphenyl | 3 |
| 185 | 2-fluorophenyl | 3 |
| 186 | 2-naphthyl | 3 |
| 187 | —NH₂ | 3 |
| 188 | —NHCH₃ | 3 |
| 189 | —N(CH₃)₂ | 3 |
| 190 | pyrrolidin-1-yl | 3 |
| 191 | piperidin-1-yl | 3 |
| 192 | morpholin-4-yl | 3 |

Representative compounds of the invention include, but are not limited to, the following compounds (compound 193 to compound 210 in Table 4) according to Formula XIII, and pharmaceutically acceptable salts thereof, wherein R⁶ and the substitution position for the acylsulfonamide are delineated for each compound in Table 4.

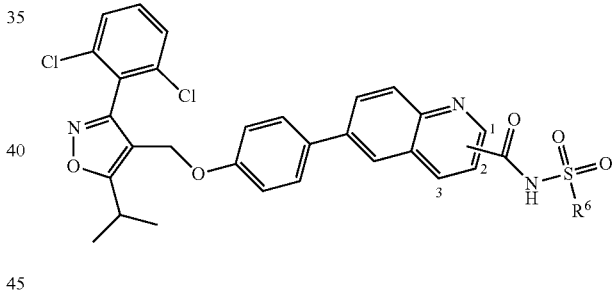

(XIII)

TABLE 4

| Compound | R⁶ | Position |
|---|---|---|
| 193 | —NH₂ | 1 |
| 194 | —NHCH₃ | 1 |
| 195 | —N(CH₃)₂ | 1 |
| 196 | pyrrolidin-1-yl | 1 |
| 197 | piperidin-1-yl | 1 |
| 198 | morpholin-4-yl | 1 |
| 199 | —NH₂ | 2 |
| 200 | —NHCH₃ | 2 |
| 201 | —N(CH₃)₂ | 2 |

TABLE 4-continued

| Compound | R⁶ | Position |
|---|---|---|
| 202 | pyrrolidinyl | 2 |
| 203 | piperidinyl | 2 |
| 204 | morpholinyl | 2 |
| 205 | —NH₂ | 3 |
| 206 | —NHCH₃ | 3 |
| 207 | —N(CH₃)₂ | 3 |
| 208 | pyrrolidinyl | 3 |
| 209 | piperidinyl | 3 |
| 210 | morpholinyl | 3 |

In certain embodiments, the compounds of the invention are represented by Formula XIV or XV and pharmaceutically acceptable salts thereof:

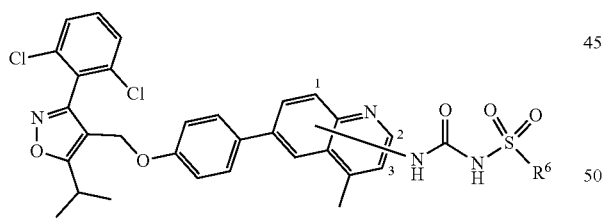

(XIV)

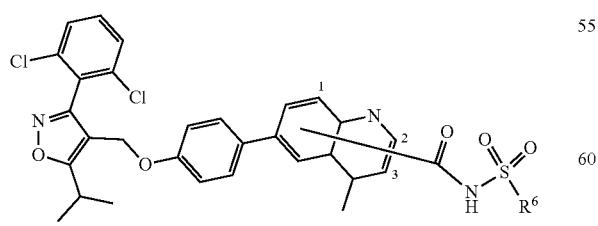

(XV)

wherein R⁶ is as previously defined, and the urea group in Formula (XIV) or carbonyl group in Formula (XV) is attached to

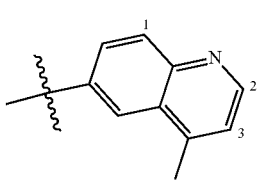

group at position 1, 2 or 3.

Representative compounds of the invention include, but are not limited to, the following compounds (compound 211 to compound 297 in Table 5) according to Formula XIV, and pharmaceutically acceptable salts thereof, wherein R⁶ and the substitution position for the sulfonyl urea are delineated for each compound in Table 5.

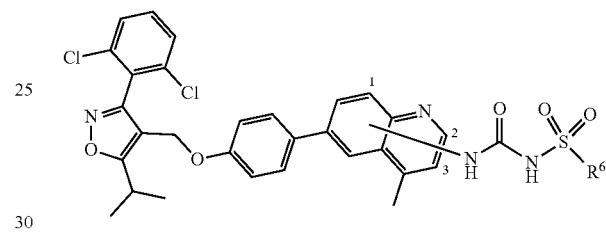

(XIV)

TABLE 5

| Compound | R⁶ | Position |
|---|---|---|
| 211 | Methyl | 1 |
| 212 | Ethyl | 1 |
| 213 | Isopropyl | 1 |
| 214 | Butyl | 1 |
| 215 | t-Butyl | 1 |
| 216 | Propyl | 1 |
| 217 | Benzyl | 1 |
| 218 | Vinyl | 1 |
| 219 | Allyl | 1 |
| 220 | —CF₃ | 1 |
| 221 | cyclopropyl | 1 |
| 222 | cyclopropyl | 1 |
| 223 | cyclopropylmethyl | 1 |
| 224 | cyclopentyl | 1 |
| 225 | cyclohexyl | 1 |
| 226 | phenyl | 1 |

TABLE 5-continued

| Compound | R⁶ | Position |
|---|---|---|
| 227 | 2-methylphenyl | 1 |
| 228 | 4-methylphenyl | 1 |
| 229 | 4-OCF₃-phenyl | 1 |
| 230 | 4-t-butylphenyl | 1 |
| 231 | 2-OCF₃-phenyl | 1 |
| 232 | 2-fluorophenyl | 1 |
| 233 | 2-naphthyl | 1 |
| 234 | —NH₂ | 1 |
| 235 | —NHCH₃ | 1 |
| 236 | —N(CH₃)₂ | 1 |
| 237 | pyrrolidin-1-yl | 1 |
| 238 | piperidin-1-yl | 1 |
| 239 | morpholin-4-yl | 1 |
| 240 | Methyl | 2 |
| 241 | Ethyl | 2 |
| 242 | Isopropyl | 2 |
| 243 | Butyl | 2 |
| 244 | t-Butyl | 2 |
| 245 | Propyl | 2 |
| 246 | Benzyl | 2 |
| 247 | Vinyl | 2 |
| 248 | Allyl | 2 |
| 249 | —CF₃ | 2 |
| 250 | cyclopropyl | 2 |
| 251 | cyclopropyl | 2 |
| 252 | cyclopropylmethyl | 2 |
| 253 | cyclopentyl | 2 |
| 254 | cyclohexyl | 2 |
| 255 | phenyl | 2 |
| 256 | 2-methylphenyl | 2 |
| 257 | 4-methylphenyl | 2 |
| 258 | 4-OCF₃-phenyl | 2 |
| 259 | 4-t-butylphenyl | 2 |
| 260 | 2-OCF₃-phenyl | 2 |
| 261 | 2-fluorophenyl | 2 |
| 262 | 2-naphthyl | 2 |
| 263 | —NH₂ | 2 |
| 264 | —NHCH₃ | 2 |
| 265 | —N(CH₃)₂ | 2 |
| 266 | pyrrolidin-1-yl | 2 |
| 267 | piperidin-1-yl | 2 |
| 268 | morpholin-4-yl | 2 |
| 269 | Methyl | 3 |
| 270 | Ethyl | 3 |
| 271 | Isopropyl | 3 |
| 272 | Butyl | 3 |
| 273 | t-Butyl | 3 |
| 274 | Propyl | 3 |
| 275 | Benzyl | 3 |
| 276 | Vinyl | 3 |
| 277 | Allyl | 3 |
| 278 | —CF₃ | 3 |

TABLE 5-continued

| Compound | R⁶ | Position |
|---|---|---|
| 279 | cyclopropyl | 3 |
| 280 | cyclopropyl (alt) | 3 |
| 281 | -CH₂-cyclopropyl | 3 |
| 282 | cyclopentyl | 3 |
| 283 | cyclohexyl | 3 |
| 284 | phenyl | 3 |
| 285 | 2-methylphenyl | 3 |
| 286 | 4-methylphenyl | 3 |
| 287 | 4-OCF₃-phenyl | 3 |
| 288 | 4-tert-butylphenyl | 3 |
| 289 | 2-OCF₃-phenyl | 3 |
| 290 | 2-fluorophenyl | 3 |
| 291 | 2-naphthyl | 3 |
| 292 | —NH₂ | 3 |
| 293 | —NHCH₃ | 3 |
| 294 | —N(CH₃)₂ | 3 |
| 295 | pyrrolidinyl | 3 |
| 296 | piperidinyl | 3 |
| 297 | morpholinyl | 3 |

Representative compounds of the invention include, but are not limited to, the following compounds (compound 298 to compound 315 in Table 6) according to Formula XV, and pharmaceutically acceptable salts thereof, wherein R⁶ and the substitution position for the acylsulfonamide are delineated for each compound in Table 6.

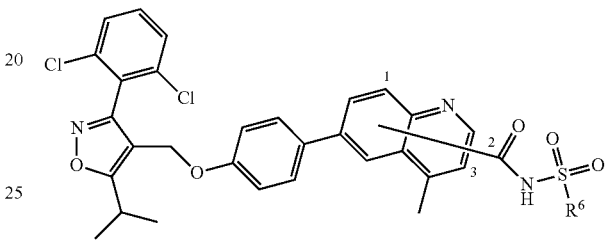

(XV)

TABLE 6

| Compound | R⁶ | Position |
|---|---|---|
| 298 | —NH₂ | 1 |
| 299 | —NHCH₃ | 1 |
| 300 | —N(CH₃)₂ | 1 |
| 301 | pyrrolidinyl | 1 |
| 302 | piperidinyl | 1 |
| 303 | morpholinyl | 1 |
| 304 | —NH₂ | 2 |
| 305 | —NHCH₃ | 2 |
| 306 | —N(CH₃)₂ | 2 |
| 307 | pyrrolidinyl | 2 |
| 308 | piperidinyl | 2 |
| 309 | morpholinyl | 2 |
| 310 | —NH₂ | 3 |
| 311 | —NHCH₃ | 3 |
| 312 | —N(CH₃)₂ | 3 |
| 313 | pyrrolidinyl | 3 |

TABLE 6-continued

| Compound | R⁶ | Position |
|---|---|---|
| 314 | 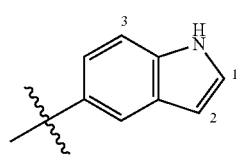 piperidinyl | 3 |
| 315 | morpholinyl | 3 |

In certain embodiments, the compounds of the invention are represented by Formula XVI or XVII and pharmaceutically acceptable salts thereof:

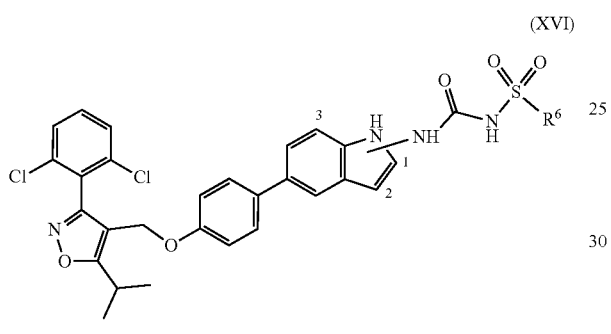

(XVI)

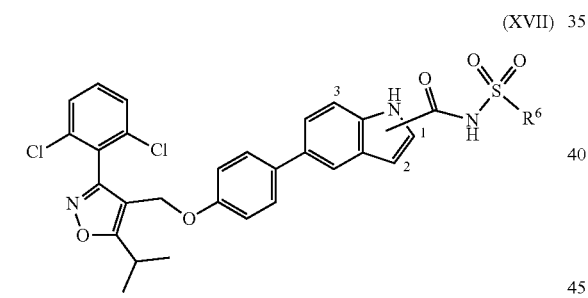

(XVII)

wherein R⁶ is as previously defined, and the urea group in Formula (XVI) or carbonyl group in Formula (XVII) is attached to

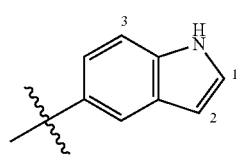

group at position 1, 2 or 3.

Representative compounds of the invention include, but are not limited to, the following compounds (compound 316 to compound 402 in Table 7) according to Formula XVI, and pharmaceutically acceptable salts thereof, wherein R⁶ and the substitution position for the sulfonyl urea are delineated for each compound in Table 7.

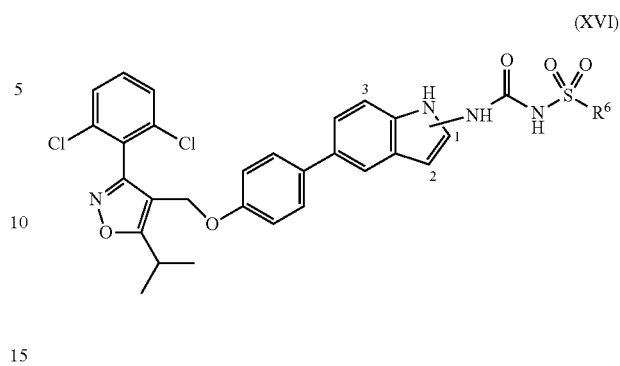

(XVI)

TABLE 7

| Compound | R⁶ | Position |
|---|---|---|
| 316 | Methyl | 1 |
| 317 | Ethyl | 1 |
| 318 | Isopropyl | 1 |
| 319 | Butyl | 1 |
| 320 | t-Butyl | 1 |
| 321 | Propyl | 1 |
| 322 | Benzyl | 1 |
| 323 | Vinyl | 1 |
| 324 | Allyl | 1 |
| 325 | —CF₃ | 1 |
| 326 | cyclopropyl | 1 |
| 327 | cyclopropyl | 1 |
| 328 | cyclopropylmethyl | 1 |
| 329 | cyclopentyl | 1 |
| 330 | cyclohexyl | 1 |
| 331 | phenyl | 1 |
| 332 | o-tolyl | 1 |
| 333 | p-tolyl | 1 |
| 334 | 4-OCF₃-phenyl | 1 |
| 335 | 4-t-butyl-phenyl | 1 |

TABLE 7-continued

| Compound | R⁶ | Position |
|---|---|---|
| 336 | 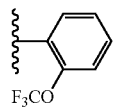 2-OCF₃-phenyl | 1 |
| 337 | 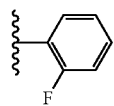 [SMILES: *c1ccccc1F] 2-F-phenyl | 1 |
| 338 | 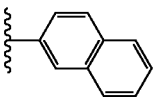 [SMILES: *c1ccc2ccccc2c1] naphthyl | 1 |
| 339 | —NH₂ | 1 |
| 340 | —NHCH₃ | 1 |
| 341 | —N(CH₃)₂ | 1 |
| 342 | 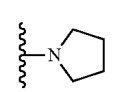 pyrrolidinyl | 1 |
| 343 | 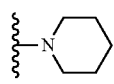 piperidinyl | 1 |
| 344 | 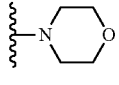 morpholinyl | 1 |
| 345 | Methyl | 2 |
| 346 | Ethyl | 2 |
| 347 | Isopropyl | 2 |
| 348 | Butyl | 2 |
| 349 | t-Butyl | 2 |
| 350 | Propyl | 2 |
| 351 | Benzyl | 2 |
| 352 | Vinyl | 2 |
| 353 | Allyl | 2 |
| 354 | —CF₃ | 2 |
| 355 | 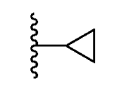 cyclopropyl | 2 |
| 356 | 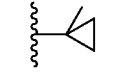 methylcyclopropyl | 2 |
| 357 | 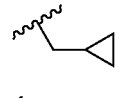 cyclopropylmethyl | 2 |
| 358 | 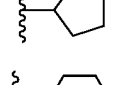 cyclopentyl | 2 |
| 359 | 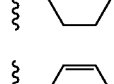 cyclohexyl | 2 |
| 360 | 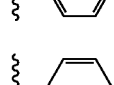 phenyl | 2 |
| 361 | 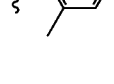 2-methylphenyl | 2 |
| 362 | 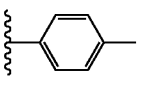 4-methylphenyl | 2 |
| 363 | 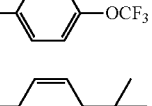 4-OCF₃-phenyl | 2 |
| 364 | 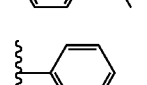 4-t-Bu-phenyl | 2 |
| 365 | 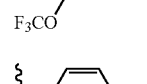 2-OCF₃-phenyl | 2 |
| 366 | 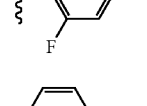 2-F-phenyl | 2 |
| 367 | 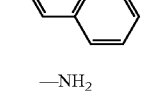 naphthyl | 2 |
| 368 | —NH₂ | 2 |
| 369 | —NHCH₃ | 2 |
| 370 | —N(CH₃)₂ | 2 |
| 371 | 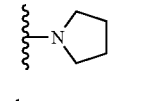 pyrrolidinyl | 2 |
| 372 | 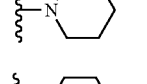 piperidinyl | 2 |
| 373 | 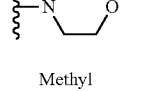 morpholinyl | 2 |
| 374 | Methyl | 3 |
| 375 | Ethyl | 3 |
| 376 | Isopropyl | 3 |
| 377 | Butyl | 3 |
| 378 | t-Butyl | 3 |
| 379 | Propyl | 3 |
| 380 | Benzyl | 3 |
| 381 | Vinyl | 3 |
| 382 | Allyl | 3 |
| 383 | —CF₃ | 3 |
| 384 | 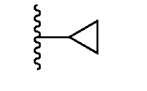 cyclopropyl | 3 |
| 385 | 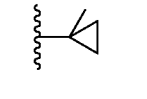 methylcyclopropyl | 3 |
| 386 | 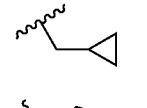 cyclopropylmethyl | 3 |
| 387 | 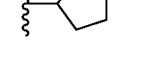 cyclopentyl | 3 |

TABLE 7-continued

| Compound | R⁶ | Position |
|---|---|---|
| 388 | cyclohexyl | 3 |
| 389 | phenyl | 3 |
| 390 | 2-methylphenyl | 3 |
| 391 | 4-methylphenyl | 3 |
| 392 | 4-OCF₃-phenyl | 3 |
| 393 | 4-tert-butyl-phenyl | 3 |
| 394 | 2-OCF₃-phenyl | 3 |
| 395 | 2-F-phenyl | 3 |
| 396 | naphthalen-2-yl | 3 |
| 397 | —NH₂ | 3 |
| 398 | —NHCH₃ | 3 |
| 399 | —N(CH₃)₂ | 3 |
| 400 | pyrrolidin-1-yl | 3 |
| 401 | piperidin-1-yl | 3 |
| 402 | morpholin-4-yl | 3 |

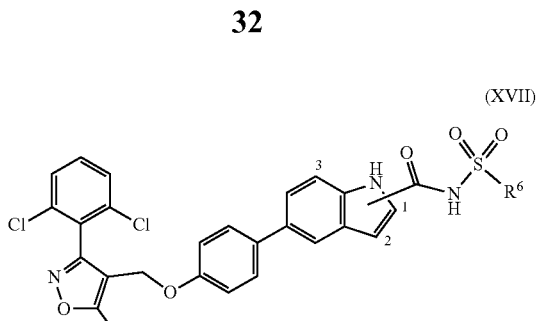

(XVII)

TABLE 8

| Compound | R⁶ | Position |
|---|---|---|
| 403 | —NH₂ | 1 |
| 404 | —NHCH₃ | 1 |
| 405 | —N(CH₃)₂ | 1 |
| 406 | pyrrolidin-1-yl | 1 |
| 407 | piperidin-1-yl | 1 |
| 408 | morpholin-4-yl | 1 |
| 409 | —NH₂ | 2 |
| 410 | —NHCH₃ | 2 |
| 411 | —N(CH₃)₂ | 2 |
| 412 | pyrrolidin-1-yl | 2 |
| 413 | piperidin-1-yl | 2 |
| 414 | morpholin-4-yl | 2 |
| 415 | —NH₂ | 3 |
| 416 | —NHCH₃ | 3 |
| 417 | —N(CH₃)₂ | 3 |
| 418 | pyrrolidin-1-yl | 3 |
| 419 | piperidin-1-yl | 3 |
| 420 | morpholin-4-yl | 3 |

Representative compounds of the invention include, but are not limited to, the following compounds (compound 403 to compound 420 in Table 8) according to Formula XVII, and pharmaceutically acceptable salts thereof, wherein $R^6$ and the substitution position for the acylsulfonamide are delineated for each compound in Table 8.

In certain embodiments, the compounds of the invention are represented by Formula XVIII or XIX and pharmaceutically acceptable salts thereof:

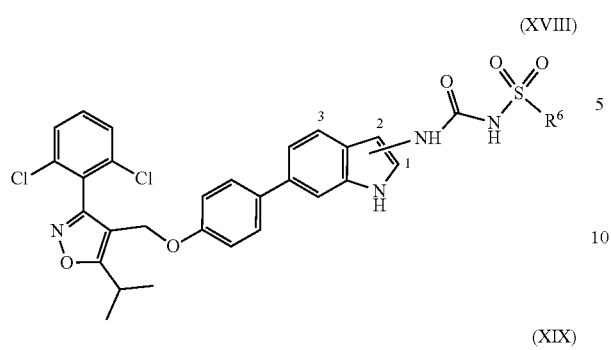

(XVIII)

(XIX)

wherein R⁶ is as previously defined, and the urea group in Formula (XVIII) or carbonyl group in Formula (XIX) is attached to

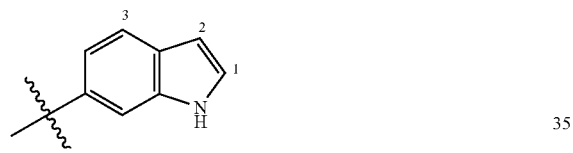

group at position 1, 2 or 3.

Representative compounds of the invention include, but are not limited to, the following compounds (compound 421 to compound 507 in Table 9) according to Formula XVIII, and pharmaceutically acceptable salts thereof, wherein R⁶ and the substitution position for the sulfonyl urea are delineated for each compound in Table 9.

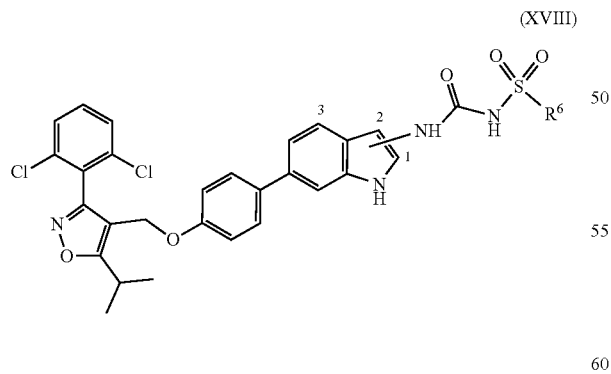

(XVIII)

TABLE 9

| Compound | R⁶ | Position |
|---|---|---|
| 421 | Methyl | 1 |
| 422 | Ethyl | 1 |
| 423 | Isopropyl | 1 |

TABLE 9-continued

| Compound | R⁶ | Position |
|---|---|---|
| 424 | Butyl | 1 |
| 425 | t-Butyl | 1 |
| 426 | Propyl | 1 |
| 427 | Benzyl | 1 |
| 428 | Vinyl | 1 |
| 429 | Allyl | 1 |
| 430 | —CF₃ | 1 |
| 431 | cyclopropyl | 1 |
| 432 | methylcyclopropyl | 1 |
| 433 | cyclopropylmethyl | 1 |
| 434 | cyclopentyl | 1 |
| 435 | cyclohexyl | 1 |
| 436 | phenyl | 1 |
| 437 | 2-methylphenyl | 1 |
| 438 | 4-methylphenyl | 1 |
| 439 | 4-OCF₃-phenyl | 1 |
| 440 | 4-t-butyl-phenyl | 1 |
| 441 | 2-OCF₃-phenyl | 1 |
| 442 | 2-F-phenyl | 1 |

TABLE 9-continued

| Compound | R⁶ | Position |
|---|---|---|
| 443 | naphthalen-2-yl | 1 |
| 444 | —NH₂ | 1 |
| 445 | —NHCH₃ | 1 |
| 446 | —N(CH₃)₂ | 1 |
| 447 | pyrrolidin-1-yl | 1 |
| 448 | piperidin-1-yl | 1 |
| 449 | morpholin-4-yl | 1 |
| 450 | Methyl | 2 |
| 451 | Ethyl | 2 |
| 452 | Isopropyl | 2 |
| 453 | Butyl | 2 |
| 454 | t-Butyl | 2 |
| 455 | Propyl | 2 |
| 456 | Benzyl | 2 |
| 457 | Vinyl | 2 |
| 458 | Allyl | 2 |
| 459 | —CF₃ | 2 |
| 460 | cyclopropyl | 2 |
| 461 | 1-methylcyclopropyl | 2 |
| 462 | cyclopropylmethyl | 2 |
| 463 | cyclopentyl | 2 |
| 464 | cyclohexyl | 2 |
| 465 | phenyl | 2 |
| 466 | 2-methylphenyl | 2 |
| 467 | 4-methylphenyl | 2 |
| 468 | 4-(trifluoromethoxy)phenyl | 2 |
| 469 | 4-tert-butylphenyl | 2 |
| 470 | 2-(trifluoromethoxy)phenyl | 2 |
| 471 | 2-fluorophenyl | 2 |
| 472 | naphthalen-2-yl | 2 |
| 473 | —NH₂ | 2 |
| 474 | —NHCH₃ | 2 |
| 475 | —N(CH₃)₂ | 2 |
| 476 | pyrrolidin-1-yl | 2 |
| 477 | piperidin-1-yl | 2 |
| 478 | morpholin-4-yl | 2 |
| 479 | Methyl | 1 |
| 480 | Ethyl | 3 |
| 481 | Isopropyl | 3 |
| 482 | Butyl | 3 |
| 483 | t-Butyl | 3 |
| 484 | Propyl | 3 |
| 485 | Benzyl | 3 |
| 486 | Vinyl | 3 |
| 487 | Allyl | 3 |
| 488 | —CF₃ | 3 |
| 489 | cyclopropyl | 3 |

TABLE 9-continued

| Compound | R⁶ | Position |
|---|---|---|
| 490 | (1-methylcyclopropyl) | 3 |
| 491 | (cyclopropylmethyl) | 3 |
| 492 | (cyclopentyl) | 3 |
| 493 | (cyclohexyl) | 3 |
| 494 | (phenyl) | 3 |
| 495 | (2-methylphenyl) | 3 |
| 496 | (4-methylphenyl) | 3 |
| 497 | (4-OCF₃-phenyl) | 3 |
| 498 | (4-tert-butylphenyl) | 3 |
| 499 | (2-OCF₃-phenyl) | 3 |
| 500 | (2-fluorophenyl) | 3 |
| 501 | (2-naphthyl) | 3 |
| 502 | —NH₂ | 3 |
| 503 | —NHCH₃ | 3 |
| 504 | —N(CH₃)₂ | 3 |

TABLE 9-continued

| Compound | R⁶ | Position |
|---|---|---|
| 505 | (pyrrolidin-1-yl) | 3 |
| 506 | (piperidin-1-yl) | 3 |
| 507 | (morpholin-4-yl) | 3 |

Representative compounds of the invention include, but are not limited to, the following compounds (compound 508 to compound 525 in Table 10) according to Formula XIX, and pharmaceutically acceptable salts thereof, wherein R⁶ and the substitution position for the acylsulfonamide are delineated for each compound in Table 10.

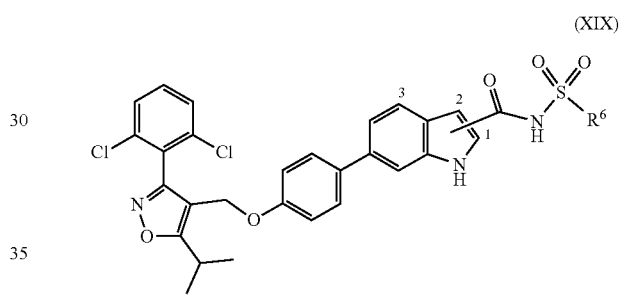

(XIX)

TABLE 10

| Compound | R⁶ | Position |
|---|---|---|
| 508 | —NH₂ | 1 |
| 509 | —NHCH₃ | 1 |
| 510 | —N(CH₃)₂ | 1 |
| 511 | (pyrrolidin-1-yl) | 1 |
| 512 | (piperidin-1-yl) | 1 |
| 513 | (morpholin-4-yl) | 1 |
| 514 | —NH₂ | 2 |
| 515 | —NHCH₃ | 2 |
| 516 | —N(CH₃)₂ | 2 |
| 517 | (pyrrolidin-1-yl) | 2 |

TABLE 10-continued

| Compound | R⁶ | Position |
|---|---|---|
| 518 | 2-fluorophenyl | 2 |
| 519 | morpholino (N-linked) | 2 |
| 520 | —NH₂ | 3 |
| 521 | —NHCH₃ | 3 |
| 522 | —N(CH₃)₂ | 3 |
| 523 | pyrrolidin-1-yl | 3 |
| 524 | piperidin-1-yl | 3 |
| 525 | morpholino (N-linked) | 3 |

In certain embodiments, the compounds of the invention are represented by Formula XX or XXI and pharmaceutically acceptable salts thereof:

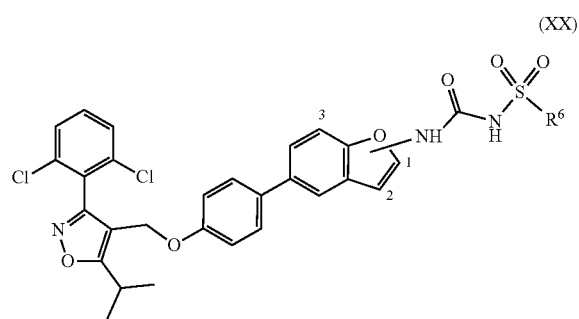

(XX)

(XXI)

wherein R⁶ is as previously defined, and the urea group in Formula (XX) or carbonyl group in Formula (XXI) is attached to group at position 1, 2 or 3.

Representative compounds of the invention include, but are not limited to, the following compounds (compound 526 to compound 612 in Table 11) according to Formula XX, and pharmaceutically acceptable salts thereof, wherein R⁶ and the substitution position for the sulfonyl urea are delineated for each compound in Table 11.

(XX)

TABLE 11

| Compound | R⁶ | Position |
|---|---|---|
| 526 | Methyl | 1 |
| 527 | Ethyl | 1 |
| 528 | Isopropyl | 1 |
| 529 | Butyl | 1 |
| 530 | t-Butyl | 1 |
| 531 | Propyl | 1 |
| 532 | Benzyl | 1 |
| 533 | Vinyl | 1 |
| 534 | Allyl | 1 |
| 535 | —CF₃ | 1 |
| 536 | cyclopropyl | 1 |
| 537 | cyclopropyl | 1 |
| 538 | cyclopropylmethyl | 1 |
| 539 | cyclopentyl | 1 |
| 540 | cyclohexyl | 1 |

TABLE 11-continued
| Compound | R⁶ | Position |
|---|---|---|
| 541 | 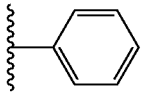 | 1 |
| 542 | 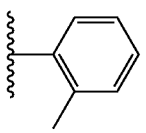 [SMILES: *c1ccccc1C] | 1 |
| 543 |  | 1 |
| 544 | 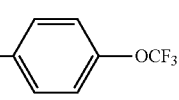 | 1 |
| 545 | 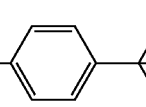 | 1 |
| 546 | 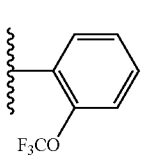 | 1 |
| 547 | 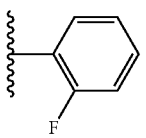 [SMILES: *c1ccccc1F] | 1 |
| 548 | 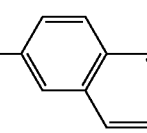 | 1 |
| 549 | —NH₂ | 1 |
| 550 | —NHCH₃ | 1 |
| 551 | —N(CH₃)₂ | 1 |
| 552 | 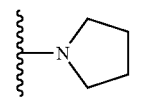 | 1 |
| 553 | 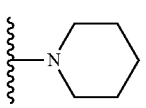 | 1 |
| 554 | 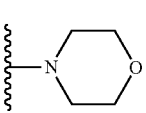 | 1 |
| 555 | Methyl | 2 |
| 556 | Ethyl | 2 |
| 557 | Isopropyl | 2 |
| 558 | Butyl | 2 |
| 559 | t-Butyl | 2 |
| 560 | Propyl | 2 |
| 561 | Benzyl | 2 |
| 562 | Vinyl | 2 |
| 563 | Allyl | 2 |
| 564 | —CF₃ | 2 |
| 565 |  | 2 |
| 566 |  | 2 |
| 567 |  | 2 |
| 568 |  | 2 |
| 569 |  | 2 |
| 570 |  | 2 |
| 571 |  | 2 |
| 572 |  | 2 |
| 573 |  | 2 |
| 574 |  | 2 |
| 575 |  | 2 |
| 576 |  | 2 |

TABLE 11-continued

| Compound | R⁶ | Position |
|---|---|---|
| 577 | (2-naphthyl) | 2 |
| 578 | —NH₂ | 2 |
| 579 | —NHCH₃ | 2 |
| 580 | —N(CH₃)₂ | 2 |
| 581 | (pyrrolidinyl) | 2 |
| 582 | (piperidinyl) | 2 |
| 583 | (morpholinyl) | 2 |
| 584 | Methyl | 3 |
| 585 | Ethyl | 3 |
| 586 | Isopropyl | 3 |
| 587 | Butyl | 3 |
| 588 | t-Butyl | 3 |
| 589 | Propyl | 3 |
| 590 | Benzyl | 3 |
| 591 | Vinyl | 3 |
| 592 | Allyl | 3 |
| 593 | —CF₃ | 3 |
| 594 | (cyclopropyl) | 3 |
| 595 | (cyclopropyl) | 3 |
| 596 | (cyclopropylmethyl) | 3 |
| 597 | (cyclopentyl) | 3 |
| 598 | (cyclohexyl) | 3 |
| 599 | (phenyl) | 3 |
| 600 | (2-methylphenyl) | 3 |
| 601 | (4-methylphenyl) | 3 |
| 602 | (4-OCF₃-phenyl) | 3 |
| 603 | (4-t-butylphenyl) | 3 |
| 604 | (2-OCF₃-phenyl) | 3 |
| 605 | (2-fluorophenyl) | 3 |
| 606 | (2-naphthyl) | 3 |
| 607 | —NH₂ | 3 |
| 608 | —NHCH₃ | 3 |
| 609 | —N(CH₃)₂ | 3 |
| 610 | (pyrrolidinyl) | 3 |
| 611 | (piperidinyl) | 3 |
| 612 | (morpholinyl) | 3 |

Representative compounds of the invention include, but are not limited to, the following compounds (compound 613 to compound 630 in Table 12) according to Formula XXI, and pharmaceutically acceptable salts thereof, wherein R⁶ and the substitution position for the acylsulfonamide are delineated for each compound in Table 12.

(XXI)

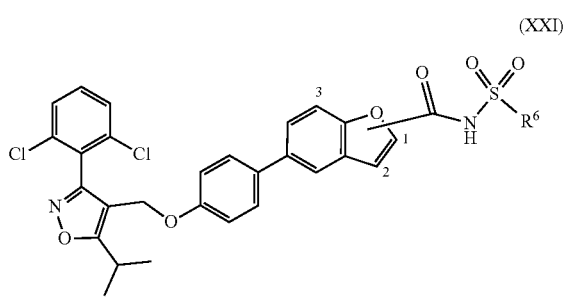

TABLE 12

| Compound | R⁶ | Position |
|---|---|---|
| 613 | —NH$_2$ | 1 |
| 614 | —NHCH$_3$ | 1 |
| 615 | —N(CH$_3$)$_2$ | 1 |
| 616 | pyrrolidinyl | 1 |
| 617 | piperidinyl | 1 |
| 618 | morpholinyl | 1 |
| 619 | —NH$_2$ | 2 |
| 620 | —NHCH$_3$ | 2 |
| 621 | —N(CH$_3$)$_2$ | 2 |
| 622 | pyrrolidinyl | 2 |
| 623 | piperidinyl | 2 |
| 624 | morpholinyl | 2 |
| 625 | —NH$_2$ | 3 |
| 626 | —NHCH$_3$ | 3 |
| 627 | —N(CH$_3$)$_2$ | 3 |
| 628 | pyrrolidinyl | 3 |
| 629 | piperidinyl | 3 |

TABLE 12-continued

| Compound | R⁶ | Position |
|---|---|---|
| 630 | morpholinyl | 3 |

In certain embodiments, the compounds of the invention are represented by Formula XXII or XXIII and pharmaceutically acceptable salts thereof:

(XXII)

(XXIII)

wherein R⁶ is as previously defined, and the urea group in Formula (XXII) or carbonyl group in Formula (XXIII) is attached to

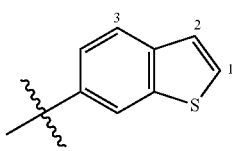 [SMILES: *c1ccc2ccsc2c1]

group at position 1, 2 or 3.

Representative compounds of the invention include, but are not limited to, the following compounds (compound 631 to compound 717 in Table 13) according to Formula XXII, and pharmaceutically acceptable salts thereof, wherein R⁶ and the substitution position for the sulfonyl urea are delineated for each compound in Table 13.

(XXII)

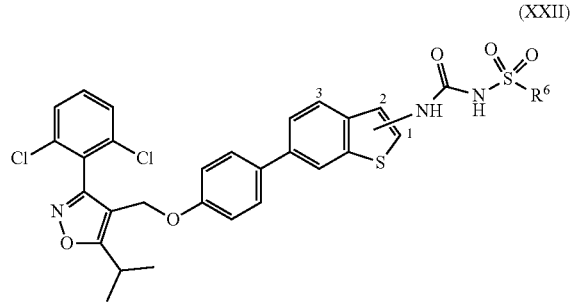

TABLE 13

| Compound | R⁶ | Position |
|---|---|---|
| 631 | Methyl | 1 |
| 632 | Ethyl | 1 |
| 633 | Isopropyl | 1 |
| 634 | Butyl | 1 |
| 635 | t-Butyl | 1 |
| 636 | Propyl | 1 |
| 637 | Benzyl | 1 |
| 638 | Vinyl | 1 |
| 639 | Allyl | 1 |
| 640 | —CF₃ | 1 |
| 641 | cyclopropyl | 1 |
| 642 | 1-methylcyclopropyl | 1 |
| 643 | cyclopropylmethyl | 1 |
| 644 | cyclopentyl | 1 |
| 645 | cyclohexyl | 1 |
| 646 | phenyl | 1 |
| 647 | 2-methylphenyl | 1 |
| 648 | 4-methylphenyl | 1 |

TABLE 13-continued

| Compound | R⁶ | Position |
|---|---|---|
| 649 | 4-OCF₃-phenyl | 1 |
| 650 | 4-t-butylphenyl | 1 |
| 651 | 2-OCF₃-phenyl | 1 |
| 652 | 2-F-phenyl | 1 |
| 653 | naphthyl | 1 |
| 654 | —NH₂ | 1 |
| 655 | —NHCH₃ | 1 |
| 656 | —N(CH₃)₂ | 1 |
| 657 | pyrrolidinyl | 1 |
| 658 | piperidinyl | 1 |
| 659 | morpholinyl | 1 |
| 660 | Methyl | 2 |
| 661 | Ethyl | 2 |
| 662 | Isopropyl | 2 |
| 663 | Butyl | 2 |
| 664 | t-Butyl | 2 |
| 665 | Propyl | 2 |
| 666 | Benzyl | 2 |
| 667 | Vinyl | 2 |
| 668 | Allyl | 2 |
| 669 | —CF₃ | 2 |
| 670 | cyclopropyl | 2 |
| 671 | 1-methylcyclopropyl | 2 |

TABLE 13-continued
| Compound | R⁶ | Position |
|---|---|---|
| 672 | 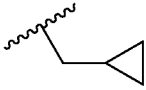 [SMILES: *CC1CC1] | 2 |
| 673 | 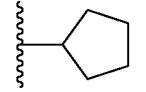 [SMILES: *C1CCCC1] | 2 |
| 674 | 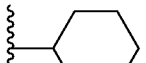 | 2 |
| 675 | 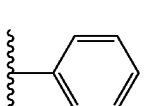 | 2 |
| 676 | 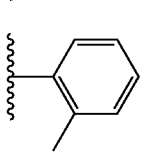 | 2 |
| 677 | 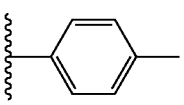 [SMILES: *c1ccc(C)cc1] | 2 |
| 678 | 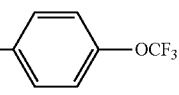 | 2 |
| 679 | 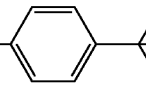 | 2 |
| 680 | 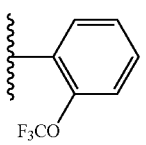 | 2 |
| 681 | 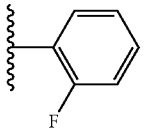 | 2 |
| 682 | 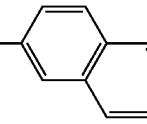 | 2 |
| 683 | —NH₂ | 2 |
| 684 | —NHCH₃ | 2 |
| 685 | —N(CH₃)₂ | 2 |
| 686 | 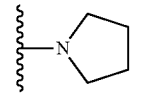 | 2 |
| 687 | 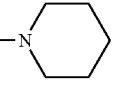 | 2 |
| 688 | 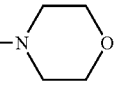 | 2 |
| 689 | Methyl | 3 |
| 690 | Ethyl | 3 |
| 691 | Isopropyl | 3 |
| 692 | Butyl | 3 |
| 693 | t-Butyl | 3 |
| 694 | Propyl | 3 |
| 695 | Benzyl | 3 |
| 696 | Vinyl | 3 |
| 697 | Allyl | 3 |
| 698 | —CF₃ | 3 |
| 699 |  | 3 |
| 700 |  | 3 |
| 701 | 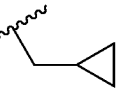 | 3 |
| 702 | 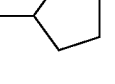 | 3 |
| 703 | 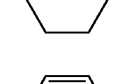 | 3 |
| 704 | 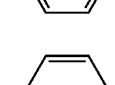 | 3 |
| 705 | 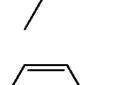 | 3 |
| 706 | 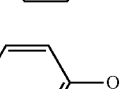 | 3 |
| 707 | 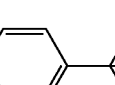 | 3 |
| 708 |  | 3 |

TABLE 13-continued

| Compound | R⁶ | Position |
|---|---|---|
| 709 | 2-(F₃CO)phenyl | 3 |
| 710 | 2-F-phenyl | 3 |
| 711 | 2-naphthyl | 3 |
| 712 | —NH₂ | 3 |
| 713 | —NHCH₃ | 3 |
| 714 | —N(CH₃)₂ | 3 |
| 715 | pyrrolidin-1-yl | 3 |
| 716 | piperidin-1-yl | 3 |
| 717 | morpholin-4-yl | 3 |

Representative compounds of the invention include, but are not limited to, the following compounds (compound 718 to compound 735 in Table 14) according to Formula XXIII, and pharmaceutically acceptable salts thereof, wherein R⁶ and the substitution position for the acylsulfonamide are delineated for each compound in Table 14.

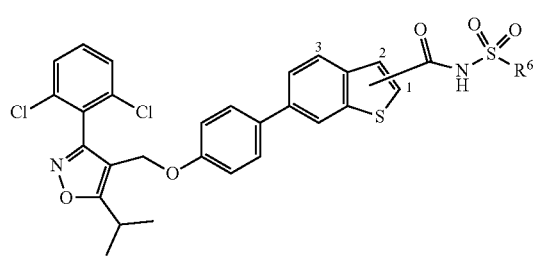

(XXIII)

TABLE 14

| Compound | R⁶ | Position |
|---|---|---|
| 718 | —NH₂ | 1 |
| 719 | —NHCH₃ | 1 |
| 720 | —N(CH₃)₂ | 1 |
| 721 | pyrrolidin-1-yl | 1 |
| 722 | piperidin-1-yl | 1 |
| 723 | morpholin-4-yl | 1 |
| 724 | —NH₂ | 2 |
| 725 | —NHCH₃ | 2 |
| 726 | —N(CH₃)₂ | 2 |
| 727 | pyrrolidin-1-yl | 2 |
| 728 | piperidin-1-yl | 2 |
| 729 | morpholin-4-yl | 2 |
| 730 | —NH₂ | 3 |
| 731 | —NHCH₃ | 3 |
| 732 | —N(CH₃)₂ | 3 |
| 733 | pyrrolidin-1-yl | 3 |
| 734 | piperidin-1-yl | 3 |
| 735 | morpholin-4-yl | 3 |

In certain embodiments, the compounds of the invention are represented by Formula XXIV or XXV and pharmaceutically acceptable salts thereof:

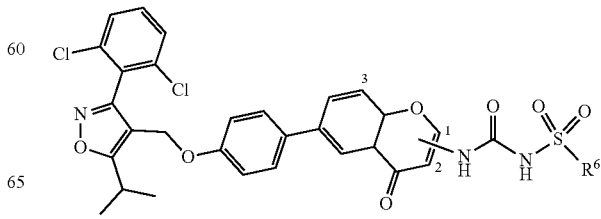

(XXIV)

(XXV)

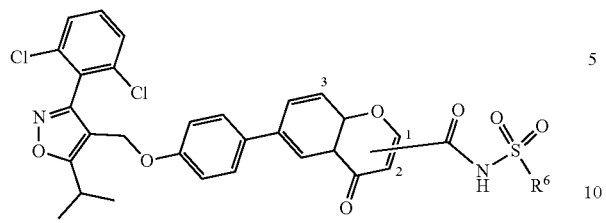

wherein R⁶ is as previously defined, and the urea group in Formula (XXIII) or carbonyl group in Formula (XXIV) is attached to

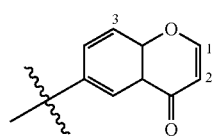

group at position 1, 2 or 3.

Representative compounds of the invention include, but are not limited to, the following compounds (compound 736 to compound 822 in Table 15) according to Formula XXVI, and pharmaceutically acceptable salts thereof, wherein $R^6$ and the substitution position for the sulfonyl urea are delineated for each compound in Table 15.

(XXIV)

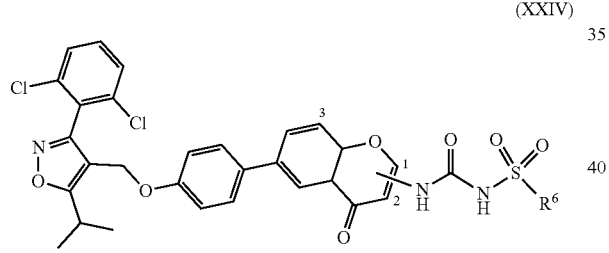

TABLE 15

| Compound | R⁶ | Position |
|---|---|---|
| 736 | Methyl | 1 |
| 737 | Ethyl | 1 |
| 738 | Isopropyl | 1 |
| 739 | Butyl | 1 |
| 740 | t-Butyl | 1 |
| 741 | Propyl | 1 |
| 742 | Benzyl | 1 |
| 743 | Vinyl | 1 |
| 744 | Allyl | 1 |
| 745 | —CF₃ | 1 |
| 746 | cyclopropyl | 1 |
| 747 | methylenecyclopropyl | 1 |
| 748 | cyclopropylmethyl | 1 |
| 749 | cyclopentyl | 1 |
| 750 | cyclohexyl | 1 |
| 751 | phenyl | 1 |
| 752 | o-tolyl | 1 |
| 753 | p-tolyl | 1 |
| 754 | 4-OCF₃-phenyl | 1 |
| 755 | 4-t-butyl-phenyl | 1 |
| 756 | 2-OCF₃-phenyl | 1 |
| 757 | 2-F-phenyl | 1 |
| 758 | naphthyl | 1 |
| 759 | —NH₂ | 1 |
| 760 | —NHCH₃ | 1 |
| 761 | —N(CH₃)₂ | 1 |
| 762 | pyrrolidinyl | 1 |

TABLE 15-continued

| Compound | R⁶ | Position |
|---|---|---|
| 763 | N-piperidinyl | 1 |
| 764 | N-morpholinyl | 1 |
| 765 | Methyl | 2 |
| 766 | Ethyl | 2 |
| 767 | Isopropyl | 2 |
| 768 | Butyl | 2 |
| 769 | t-Butyl | 2 |
| 770 | Propyl | 2 |
| 771 | Benzyl | 2 |
| 772 | Vinyl | 2 |
| 773 | Allyl | 2 |
| 774 | —CF₃ | 2 |
| 775 | cyclopropyl | 2 |
| 776 | 1-methylcyclopropyl | 2 |
| 777 | cyclopropylmethyl | 2 |
| 778 | cyclopentyl | 2 |
| 779 | cyclohexyl | 2 |
| 780 | phenyl | 2 |
| 781 | 2-methylphenyl | 2 |
| 782 | 4-methylphenyl | 2 |
| 783 | 4-(trifluoromethoxy)phenyl | 2 |
| 784 | 4-t-butylphenyl | 2 |
| 785 | 2-(trifluoromethoxy)phenyl | 2 |
| 786 | 2-fluorophenyl | 2 |
| 787 | 2-naphthyl | 2 |
| 788 | —NH₂ | 2 |
| 789 | —NHCH₃ | 2 |
| 790 | —N(CH₃)₂ | 2 |
| 791 | N-pyrrolidinyl | 2 |
| 792 | N-piperidinyl | 2 |
| 793 | N-morpholinyl | 2 |
| 794 | Methyl | 3 |
| 795 | Ethyl | 3 |
| 796 | Isopropyl | 3 |
| 797 | Butyl | 3 |
| 798 | t-Butyl | 3 |
| 799 | Propyl | 3 |
| 800 | Benzyl | 3 |
| 801 | Vinyl | 3 |
| 802 | Allyl | 3 |
| 803 | —CF₃ | 3 |
| 804 | cyclopropyl | 3 |
| 805 | 1-methylcyclopropyl | 3 |
| 806 | cyclopropylmethyl | 3 |
| 807 | cyclopentyl | 3 |

TABLE 15-continued

| Compound | R⁶ | Position |
|---|---|---|
| 808 | cyclohexyl | 3 |
| 809 | phenyl | 3 |
| 810 | 2-methylphenyl | 3 |
| 811 | 4-methylphenyl | 3 |
| 812 | 4-OCF₃-phenyl | 3 |
| 813 | 4-tert-butylphenyl | 3 |
| 814 | 2-OCF₃-phenyl | 3 |
| 815 | 2-fluorophenyl | 3 |
| 816 | 2-naphthyl | 3 |
| 817 | —NH₂ | 3 |
| 818 | —NHCH₃ | 3 |
| 819 | —N(CH₃)₂ | 3 |
| 820 | pyrrolidinyl | 3 |
| 821 | piperidinyl | 3 |
| 822 | morpholinyl | 3 |

Representative compounds of the invention include, but are not limited to, the following compounds (compound 823 to compound 840 in Table 16) according to Formula XXV, and pharmaceutically acceptable salts thereof, wherein R⁶ and the substitution position for the acylsulfonamide are delineated for each compound in Table 16.

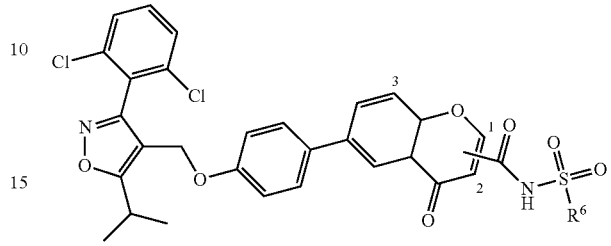

(XXV)

TABLE 16

| Compound | R⁶ | Position |
|---|---|---|
| 823 | —NH2 | 1 |
| 824 | —NHCH3 | 1 |
| 825 | —N(CH3)2 | 1 |
| 826 | pyrrolidinyl | 1 |
| 827 | piperidinyl | 1 |
| 828 | morpholinyl | 1 |
| 829 | —NH2 | 2 |
| 830 | —NHCH3 | 2 |
| 831 | —N(CH3)2 | 2 |
| 832 | pyrrolidinyl | 2 |
| 833 | piperidinyl | 2 |
| 834 | morpholinyl | 2 |
| 835 | —NH2 | 3 |
| 836 | —NHCH3 | 3 |
| 837 | —N(CH3)2 | 3 |
| 838 | pyrrolidinyl | 3 |
| 839 | piperidinyl | 3 |

TABLE 16-continued

| Compound | R⁶ | Position |
|---|---|---|
| 840 | 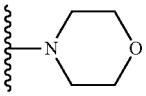 | 3 |

In certain embodiments, the compounds of the invention are represented by Formula XXVI or XXVII and pharmaceutically acceptable salts thereof:

(XXVI)

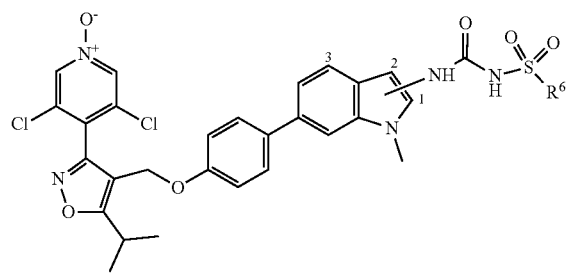

(XXVII)

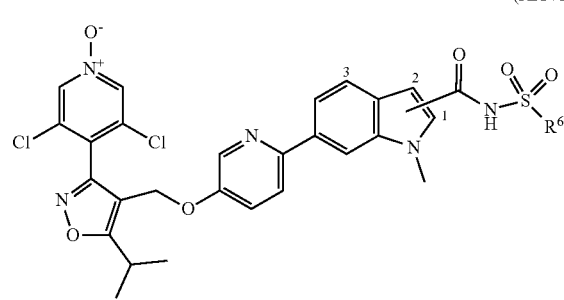

wherein R⁶ is as previously defined, and the urea group in Formula (XXVI) or carbonyl group in Formula (XXVII) is attached to

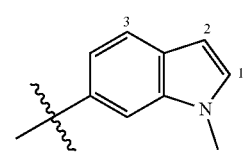 [SMILES: *c1ccc2ccn(C)c2c1]

group at position 1, 2 or 3.

Representative compounds of the invention include, but are not limited to, the following compounds (compound 841 to compound 927 in Table 17) according to Formula XXVI, and pharmaceutically acceptable salts thereof, wherein R⁶ and the substitution position for the sulfonyl urea are delineated for each compound in Table 17.

(XXVI)

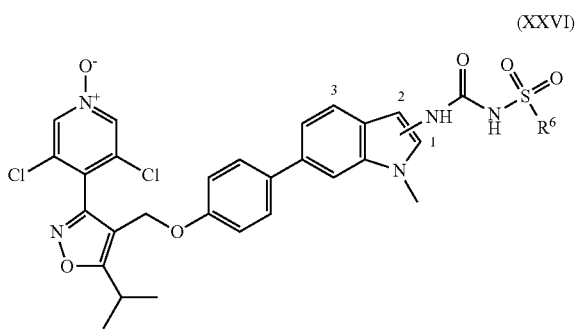

TABLE 17

| Compound | R⁶ | Position |
|---|---|---|
| 841 | Methyl | 1 |
| 842 | Ethyl | 1 |
| 843 | Isopropyl | 1 |
| 844 | Butyl | 1 |
| 845 | t-Butyl | 1 |
| 846 | Propyl | 1 |
| 847 | Benzyl | 1 |
| 848 | Vinyl | 1 |
| 849 | Allyl | 1 |
| 850 | —CF3 | 1 |
| 851 |  | 1 |
| 852 |  | 1 |
| 853 |  | 1 |
| 854 |  | 1 |
| 855 |  | 1 |
| 856 |  | 1 |
| 857 |  | 1 |
| 858 |  | 1 |

TABLE 17-continued

| Compound | R⁶ | Position |
|---|---|---|
| 859 | 4-(OCF₃)phenyl | 1 |
| 860 | 4-(t-Bu)phenyl | 1 |
| 861 | 2-(OCF₃)phenyl | 1 |
| 862 | 2-F-phenyl | 1 |
| 863 | naphthalen-2-yl | 1 |
| 864 | —NH2 | 1 |
| 865 | —NHCH3 | 1 |
| 866 | —N(CH3)2 | 1 |
| 867 | pyrrolidin-1-yl | 1 |
| 868 | piperidin-1-yl | 1 |
| 869 | morpholin-4-yl | 1 |
| 870 | Methyl | 2 |
| 871 | Ethyl | 2 |
| 872 | Isopropyl | 2 |
| 873 | Butyl | 2 |
| 874 | t-Butyl | 2 |
| 875 | Propyl | 2 |
| 876 | Benzyl | 2 |
| 877 | Vinyl | 2 |
| 878 | Allyl | 2 |
| 879 | —CF3 | 2 |
| 880 | cyclopropyl | 2 |
| 881 | 1-methylcyclopropyl | 2 |
| 882 | cyclopropylmethyl | 2 |
| 883 | cyclopentyl | 2 |
| 884 | cyclohexyl | 2 |
| 885 | phenyl | 2 |
| 886 | 2-methylphenyl | 2 |
| 887 | 4-methylphenyl | 2 |
| 888 | 4-(OCF₃)phenyl | 2 |
| 889 | 4-(t-Bu)phenyl | 2 |
| 890 | 2-(OCF₃)phenyl | 2 |
| 891 | 2-F-phenyl | 2 |
| 892 | naphthalen-2-yl | 2 |
| 893 | —NH2 | 2 |
| 894 | —NHCH3 | 2 |
| 895 | —N(CH3)2 | 2 |
| 896 | pyrrolidin-1-yl | 2 |

TABLE 17-continued

| Compound | R⁶ | Position |
|---|---|---|
| 897 | piperidinyl (N-linked) | 2 |
| 898 | morpholinyl (N-linked) | 2 |
| 899 | Methyl | 3 |
| 900 | Ethyl | 3 |
| 901 | Isopropyl | 3 |
| 902 | Butyl | 3 |
| 903 | t-Butyl | 3 |
| 904 | Propyl | 3 |
| 905 | Benzyl | 3 |
| 906 | Vinyl | 3 |
| 907 | Allyl | 3 |
| 908 | —CF3 | 3 |
| 909 | cyclopropyl | 3 |
| 910 | 1-methylcyclopropyl | 3 |
| 911 | cyclopropylmethyl | 3 |
| 912 | cyclopentyl | 3 |
| 913 | cyclohexyl | 3 |
| 914 | phenyl | 3 |
| 915 | 2-methylphenyl | 3 |
| 916 | 4-methylphenyl | 3 |
| 917 | 4-OCF3-phenyl | 3 |
| 918 | 4-t-butylphenyl | 3 |
| 919 | 2-OCF3-phenyl | 3 |
| 920 | 2-F-phenyl | 3 |
| 921 | 2-naphthyl | 3 |
| 922 | —NH2 | 3 |
| 923 | —NHCH3 | 3 |
| 924 | —N(CH3)2 | 3 |
| 925 | pyrrolidinyl (N-linked) | 3 |
| 926 | piperidinyl (N-linked) | 3 |
| 927 | morpholinyl (N-linked) | 3 |

Representative compounds of the invention include, but are not limited to, the following compounds (compound 928 to compound 945 in Table 18) according to Formula XXVII, and pharmaceutically acceptable salts thereof, wherein R⁶ and the substitution position for the acylsulfonamide are delineated for each compound in Table 18.

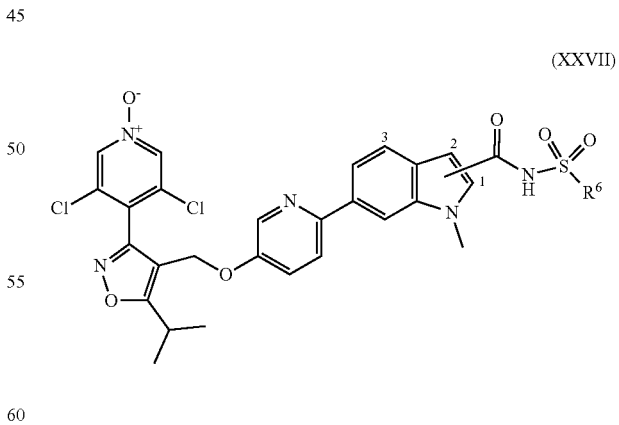

(XXVII)

TABLE 18

| Compound | R⁶ | Position |
|---|---|---|
| 928 | —NH₂ | 1 |
| 929 | —NHCH₃ | 1 |
| 930 | —N(CH₃)₂ | 1 |

TABLE 18-continued

| Compound | R[6] | Position |
|---|---|---|
| 931 | 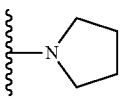 | 1 |
| 932 | 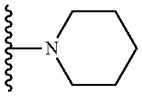 | 1 |
| 933 | 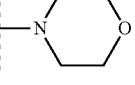 | 1 |
| 934 | —NH$_2$ | 2 |
| 935 | —NHCH$_3$ | 2 |
| 936 | —N(CH$_3$)$_2$ | 2 |
| 937 | 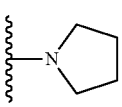 | 2 |
| 938 | 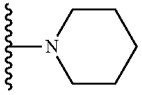 | 2 |
| 939 | 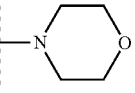 | 2 |
| 940 | —NH$_2$ | 3 |
| 941 | —NHCH$_3$ | 3 |
| 942 | —N(CH$_3$)$_2$ | 3 |
| 943 | 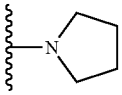 | 3 |
| 944 | 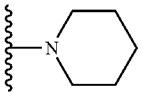 | 3 |
| 945 | 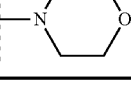 | 3 |

In certain embodiments, the present invention provides a method for the prevention or treatment of an FXR mediated disease or condition. The method comprises administering a therapeutically effective amount of a compound of Formula (I). The present invention also provides the use of a compound of Formula (I) for the preparation of a medicament for the prevention or treatment of an FXR mediated disease or condition.

In certain embodiments, the FXR-mediated disease or condition is cardiovascular disease, atherosclerosis, arteriosclerosis, hypercholesterolemia, or hyperlipidemia chronic liver disease, gastrointestinal disease, fibrotic diseases such as primary biliary cirrhosis, primary sclerosing cholangitis, pulmonary fibrosis, renal fibrosis, liver fibrosis, renal disease, metabolic disease, cancer (i.e., colorectal cancer), or neurological indications such as stroke.

In certain embodiments, the chronic liver disease is primary biliary cirrhosis (PBC), cerebrotendinous xanthomatosis (CTX), primary sclerosing cholangitis (PSC), drug induced cholestasis, intrahepatic cholestasis of pregnancy, parenteral nutrition associated cholestasis (PNAC), bacterial overgrowth or sepsis associated cholestasis, autoimmune hepatitis, chronic viral hepatitis, alcoholic liver disease, nonalcoholic fatty liver disease (NAFLD), nonalcoholic steatohepatitis (NASH), liver transplant associated graft versus host disease, living donor transplant liver regeneration, congenital hepatic fibrosis, choledocholithiasis, granulomatous liver disease, intra- or extrahepatic malignancy, Sjogren's syndrome, Sarcoidosis, Wilson's disease, Gaucher's disease, hemochromatosis, or alpha 1-antitrypsin deficiency. In certain embodiments, the gastrointestinal disease is inflammatory bowel disease (IBD) (including Crohn's disease and ulcerative colitis), irritable bowel syndrome (IBS), bacterial overgrowth, malabsorption, post-radiation colitis, or microscopic colitis.

In certain embodiments, the renal disease is diabetic nephropathy, focal segmental glomerulosclerosis (FSGS), hypertensive nephrosclerosis, chronic glomerulonephritis, chronic transplant glomerulopathy, chronic interstitial nephritis, or polycystic kidney disease.

In certain embodiments, the cardiovascular disease is atherosclerosis, arteriosclerosis, dyslipidemia, hypercholesterolemia, or hypertriglyceridemia.

In certain embodiments, the metabolic disease is insulin resistance, Type I and Type II diabetes, or obesity.

In one aspect, the compound is a selective FXR agonist over TGR5 activator.

Yet a further aspect of the present invention is a process of making any of the compounds delineated herein employing any of the synthetic means delineated herein.

Definitions

Listed below are definitions of various terms used to describe this invention. These definitions apply to the terms as they are used throughout this specification and claims, unless otherwise limited in specific instances, either individually or as part of a larger group.

The term "alkyl", as used herein, refers to a saturated, monovalent straight- or branched-chain hydrocarbon group. Preferred alkyl groups include $C_1$-$C_6$ alkyl and $C_1$-$C_8$ alkyl groups. Examples of $C_1$-$C_6$ alkyl groups include, but are not limited to, methyl, ethyl, propyl, isopropyl, n-butyl, tert-butyl, neopentyl, n-hexyl groups; and examples of $C_1$-$C_8$ alkyl groups include, but are not limited to, methyl, ethyl, propyl, isopropyl, n-butyl, tert-butyl, neopentyl, n-hexyl, heptyl, and octyl groups.

The term "alkenyl", as used herein, denote a monovalent group derived from a hydrocarbon moiety by the removal of a single hydrogen atom wherein the hydrocarbon moiety has at least one carbon-carbon double bond. Preferred alkenyl groups include $C_2$-$C_6$ alkenyl and $C_2$-$C_8$ alkenyl groups. Alkenyl groups include, but are not limited to, for example, ethenyl, propenyl, butenyl, 1-methyl-2-buten-1-yl, heptenyl, octenyl and the like.

The term "alkynyl", as used herein, denotes a monovalent group derived from a hydrocarbon moiety by the removal of a single hydrogen atom wherein the hydrocarbon moiety has at least one carbon-carbon triple bond. Preferred alkynyl groups include $C_2$-$C_6$ alkynyl and $C_2$-$C_8$ alkynyl groups. Representative alkynyl groups include, but are not limited to, for example, ethynyl, 1-propynyl, 1-butynyl, heptynyl, octynyl and the like.

The term "cycloalkyl", as used herein, denotes a monovalent group derived from a monocyclic or polycyclic saturated carbocyclic ring, wherein the said polycyclic saturated carbocyclic ring is bi or tri cyclic group fused, bridged or spiro system, and one or more carbon atoms may be optionally oxo-substituted. Preferred cycloalkyl groups include $C_3$-$C_8$ cycloalkyl and $C_3$-$C_{12}$ cycloalkyl groups. Examples of $C_3$-$C_8$-cycloalkyl include, but are not limited to, cyclopropyl, cyclobutyl, cyclopentyl, cyclohexyl, cyclopentyl and cyclooctyl; and examples of $C_3$-$C_{12}$-cycloalkyl include, but not limited to, cyclopropyl, cyclobutyl, cyclopentyl, cyclohexyl, bicyclo[2.2.1]heptyl, bicyclo[3.1.0]hexyl, spiro[2.5]octyl, spiro[4.4]nonanyl.

The term "cycloalkenyl" as used herein, denote a monovalent group derived from a monocyclic or polycyclic carbocyclic ring having at least one carbon-carbon double bond, wherein the said polycyclic cycloalkenyl ring is bi or tri cyclic group fused, bridged or spiro system, and one or more carbon atoms may be optionally oxo-substituted. Preferred cycloalkenyl groups include $C_3$-$C_8$ cycloalkenyl and $C_3$-$C_{12}$ cycloalkenyl groups. Examples of $C_3$-$C_8$-cycloalkenyl include, but are not limited to, cyclopropenyl, cyclobutenyl, cyclopentenyl, cyclohexenyl, cycloheptenyl, cyclooctenyl, and the like; and examples of $C_3$-$C_{12}$-cycloalkenyl include, but not limited to, cyclopropenyl, cyclobutenyl, cyclopentenyl, cyclohexenyl, cycloheptenyl, cyclooctenyl, cycloheptenyl, bicyclo[2.2.1]hept-2-enyl, bicyclo[3.1.0]hex-2-enyl, spiro[2.5]oct-4-enyl, spiro[4.4]non-1-enyl, and the like.

The term "aryl," as used herein, refers to a mono- or bicyclic carbocyclic ring system having one or two aromatic rings including, but not limited to, phenyl, naphthyl, tetrahydronaphthyl, indanyl, indenyl and the like.

The term "arylalkyl," as used herein, refers to a $C_1$-$C_3$ alkyl or $C_1$-$C_6$ alkyl residue attached to an aryl ring. Examples include, but are not limited to, benzyl, phenethyl and the like.

The term "heteroaryl," as used herein, refers to a mono-, bi-, or tri-cyclic aromatic radical or ring having from five to ten ring atoms of which at least one ring atom is selected from S, O and N; wherein any N or S contained within the ring may be optionally oxidized. Preferred heteroaryl groups are monocyclic or bicyclic. Heteroaryl groups include, but are not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like.

The term "heteroarylalkyl," as used herein, refers to a $C_1$-$C_3$ alkyl or $C_1$-$C_6$ alkyl residue attached to a heteroaryl ring. Examples include, but are not limited to, pyridinylmethyl, pyrimidinylethyl and the like.

The term "substituted" as used herein, refers to independent replacement of one, two, or three or more of the hydrogen atoms thereon with substituents including, but not limited to, deuterium, —F, —Cl, —Br, —I, —OH, protected hydroxy, —NO$_2$, —CN, —NH$_2$, N$_3$, protected amino, alkoxy, thioalkoxy, oxo, $C_1$-$C_{12}$-alkyl, $C_2$-$C_{12}$-alkenyl, $C_2$-$C_{12}$-alkynyl, $C_3$-$C_{12}$-cycloalkyl, -halo-$C_1$-$C_{12}$-alkyl, -halo-$C_2$-$C_{12}$-alkenyl, -halo-$C_2$-$C_{12}$-alkynyl, -halo-$C_3$-$C_{12}$-cycloalkyl, —NH—$C_1$-$C_{12}$-alkyl, —NH—$C_2$-$C_{12}$-alkenyl, —NH—$C_2$-$C_{12}$-alkynyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_{12}$-alkenyl, —O—$C_2$-$C_{12}$-alkynyl, —O—$C_3$-$C_{12}$-cycloalkyl, —O-aryl, —O-heteroaryl, —O-heterocycloalkyl, —C(O)—$C_1$-$C_{12}$-alkyl, —C(O)—$C_2$-$C_{12}$-alkenyl, —C(O)—$C_2$-$C_{12}$-alkynyl, —C(O)—$C_3$-$C_{12}$-cycloalkyl, —C(O)-aryl, —C(O)-heteroaryl, —C(O)-heterocycloalkyl, —CONH$_2$, —CONH—$C_1$-$C_{12}$-alkyl, —CONH—$C_2$-$C_{12}$-alkenyl, —CONH—$C_2$-$C_{12}$-alkynyl, —CONH—$C_3$-$C_{12}$-cycloalkyl, —CONH-aryl, —CONH-heteroaryl, —CONH-heterocycloalkyl, —OCO$_2$—$C_1$-$C_{12}$-alkyl, —OCO$_2$—$C_2$-$C_{12}$-alkenyl, —OCO$_2$—$C_2$-$C_{12}$-alkynyl, —OCO$_2$—$C_3$-$C_{12}$-cycloalkyl, —OCO$_2$-aryl, —OCO$_2$-heteroaryl, —OCO$_2$-heterocycloalkyl, —OCONH$_2$, —OCONH—$C_1$-$C_{12}$-alkyl, —OCONH—$C_2$-$C_{12}$-alkenyl, —OCONH—$C_2$-$C_{12}$-alkynyl, —OCONH—$C_3$-$C_{12}$-cycloalkyl, —OCONH-aryl, —OCONH-heteroaryl, —OCONH-heterocycloalkyl, —OCON($C_1$-$C_{12}$-alkyl)$_2$, —NHC(O)—$C_1$-$C_{12}$-alkyl, —NHC(O)—$C_2$-$C_{12}$-alkenyl, —NHC(O)—$C_2$-$C_{12}$-alkynyl, —NHC(O)—$C_3$-$C_{12}$-cycloalkyl, —NHC(O)-aryl, —NHC(O)-heteroaryl, —NHC(O)-heterocycloalkyl, —NHCO$_2$—$C_1$-$C_{12}$-alkyl, —NHCO$_2$—$C_2$-$C_{12}$-alkenyl, —NHCO$_2$—$C_2$-$C_{12}$-alkynyl, —NHCO$_2$—$C_3$-$C_{12}$-cycloalkyl, —NHCO$_2$-aryl, —NHCO$_2$-heteroaryl, —NHCO$_2$-heterocycloalkyl, —NHC(O)NH$_2$, —NHC(O)NH—$C_1$-$C_{12}$-alkyl, —NHC(O)NH—$C_2$-$C_{12}$-alkenyl, —NHC(O)NH—$C_2$-$C_{12}$-alkynyl, —NHC(O)NH—$C_3$-$C_{12}$-cycloalkyl, —NHC(O)NH-aryl, —NHC(O)NH-heteroaryl, —NHC(O)NH-heterocycloalkyl, NHC(S)NH$_2$, —NHC(S)NH—$C_1$-$C_{12}$-alkyl, —NHC(S)NH—$C_2$-$C_{12}$-alkenyl, —NHC(S)NH—$C_2$-$C_{12}$-alkynyl, —NHC(S)NH—$C_3$-$C_{12}$-cycloalkyl, —NHC(S)NH-aryl, —NHC(S)NH-heteroaryl, —NHC(S)NH-heterocycloalkyl, —NHC(NH)NH$_2$, —NHC(NH)NH—$C_1$-$C_{12}$-alkyl, —NHC(NH)NH—$C_2$-$C_{12}$-alkenyl, —NHC(NH)NH—$C_2$-$C_{12}$-alkynyl, —NHC(NH)NH—$C_3$-$C_{12}$-cycloalkyl, —NHC(NH)NH-aryl, —NHC(NH)NH-heteroaryl, —NHC(NH)NH-heterocycloalkyl, —NHC(NH)—$C_1$-$C_{12}$-alkyl, —NHC(NH)—$C_2$-$C_{12}$-alkenyl, —NHC(NH)—$C_2$-$C_{12}$-alkynyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_1$-$C_{12}$-alkyl, —C(NH)NH—$C_2$-$C_{12}$-alkenyl, —C(NH)NH—$C_2$-$C_{12}$-alkynyl, —C(NH)NH—$C_3$-$C_{12}$-cycloalkyl, —C(NH)NH-aryl, —C(NH)NH-heteroaryl, —C(NH)NH-heterocycloalkyl, —S(O)—$C_1$-$C_{12}$-alkyl, —S(O)—$C_2$-$C_{12}$-alkenyl, —S(O)—$C_2$-$C_{12}$-alkynyl, —S(O)—$C_3$-$C_{12}$-cycloalkyl, —S(O)-aryl, —S(O)-heteroaryl, —S(O)-heterocycloalkyl —SO$_2$NH$_2$, —SO$_2$NH—$C_1$-$C_{12}$-alkyl, —SO$_2$NH—$C_2$-$C_{12}$-alkenyl, —SO$_2$NH—$C_2$-$C_{12}$-alkynyl, —SO$_2$NH—$C_3$-$C_{12}$-cycloalkyl, SO$_2$NH-aryl, —SO$_2$NH-heteroaryl, —SO$_2$NH-heterocycloalkyl, —NHSO$_2$—$C_1$-$C_{12}$-alkyl, —NHSO$_2$—$C_2$-$C_{12}$-alkenyl, —NHSO$_2$—$C_2$-$C_{12}$-alkynyl, —NHSO$_2$—$C_3$-$C_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —$C_3$-$C_{12}$-cycloalkyl, polyalkoxyalkyl, polyalkoxy, -methoxymethoxy, -methoxyethoxy, —SH, —S—$C_1$-$C_{12}$-alkyl, —S—$C_2$-$C_{12}$-alkenyl, —S—$C_2$-$C_{12}$-alkynyl, —S—$C_3$-$C_{12}$-cycloalkyl, —S-aryl, —S-heteroaryl, —S-heterocycloalkyl, methylthiomethyl, or -L'-R', wherein L' is $C_1$-$C_6$ alkylene, $C_2$-$C_6$ alkenylene or $C_2$-$C_6$ alkynylene, and R' is aryl, heteroaryl, heterocyclic, $C_3$-$C_{12}$ cycloalkyl or $C_3$-$C_{12}$ cycloalkenyl. It is understood that the aryls, heteroaryls, alkyls, and the like can be further substituted. In some cases, each substituent in a substituted moiety is additionally optionally substituted with one or more groups, each group being independently selected from —F, —Cl, —Br, —I, —OH, —NO$_2$, —CN, or —NH$_2$.

In accordance with the invention, any of the aryls, substituted aryls, heteroaryls and substituted heteroaryls described herein, can be any aromatic group. Aromatic groups can be substituted or unsubstituted.

It is understood that any alkyl, alkenyl, alkynyl, cycloalkyl and cycloalkenyl moiety described herein can also be an aliphatic group, an alicyclic group or a heterocyclic group. An "aliphatic group" is non-aromatic moiety that may contain any combination of carbon atoms, hydrogen atoms, halogen atoms, oxygen, nitrogen or other atoms, and optionally contain one or more units of unsaturation, e.g., double and/or triple bonds. An aliphatic group may be straight chained, branched or cyclic and preferably contains between about 1 and about 24 carbon atoms, more typically between about 1 and about 12 carbon atoms. In addition to aliphatic hydrocarbon groups, aliphatic groups include, for example, polyalkoxyalkyls, such as polyalkylene glycols, polyamines, and polyimines, for example. Such aliphatic groups may be further substituted. It is understood that aliphatic groups may be used in place of the alkyl, alkenyl, alkynyl, alkylene, alkenylene, and alkynylene groups described herein.

The term "alicyclic," as used herein, denotes a monovalent group derived from a monocyclic or polycyclic saturated carbocyclic ring compound by the removal of a single hydrogen atom. Examples include, but are not limited to, cyclopropyl, cyclobutyl, cyclopentyl, cyclohexyl, bicyclo[2.2.1]heptyl, and bicyclo[2.2.2]octyl. Such alicyclic groups may be further substituted.

The term "heterocycloalkyl" and "heterocyclic" can be used interchangeably and refer to a non-aromatic ring or a bi- or tri-cyclic group fused, bridged, or spiro system, where: (i) each ring contains between one and three heteroatoms independently selected from oxygen, sulfur and nitrogen, (ii) each 5-membered ring has 0 to 1 double bonds and each 6-membered ring has 0 to 2 double bonds, (iii) the nitrogen and sulfur heteroatoms may optionally be oxidized, (iv) the nitrogen heteroatom may optionally be quaternized, (v) any of the above rings may be fused to a benzene ring, and (vi) the remaining ring atoms are carbon atoms which may be optionally oxo-substituted. Representative heterocycloalkyl groups include, but are not limited to, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, 2-azabicyclo[2.2.1]heptyl, 8-azabicyclo[3.2.1]octyl, 5-azaspiro[2.5]octyl, 1-oxa-7-azaspiro[4.4]nonanyl, and tetrahydrofuryl. Such heterocyclic groups may be further substituted to give substituted heterocyclic. Heteroaryl or heterocyclic groups can be C-attached or N-attached (where possible).

It will be apparent that in various embodiments of the invention, the substituted or unsubstituted alkyl, alkenyl, alkynyl, cycloalkyl, cycloalkenyl, cycloalkynyl, arylalkyl, heteroarylalkyl, and heterocycloalkyl are intended to be monovalent or divalent. Thus, alkylene, alkenylene, and alkynylene, cycloaklylene, cycloalkenylene, cycloalkynylene, arylalkylene, heteroarylalkylene and heterocycloalkylene groups are to be included in the above definitions, and are applicable to provide the Formulas herein with proper valency.

The terms "halo" and "halogen," as used herein, refer to an atom selected from fluorine, chlorine, bromine and iodine.

The term "hydrogen" includes hydrogen and deuterium. In addition, the recitation of an atom includes other isotopes of that atom so long as the resulting compound is pharmaceutically acceptable.

In certain embodiments, the compounds of each formula herein include isotopically labelled compounds. An "isotopically labelled compound" is a compound in which at least one atomic position is enriched in a specific isotope of the designated element to a level which is significantly greater than the natural abundance of that isotope. For example, one or more hydrogen atom positions in a compound can be enriched with deuterium to a level which is significantly greater than the natural abundance of deuterium, for example, enrichment to a level of at least 1%, preferably at least 20% or at least 50%. Such a deuterated compound may, for example, be metabolized more slowly than its non-deuterated analog, and therefore exhibit a longer half-life when administered to a subject. Such compounds can synthesized using methods known in the art, for example by employing deuterated starting materials. Unless stated to the contrary, isotopically labelled compounds are pharmaceutically acceptable.

When the compounds described herein contain one or more asymmetric centers they give rise to enantiomers, diastereomers, and other stereoisomeric forms that may be defined, in terms of absolute stereochemistry, as (R)— or (S)—, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques, which are known to those skilled in the art. Further details regarding resolutions can be found in Jacques, et al., *Enantiomers, Racemates, and Resolutions* (John Wiley & Sons, 1981). When the compounds described herein contain olefinic double bonds or other centers of geometric asymmetry, and unless specified otherwise, it is intended that the compounds include both E and Z geometric isomers. Likewise, all tautomeric forms are also intended to be included. The configuration of any carbon-carbon double bond appearing herein is selected for convenience only and is not intended to designate a particular configuration unless the text so states; thus a carbon-carbon double bond depicted arbitrarily herein as trans may be cis, trans, or a mixture of the two in any proportion.

The term "subject" as used herein refers to a mammal. A subject therefore refers to, for example, dogs, cats, horses, cows, pigs, guinea pigs, and the like. Preferably the subject is a human. When the subject is a human, the subject may be referred to herein as a patient. As used herein, the term "pharmaceutically acceptable salt" refers to those salts of the compounds formed by the process of the present invention which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art.

Berge, et al. describes pharmaceutically acceptable salts in detail in J. Pharmaceutical Sciences, 66: 1-19 (1977). The salts can be prepared in situ during the final isolation and purification of the compounds of the invention, or separately by reaction of the free base function with a suitable organic acid. Examples of pharmaceutically acceptable salts include, but are not limited to, nontoxic acid addition salts e.g., salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the are described generally in T. H. Greene and P. G. M. Wuts, *Protective Groups in Organic Synthesis,* 3rd edition, John Wiley & Sons, New York (1999). Examples of amino protecting groups include, but are not limited to, t-butoxycarbonyl, 9-fluorenylmethoxycarbonyl, benzyloxycarbonyl, and the like.

As used herein, the term "pharmaceutically acceptable ester" refers to esters of the compounds formed by the process of the present invention which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds formed by the process of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound, which is convertible in vivo by metabolic means (e.g. by hydrolysis) to afford any compound delineated by the Formulae of the instant invention. Various forms of prodrugs are known in the art, for example, as discussed in Bundgaard, (ed.), *Design of Prodrugs,* Elsevier (1985); Widder, et al. (ed.), *Methods in Enzymology,* Vol. 4, Academic Press (1985); Krogsgaard-Larsen, et al., (ed). "Design and Application of Prodrugs, *Textbook of Drug Design and Development,* Chapter 5, 113-191 (1991); Bundgaard, et al., *Journal of Drug Deliver Reviews,* 8:1-38(1992); Bundgaard, J. of *Pharmaceutical Sciences,* 77:285 et seq. (1988); Higuchi and Stella (eds.) Prodrugs as Novel Drug Delivery Systems, *American Chemical Society* (1975); and Bernard Testa & Joachim Mayer, "Hydrolysis In Drug And Prodrug Metabolism: Chemistry, Biochemistry And Enzymology," John Wiley and Sons, Ltd. (2002).

The term "treating", as used herein, means relieving, lessening, reducing, eliminating, modulating, or ameliorating, i.e. causing regression of the disease state or condition. Treating can also include inhibiting, i.e. arresting the development, of an existing disease state or condition, and relieving or ameliorating, i.e. causing regression of an existing disease state or condition, for example when the disease state or condition may already be present.

The term "preventing", as used herein means, to completely or almost completely stop a disease state or condition, from occurring in a patient or subject, especially when the patient or subject is predisposed to such or at risk of contracting a disease state or condition.

Additionally, the compounds of the present invention, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

"Solvates" means solvent addition forms that contain either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar to or comparable in function and appearance to the reference compound.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such solvents are well known to those skilled in the art, and individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series,* John Wiley & Sons, NY, 1986.

The terms "protogenic organic solvent" or "protic solvent" as used herein, refer to a solvent that tends to provide protons, such as an alcohol, for example, methanol, ethanol, propanol, isopropanol, butanol, t-butanol, and the like. Such solvents are well known to those skilled in the art, and individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series,* John Wiley & Sons, NY, 1986.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. Additionally, the various synthetic steps may be performed in an alternate sequence or order to give the desired compounds. In addition, the solvents, temperatures, reaction durations, etc. delineated herein are for purposes of illustration only and variation of the reaction conditions can produce the desired isoxazole products of the present invention. Synthetic chemistry transformations and protecting group methodologies (protection and deprotection) useful in synthesizing the compounds described herein include, for example, those described in R. Larock, *Comprehensive Organic Transformations,* VCH Publishers (1989); T. W. Greene and P. G. M. Wuts, *Protective Groups in Organic Synthesis,* 2d. Ed., John Wiley and Sons (1991); L. Fieser and M. Fieser, *Fieser and Fieser's Reagents for Organic Synthesis,* John Wiley and Sons (1994); and L. Paquette, ed., *Encyclopedia of Reagents for Organic Synthesis,* John Wiley and Sons (1995).

The compounds of this invention may be modified by appending various functionalities via synthetic means delineated herein to enhance selective biological properties. Such modifications include those which increase biological penetration into a given biological system (e.g., blood, lymphatic system, central nervous system), increase oral availability, increase solubility to allow administration by injection, alter metabolism and alter rate of excretion.

Pharmaceutical Compositions

The pharmaceutical compositions of the present invention comprise a therapeutically effective amount of a compound of the present invention Formulated together with one or more pharmaceutically acceptable carriers. As used herein, the term "pharmaceutically acceptable carrier" means a non-toxic, inert solid, semi-solid or liquid filler, diluent, encapsulating material or Formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the Formulator. The pharmaceutical compositions of this invention can be administered to humans and other animals orally, rectally, parenterally, intracisternally, intravaginally, intraperitoneally, topically (as by powders, ointments, or drops), buccally, or as an oral or nasal spray.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the Formulation may be adjusted with pharmaceutically acceptable acids, bases or buffers to enhance the stability of the Formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable Formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable Formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragées, capsules, pills, and granules can be prepared with coatings and shells such as enteric coatings, release controlling coatings and other coatings well known in the pharmaceutical Formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic Formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Unless otherwise defined, all technical and scientific terms used herein are accorded the meaning commonly known to one with ordinary skill in the art. All publications, patents, published patent applications, and other references mentioned herein are hereby incorporated by reference in their entirety.

Abbreviations

Abbreviations which have been used in the descriptions of the schemes and the examples that follow are:
BOP-Cl for bis(2-oxo-3-oxazolidinyl)phosphinic chloride;
CDI for carbonyldiimidazole;
DBU for 1,8-diazabicycloundec-7-ene;
DCC for N,N'-dicyclohexylcarbodiimide;
DCM for dichloromethane;
DMAP for N,N-dimethylaminopyridine;
DMF for N,N-dimethyl formamide;
DPPA for diphenylphosphoryl azide;
EDC for 1-(3-diethylaminopropyl)-3-ethylcarbodiimide hydrochloride;
$Et_3N$ for triethylamine;
EtOAc for ethyl acetate;
HATU for 1-[bis(dimethylamino)methylene]-1H-1,2,3-triazolo[4,5-b]pyridinium 3-oxidhexafluorophosphate;
HCl for hydrochloric acid;
PyAOP for 7-azabenzotriazol-1-yloxy)tripyrrolidinophosphonium hexafluorophosphate;
PyBOP for benzotriazol-1-yl-oxytripyrrolidinophosphonium hexafluorophosphate;
TFFH for tetramethylfluoroformamidinium hexafluorophosphate;
THF for tetrahydrofuran.

Synthetic Methods

The compounds and processes of the present invention will be better understood in connection with the following synthetic schemes that illustrate the methods by which the compounds of the invention may be prepared, which are intended as an illustration only and not to limit the scope of the invention. Various changes and modifications to the disclosed embodiments will be apparent to those skilled in the art and such changes and modifications including, without limitation, those relating to the chemical structures, substituents, derivatives, and/or methods of the invention may be made without departing from the spirit of the invention and the scope of the appended claims.

As shown in Scheme 1, novel isoxazole sulfonyl urea analogs of the compound of Formula (1-3) are prepared from the compound of Formula (1-1), wherein $R^1$, $R^2$, $X^1$, $X^2$, $X^3$, $X^4$ Y, n, and

are as previously defined. For the preparation of carboxylic acids of Formula (1-1), see WO 2009/005998. Thus, the compound of Formula (1-1) is converted to the acyl azide compound of Formula (1-2) using a suitable reagent such as, but not limited to, DPPA. The reaction solvent can be, but not limited to, THF, DCM and toluene. The preferred solvent is Toluene. The reaction temperature is from −20° C. to 90° C. Further Curtius rearrangement of the compound of Formula (1-2) at elevated temperature and reacting with a sulfonamide affords the compound of Formula (1-3), wherein $R^1$, $R^2$, $X^1$, $X^2$, $X^3$, $X^4$, n,

and $R^6$ are as previously defined. A more detailed discussion of the procedures, reagents and conditions for Curtius rearrangement is described in literature, for example, by Jerry March in "Advanced Organic Chemistry" 4$^{th}$ ed., John Wiley & Son, Inc., 1992.

Scheme 1

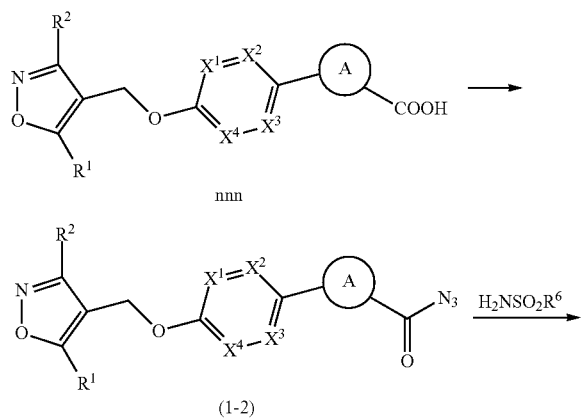

-continued

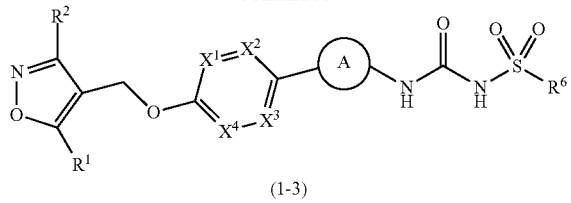

(1-3)

As shown in Scheme 2, novel isoxazole acylsulfonamide analogs of the compound of Formula (2-1) are prepared from the compound of Formula (1-1), wherein $R^1$, $R^2$, $X^1$, $X^2$, $X^3$, $X^4$, Y, and

are as previously defined. The compound of Formula (1-1) is coupled with a sulfonamide using suitable coupling conditions to give the compound of Formula (2-1), wherein $R^1$, $R^2$, $X^1$, $X^2$, $X^3$, $X^4$, Y,

and $R^6$ are as previously defined. The coupling reagent can be selected from, but not limited to, DCC, EDC, CDI, diisopropyl carbodiimide, BOP-Cl, PyBOP, PyAOP, TFFH and HATU. Suitable bases include, but are not limited to, triethylamine, diisopropylethylamine, DBU, N-methylmorpholine and DMAP. The coupling reaction is carried out in an aprotic solvent such as, but not limited to, DCM, DMF or THF. The reaction temperature can vary from 0° C. to about 50° C.

Scheme 2

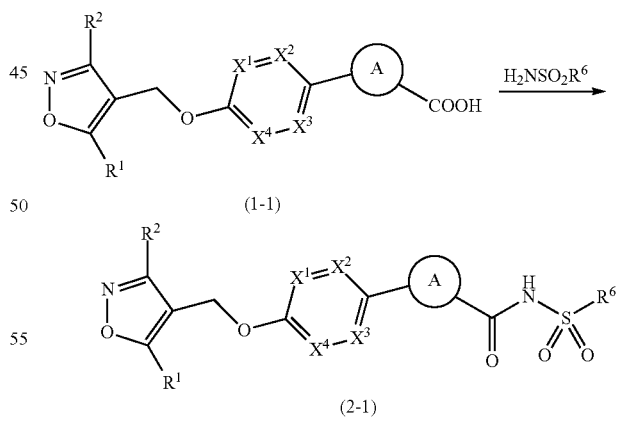

EXAMPLES

The compounds and processes of the present invention will be better understood in connection with the following examples, which are intended as an illustration only and not limiting of the scope of the invention. Various changes and modifications to the disclosed embodiments will be apparent

Example 11

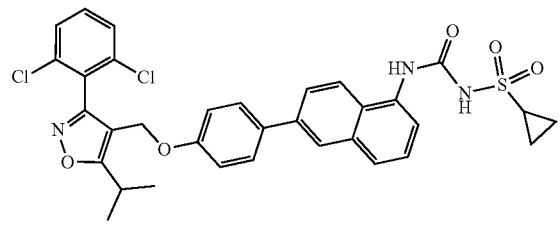 [SMILES: CC(C)c1onc(-c2c(Cl)cccc2Cl)c1COc1ccc(-c2ccc3c(NC(=O)NS(=O)(=O)C4CC4)cccc3c2)cc1]

Step 1-1:

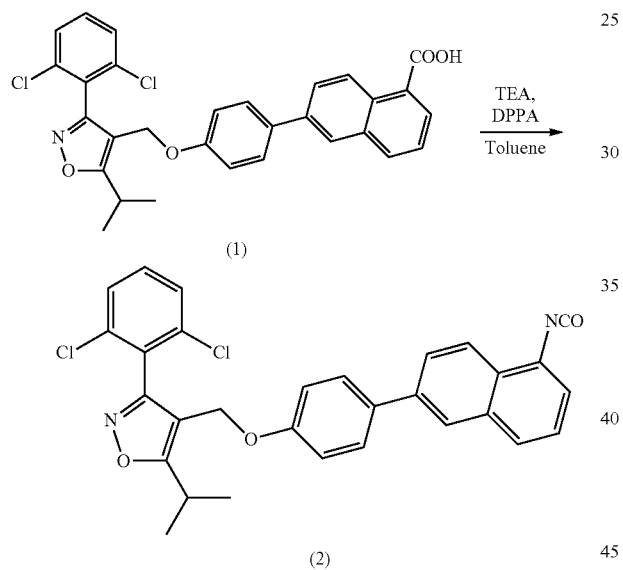

To a solution of carboxylic acid (1) (93.6 mg, 0.176 mmol) in Toluene (1.758 ml) and triethylamine (49.0 μl, 0.352 mmol) was added diphenyl phosphorazidate (41.7 μl, 0.193 mmol). The mixture was stirred at RT for 1 h, then at 85° C. for 3 h. The solution was cooled to RT, divided into 3 portions with 0.06 mmol isocyanate (2) per portions, used for step (1-2).

Step 1-2:

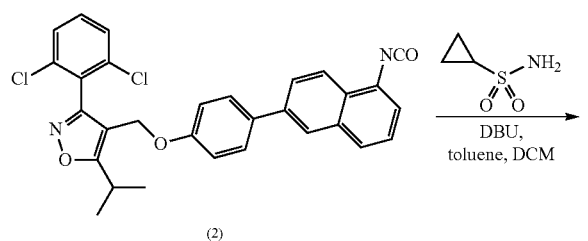

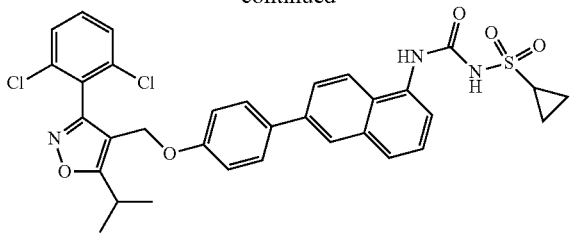

example 11

To a solution of isocyanate (2) (31.8 mg, 0.06 mmol) in Toluene (0.6 ml) was added cyclopropanesulfonamide (8.00 mg, 0.066 mmol), DBU (9.95 μl, 0.066 mmol) and $CH_2Cl_2$ (0.3 ml). The resulting mixture was stirred at 23° C. for 15 h, quenched with 1 M HCl and extracted with EtOAc. The combined organic layers were dried over $Na_2SO_4$, conc. in vacuo, and purified on prep. HPLC to give example 11 (23 mg).

Examples 16 were prepared using the same procedure as the one used in example 11.

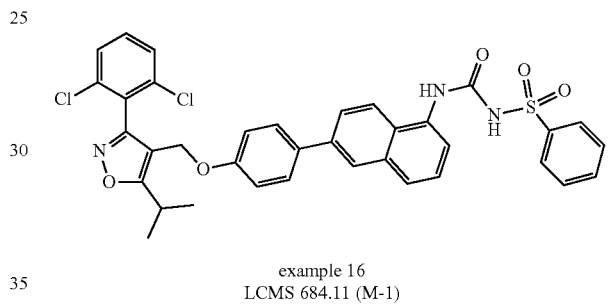

example 16
LCMS 684.11 (M-1)

Example 90

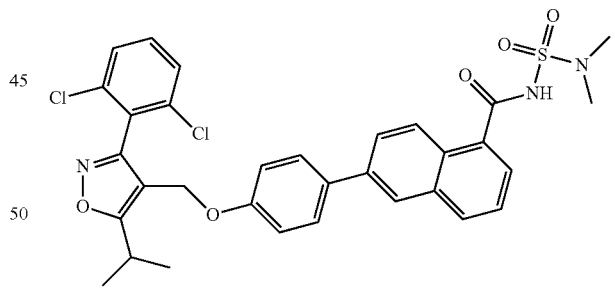

Step 2-1:

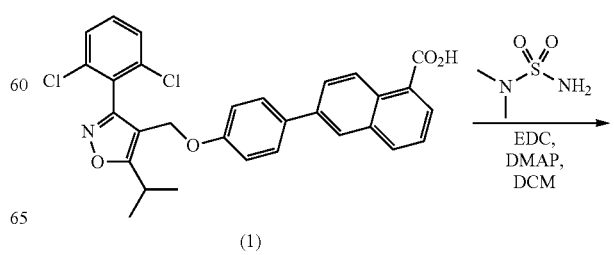

81

-continued

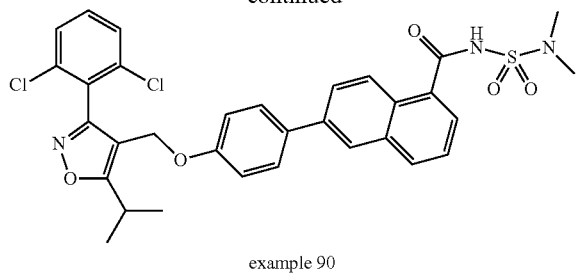

example 90

A solution of acid (1) (53 mg, 0.100 mmol), N,N-Dimethylsulfamide (24.72 mg, 0.199 mmol), EDC (38.2 mg, 0.2 mmol), and DMAP (24.32 mg, 0.20 mmol) in DCM (2 ml) was stirred at RT for 16 h, then quenched with brine, and extracted with EtOAc. The combined organic layers were washed with brine and concentrated. The residue was purified by chromatography on silica gel using hexane/acetone (100/0 to 60/40, 10 min) to give example 90 as a white solid (26 mg).

Assays

Human FXR (NR1H4) Assay

Determination of a ligand mediated Gal4 promoter driven transactivation to quantify ligand binding mediated activation of FXR. FXR Reporter Assay kit purchased from Indigo Bioscience (Catalogue number: IB00601) to determine the potency and efficacy of compound developed by Enanta that can induce FXR activation. The principle application of this reporter assay system is to quantify functional activity of human FXR. The assay utilizes non-human mammalian cells, CHO (Chinese hamster ovary) cells engineered to express human NR1H4 protein (referred to as FXR). Reporter cells also incorporate the cDNA encoding beetle luciferase which catalyzes the substrates and yields photon emission. Luminescence intensity of the reaction is quantified using a plate-reading luminometer, Envision. Reporter Cells include the luciferase reporter gene functionally linked to an FXR responsive promoter. Thus, quantifying changes in luciferase expression in the treated reporter cells provides a sensitive surrogate measure of the changes in FXR activity. $EC_{50}$ and efficacy (normalize to CDCA set as 100%) is determined by XLFit. The assay is according to the manufacturer's instructions. In brief, the assay was performed in white, 96 well plates using final volume of 100 µl containing cells with different doses of compounds. Retrieve Reporter Cells from −80° C. storage. Perform a rapid thaw of the frozen cells by transferring a 10 ml volume of 37° C. cell recovery medium into the tube of frozen cells. Recap the tube of Reporter Cells and immediately place it in a 37° C. water bath for 5-10 minutes. Retrieve the tube of Reporter Cell Suspension from the water bath. Sanitize the outside surface of the tube with a 70% alcohol swab, and then transfer it into the cell culture hood. Dispense 90 µl of cell suspension into each well of the 96-well Assay Plate. Transfer the plate into 37° C. incubator, allowing the cells adherent to the bottom of the well. Dilute compounds in Dilution Plate (DP), and administrate to cells at Assay Plate (AP). DMSO content of the samples was kept at 0.2%. Cells were incubated for additional 22 hours before luciferase activities were measured. Thirty minutes before intending to quantify FXR activity, remove Detection Substrate and Detection Buffer from the refrigerator and place them in a low-light area so that they may equilibrate to room tem-

82 perature. Remove the plate's lid and discard all media contents by ejecting it into an appropriate waste container. Gently tap the inverted plate onto a clean absorbent paper towel to remove residual droplets. Cells will remain tightly adhered to well bottoms. Add 100 µl of luciferase detection reagent to each well of the assay plate. Allow the assay plate to rest at room temperature for at least 5 minutes following the addition of LDR. Set the instrument (Envision) to perform a single 5 second "plate shake" prior to reading the first assay well. Read time may be 0.5 second (500 mSec) per well. $EC_{50}$ and Efficacy (normalize to CDCA set as 100%) is determined by XLFit.

To assess the FXR agonistic potency of the example compounds as well as for the reference compound (1), potency ranges were determined in the Human FXR (NR1H4) Assay as listed below in Table 7. The efficacy was normalized to CDCA set as 100%. (A=$EC_{50}$<0.1 µM; B=0.1 µM<$EC_{50}$<1.0 µM; C=1.0 µM<$EC_{50}$<10 µM; D=$EC_{50}$>10 µM)

TABLE 7

| Example | EC50 (µM) | Efficacy (%) |
|---|---|---|
| CDCA | D | 100 |
| Compound (1) | B | 220 |
| 11 | B | 1.2 |
| 16 | B | 117 |
| 90 | B | 1.3 |

While this invention has been particularly shown and described with references to preferred embodiments thereof, it will be understood by those skilled in the art that various changes in form and details may be made therein without departing from the scope of the invention encompassed by the appended claims.

What is claimed:
1. A compound represented by Formula I, or a pharmaceutically acceptable salt thereof:

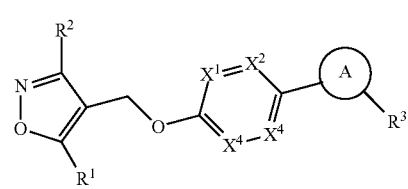

(I)

wherein:
R[1] is hydrogen, halogen, cyano, optionally substituted $C_1$-$C_6$ alkyl, optionally substituted $C_2$-$C_6$ alkenyl, optionally substituted $C_2$-$C_6$ alkynyl, optionally substituted $C_3$-$C_6$ cycloalkyl or optionally substituted 3- to 6-membered heterocycloalkyl;

R[2] is an optionally substituted aryl, optionally substituted heteroaryl, optionally substituted arylalkyl or optionally substituted heteroarylalkyl;

$X^1$, $X^2$, $X^3$, and $X^4$ are independently selected from N and C(Y); wherein Y is selected from hydrogen, halo, cyano, $C_1$-$C_6$ alkyl, $C_2$-$C_6$ alkenyl, $C_2$-$C_6$ alkynyl, $C_3$-$C_6$ cycloalkyl, heterocycloalkyl, haloalkyl, alkoxy, and haloalkoxy;

is aryl, heterocyclic, heteroaryl, bicyclic fused arylheterocyclic or bicyclic fused heteroarylheterocyclic, wherein said aryl, heterocyclic, heteroaryl, bicyclic fused arylheterocyclic or bicyclic fused heteroarylheterocyclic is optionally substituted with one or two substituents independently selected from optionally substituted —$C_1$-$C_8$ alkyl, halo, and halo-$C_1$-$C_8$-alkyl; or

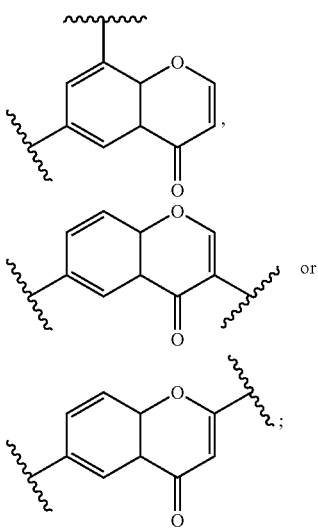

is $R^3$ is

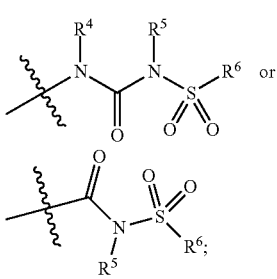

$R^4$ and $R^5$ are independently selected from the group consisting of:
1) Hydrogen;
2) Optionally substituted —$C_1$-$C_8$ alkyl;
3) Optionally substituted —$C_2$-$C_8$ alkenyl;
4) Optionally substituted —$C_2$-$C_8$ alkynyl; and
5) Optionally substituted —$C_3$-$C_8$ cycloalkyl;

$R^6$ is selected from the group consisting of:
1) Optionally substituted —$C_1$-$C_8$ alkyl;
2) Optionally substituted —$C_2$-$C_8$ alkenyl;
3) Optionally substituted —$C_2$-$C_8$ alkynyl;
4) Optionally substituted —$C_3$-$C_8$ cycloalkyl;
5) Optionally substituted aryl;
6) Optionally substituted arylalkyl;
7) Optionally substituted 3- to 8-membered heterocycloalkyl;

8) Optionally substituted heteroaryl;
9) Optionally substituted heteroarylalkyl; and
10) $NR^7R^8$; wherein $R^7$ and $R^8$ are each independently selected from hydrogen, optionally substituted —$C_1$-$C_8$ alkyl, optionally substituted —$C_2$-$C_8$ alkenyl, optionally substituted —$C_2$-$C_8$ alkynyl, optionally substituted —$C_3$-$C_8$ cycloalkyl, optionally substituted aryl, optionally substituted arylalkyl, optionally substituted 3- to 8-membered heterocycloalkyl, optionally substituted heteroaryl, and optionally substituted heteroarylalkyl, or $R^7$ and $R^8$ are taken together with the nitrogen atom which they are attached to form an optionally substituted heterocyclic ring; provided that when $R_3$ is

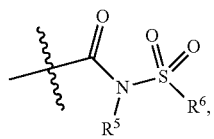

$R^6$ is $NR^7R^8$.

2. The compound of claim 1, represented by Formula II or III or a pharmaceutically acceptable salt thereof:

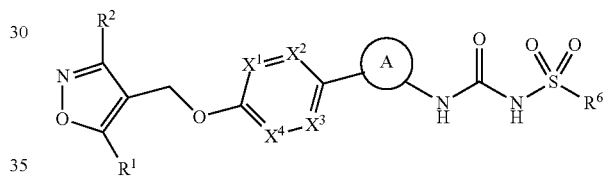

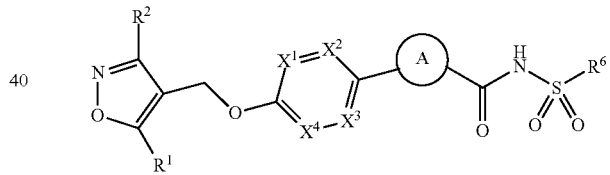

wherein $R^1$, $R^2$, $X^1$, $X^2$, $X^3$, $X^4$, (A)

and $R^6$ are as defined in claim 1.

3. The compound of claim 1, represented by Formula IV or V or a pharmaceutically acceptable salt thereof:

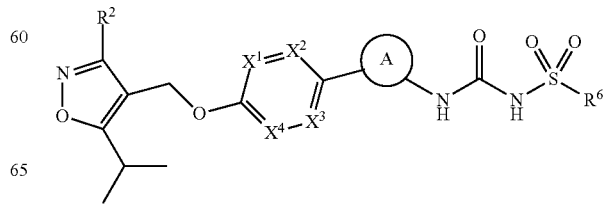

-continued (V)

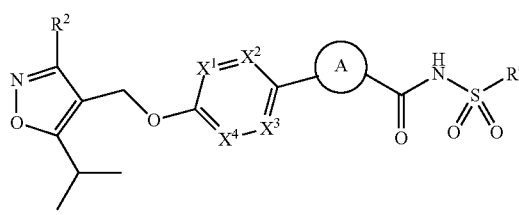

wherein $R^2$, $X^1$, $X^2$, $X^3$, $X^4$,

, and $R^6$ are as defined in claim 1.

4. The compound of claim 1, represented by Formula VI or VII or a pharmaceutically acceptable salt thereof:

(VI)

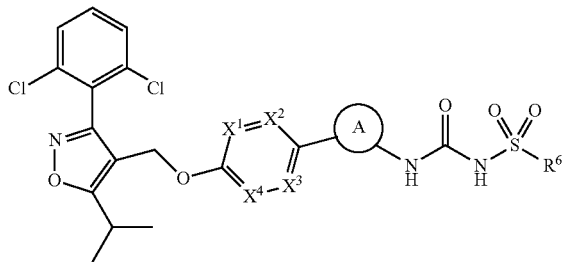

wherein $X^1$, $X^2$, $X^3$, $X^4$,

, and $R^6$ are as defined in claim 1.

5. The compound of claim 1, represented by Formula VIII or IX or a pharmaceutically acceptable salt thereof:

(VII)

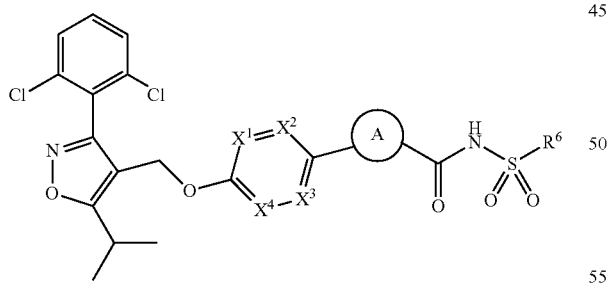

(VIII)

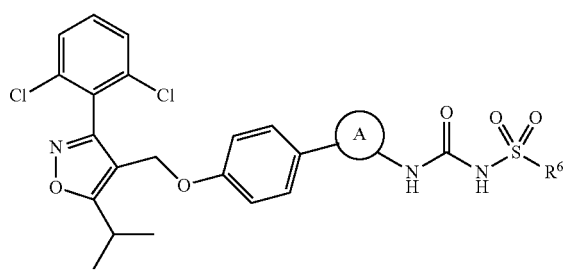

(IX)

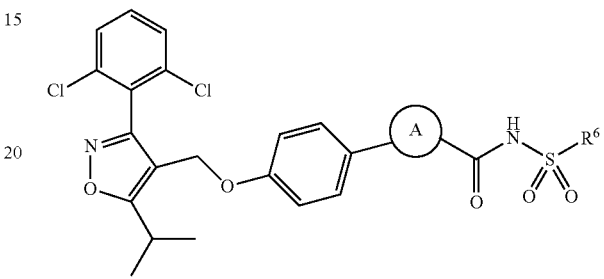

wherein

and $R^6$ are as defined in claim 1.

6. The compound of claim 1, which is selected from
(a) compounds of Formula (X), (X)

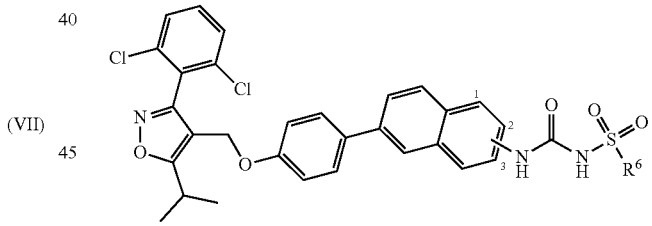

and pharmaceutically acceptable salts thereof, wherein $R^6$ and the substitution position of the —NHC(O)NHS(O)$_2$R$^6$ group are delineated for each compound in Table 1,

TABLE 1

| Compound | $R^6$ | Position |
|---|---|---|
| 1 | Methyl | 1 |
| 2 | Ethyl | 1 |
| 3 | Isopropyl | 1 |
| 4 | Butyl | 1 |
| 5 | t-Butyl | 1 |
| 6 | Propyl | 1 |
| 7 | Benzyl | 1 |
| 8 | Vinyl | 1 |
| 9 | Allyl | 1 |
| 10 | —CF$_3$ | 1 |

TABLE 1-continued
| Compound | R⁶ | Position |
|---|---|---|
| 11 |  | 1 |
| 12 |  | 1 |
| 13 | 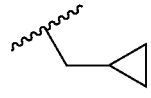 [SMILES: *CC1CC1] | 1 |
| 14 | 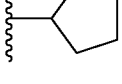 | 1 |
| 15 | 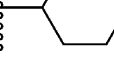 | 1 |
| 16 | 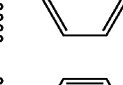 | 1 |
| 17 | 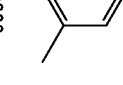 | 1 |
| 18 | 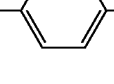 | 1 |
| 19 | 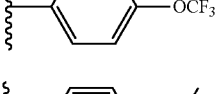 | 1 |
| 20 | 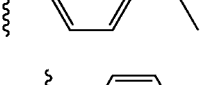 | 1 |
| 21 | 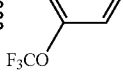 | 1 |
| 22 | 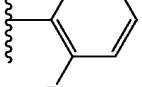 | 1 |
| 23 | 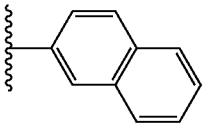 | 1 |
TABLE 1-continued
| Compound | R⁶ | Position |
|---|---|---|
| 24 | —NH$_2$ | 1 |
| 25 | —NHCH$_3$ | 1 |
| 26 | —N(CH$_3$)$_2$ | 1 |
| 27 | 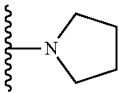 | 1 |
| 28 | 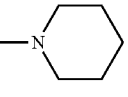 | 1 |
| 29 | 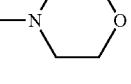 | 1 |
| 30 | Methyl | 2 |
| 31 | Ethyl | 2 |
| 32 | Isopropyl | 2 |
| 33 | Butyl | 2 |
| 34 | t-Butyl | 2 |
| 35 | Propyl | 2 |
| 36 | Benzyl | 2 |
| 37 | Vinyl | 2 |
| 38 | Allyl | 2 |
| 39 | —CF$_3$ | 2 |
| 40 | 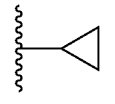 [SMILES: *C1CC1] | 2 |
| 41 | 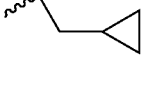 | 2 |
| 42 |  | 2 |
| 43 | 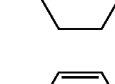 | 2 |
| 44 | 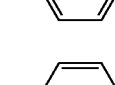 | 2 |
| 45 | 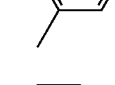 | 2 |
| 46 | 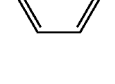 | 2 |
| 47 |  | 2 |

TABLE 1-continued

| Compound | R⁶ | Position |
|---|---|---|
| 48 | 4-OCF₃-phenyl | 2 |
| 49 | 4-t-butyl-phenyl | 2 |
| 50 | 2-CF₃-phenyl (F₃C) | 2 |
| 51 | 2-F-phenyl | 2 |
| 52 | naphthalen-2-yl | 2 |
| 53 | —NH₂ | 2 |
| 54 | —NHCH₃ | 2 |
| 55 | —N(CH₃)₂ | 2 |
| 56 | pyrrolidin-1-yl | 2 |
| 57 | piperidin-1-yl | 2 |
| 58 | morpholin-4-yl | 2 |
| 59 | Methyl | 3 |
| 60 | Ethyl | 3 |
| 61 | Isopropyl | 3 |
| 62 | Butyl | 3 |
| 63 | t-Butyl | 3 |
| 64 | Propyl | 3 |
| 65 | Benzyl | 3 |
| 66 | Vinyl | 3 |
| 67 | Allyl | 3 |
| 68 | —CF₃ | 3 |
| 69 | cyclopropyl | 3 |
| 70 | 1-methylcyclopropyl | 3 |
| 71 | cyclopropylmethyl | 3 |
| 72 | cyclopentyl | 3 |
| 73 | cyclohexyl | 3 |
| 74 | phenyl | 3 |
| 75 | 2-methylphenyl | 3 |
| 76 | 4-methylphenyl | 3 |
| 77 | 4-OCF₃-phenyl | 3 |
| 78 | 4-t-butyl-phenyl | 3 |
| 79 | 2-CF₃-phenyl (F₃C) | 3 |
| 80 | 2-F-phenyl | 3 |
| 81 | naphthalen-2-yl | 3 |
| 82 | —NH₂ | 3 |
| 83 | —NHCH₃ | 3 |
| 84 | —N(CH₃)₂ | 3 |
| 85 | pyrrolidin-1-yl | 3 |

TABLE 1-continued

| Compound | R⁶ | Position |
|---|---|---|
| 86 | 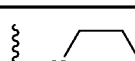 (piperidinyl) | 3 |
| 87 | 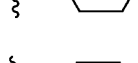 (morpholinyl) | 3 | and
(b) compounds of Formula (XI),

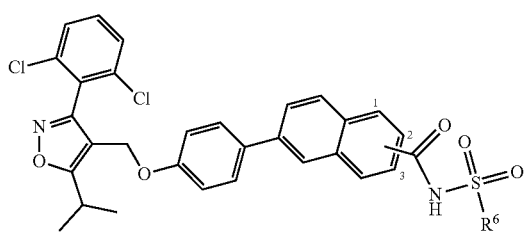

(XI)

and pharmaceutically acceptable salts thereof, wherein R⁶ and the substitution position of the —C(O)NHS(O)₂R⁶ group are delineated for each compound in Table 2,

TABLE 2

| Compound | R⁶ | Position |
|---|---|---|
| 88 | —NH₂ | 1 |
| 89 | —NHCH₃ | 1 |
| 90 | —N(CH₃)₂ | 1 |
| 91 | 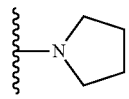 (pyrrolidinyl) | 1 |
| 92 | 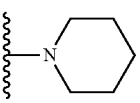 (piperidinyl) | 1 |
| 93 | 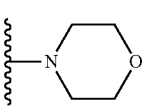 (morpholinyl) | 1 |
| 94 | —NH₂ | 2 |
| 95 | —NHCH₃ | 2 |
| 96 | —N(CH₃)₂ | 2 |
| 97 | 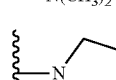 (pyrrolidinyl) | 2 |
| 98 | 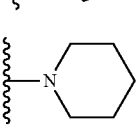 (piperidinyl) | 2 |

TABLE 2-continued

| Compound | R⁶ | Position |
|---|---|---|
| 99 | 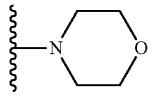 (morpholinyl) | 2 |
| 100 | —NH₂ | 3 |
| 101 | —NHCH₃ | 3 |
| 102 | —N(CH₃)₂ | 3 |
| 103 | 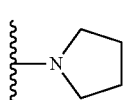 (pyrrolidinyl) | 3 |
| 104 | 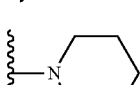 (piperidinyl) | 3 |
| 105 | 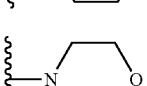 (morpholinyl) | 3. |

7. The compound of claim 1, which is selected from (a) compounds of Formula (XII),

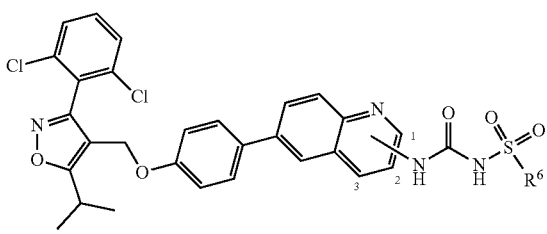

(XII)

and pharmaceutically acceptable salts thereof, wherein R⁶ and the substitution position of the —NHC(O)NHS(O)₂R⁶ group are delineated for each compound in Table 3,

TABLE 3

| Compound | R⁶ | Position |
|---|---|---|
| 106 | Methyl | 1 |
| 107 | Ethyl | 1 |
| 108 | Isopropyl | 1 |
| 109 | Butyl | 1 |
| 110 | t-Butyl | 1 |
| 111 | Propyl | 1 |
| 112 | Benzyl | 1 |
| 113 | Vinyl | 1 |
| 114 | Allyl | 1 |
| 115 | —CF₃ | 1 |
| 116 |  (cyclopropyl) | 1 |
| 117 |  (methylcyclopropyl) | 1 |

TABLE 3-continued
| Compound | R⁶ | Position |
|---|---|---|
| 118 | 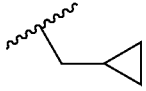 [SMILES: *CC1CC1] | 1 |
| 119 | 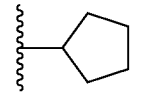 [SMILES: *C1CCCC1] | 1 |
| 120 | 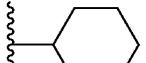 | 1 |
| 121 | 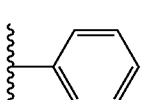 | 1 |
| 122 | 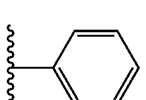 | 1 |
| 123 | 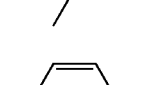 | 1 |
| 124 | 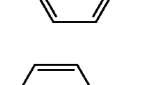 | 1 |
| 125 | 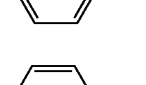 | 1 |
| 126 | 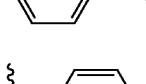 | 1 |
| 127 | 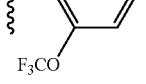 | 1 |
| 128 | 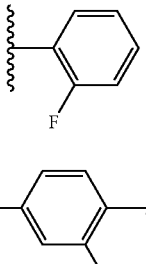 | 1 |
| 129 | —NH₂ | 1 |
| 130 | —NHCH₃ | 1 |
| 131 | —N(CH₃)₂ | 1 |
| 132 | 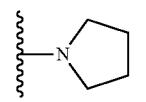 | 1 |
| 133 | 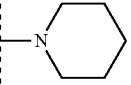 | 1 |
| 134 | 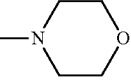 | 1 |
| 135 | Methyl | 2 |
| 136 | Ethyl | 2 |
| 137 | Isopropyl | 2 |
| 138 | Butyl | 2 |
| 139 | t-Butyl | 2 |
| 140 | Propyl | 2 |
| 141 | Benzyl | 2 |
| 142 | Vinyl | 2 |
| 143 | Allyl | 2 |
| 144 | —CF₃ | 2 |
| 145 | 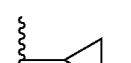 | 2 |
| 146 | 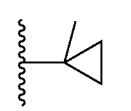 | 2 |
| 147 |  | 2 |
| 148 | 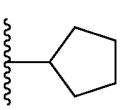 | 2 |
| 149 | 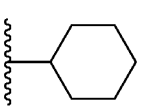 | 2 |
| 150 | 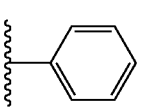 | 2 |
| 151 | 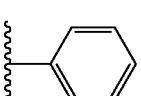 | 2 |
| 152 | 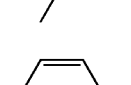 | 2 |
| 153 | 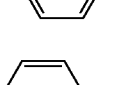 | 2 |
| 154 | 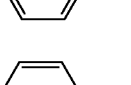 | 2 |

TABLE 3-continued

| Compound | R⁶ | Position |
|---|---|---|
| 155 | 2-(F₃CO)phenyl | 2 |
| 156 | 2-fluorophenyl | 2 |
| 157 | naphthalen-2-yl | 2 |
| 158 | —NH₂ | 2 |
| 159 | —NHCH₃ | 2 |
| 160 | —N(CH₃)₂ | 2 |
| 161 | pyrrolidin-1-yl | 2 |
| 162 | piperidin-1-yl | 2 |
| 163 | morpholin-4-yl | 2 |
| 164 | Methyl | 3 |
| 165 | Ethyl | 3 |
| 166 | Isopropyl | 3 |
| 167 | Butyl | 3 |
| 168 | t-Butyl | 3 |
| 169 | Propyl | 3 |
| 170 | Benzyl | 3 |
| 171 | Vinyl | 3 |
| 172 | Allyl | 3 |
| 173 | —CF₃ | 3 |
| 174 | cyclopropyl | 3 |
| 175 | 1-methylcyclopropyl | 3 |
| 176 | cyclopropylmethyl | 3 |
| 177 | cyclopentyl | 3 |
| 178 | cyclohexyl | 3 |
| 179 | phenyl | 3 |
| 180 | 2-methylphenyl | 3 |
| 181 | 4-methylphenyl | 3 |
| 182 | 4-(OCF₃)phenyl | 3 |
| 183 | 4-t-butylphenyl | 3 |
| 184 | 2-(F₃CO)phenyl | 3 |
| 185 | 2-fluorophenyl | 3 |
| 186 | naphthalen-2-yl | 3 |
| 187 | —NH₂ | 3 |
| 188 | —NHCH₃ | 3 |
| 189 | —N(CH₃)₂ | 3 |
| 190 | pyrrolidin-1-yl | 3 |
| 191 | piperidin-1-yl | 3 |
| 192 | morpholin-4-yl | 3 | and (b) compounds of Formula (XIII),

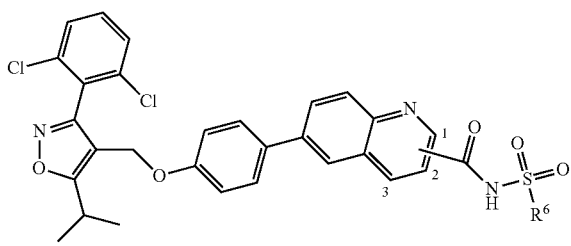

(XIII)

and pharmaceutically acceptable salts thereof, wherein $R^6$ and the substitution position of the —C(O)NHS(O)$_2$R$^6$ group are delineated for each compound in Table 4,

TABLE 4

| Compound | R$^6$ | Position |
|---|---|---|
| 193 | —NH$_2$ | 1 |
| 194 | —NHCH$_3$ | 1 |
| 195 | —N(CH$_3$)$_2$ | 1 |
| 196 | pyrrolidinyl | 1 |
| 197 | piperidinyl | 1 |
| 198 | morpholinyl | 1 |
| 199 | —NH$_2$ | 2 |
| 200 | —NHCH$_3$ | 2 |
| 201 | —N(CH$_3$)$_2$ | 2 |
| 202 | pyrrolidinyl | 2 |
| 203 | piperidinyl | 2 |
| 204 | morpholinyl | 2 |
| 205 | —NH$_2$ | 3 |
| 206 | —NHCH$_3$ | 3 |
| 207 | —N(CH$_3$)$_2$ | 3 |
| 208 | pyrrolidinyl | 3 |

TABLE 4-continued

| Compound | R$^6$ | Position |
|---|---|---|
| 209 | piperidinyl | 3 |
| 210 | morpholinyl | 3. |

8. The compound of claim 1, which is selected from (a) compounds of Formula (XIV),

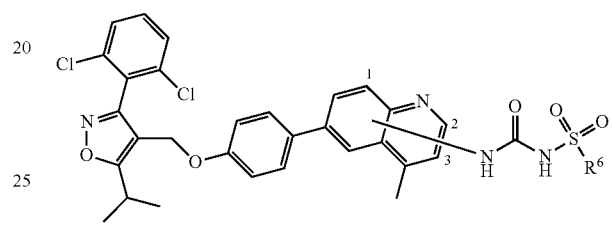

(XIV)

and pharmaceutically acceptable salts thereof, wherein $R^6$ and the substitution position of the —NHC(O)NHS(O)$_2$R$^6$ group are delineated for each compound in Table 5,

TABLE 5

| Compound | R$^6$ | Position |
|---|---|---|
| 211 | Methyl | 1 |
| 212 | Ethyl | 1 |
| 213 | Isopropyl | 1 |
| 214 | Butyl | 1 |
| 215 | t-Butyl | 1 |
| 216 | Propyl | 1 |
| 217 | Benzyl | 1 |
| 218 | Vinyl | 1 |
| 219 | Allyl | 1 |
| 220 | —CF$_3$ | 1 |
| 221 | cyclopropyl | 1 |
| 222 | cyclopropyl | 1 |
| 223 | cyclopropylmethyl | 1 |
| 224 | cyclopentyl | 1 |
| 225 | cyclohexyl | 1 |

TABLE 5-continued

| Compound | R⁶ | Position |
|---|---|---|
| 226 | 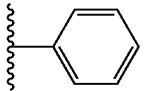 phenyl | 1 |
| 227 | 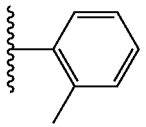 [SMILES: *c1ccccc1C] 2-methylphenyl | 1 |
| 228 | 4-methylphenyl | 1 |
| 229 | 4-OCF₃-phenyl | 1 |
| 230 | 4-t-butylphenyl | 1 |
| 231 | 2-OCF₃-phenyl (F₃CO) | 1 |
| 232 | 2-F-phenyl | 1 |
| 233 |  naphthyl | 1 |
| 234 | —NH₂ | 1 |
| 235 | —NHCH₃ | 1 |
| 236 | —N(CH₃)₂ | 1 |
| 237 | 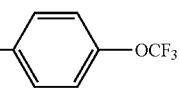 pyrrolidinyl | 1 |
| 238 | 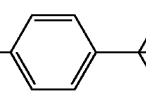 piperidinyl | 1 |
| 239 | 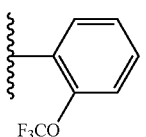 morpholinyl | 1 |
| 240 | Methyl | 2 |
| 241 | Ethyl | 2 |
| 242 | Isopropyl | 2 |
| 243 | Butyl | 2 |
| 244 | t-Butyl | 2 |
| 245 | Propyl | 2 |
| 246 | Benzyl | 2 |
| 247 | Vinyl | 2 |
| 248 | Allyl | 2 |
| 249 | —CF₃ | 2 |
| 250 | 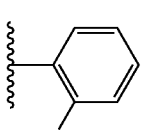 cyclopropyl | 2 |
| 251 | methylcyclopropyl | 2 |
| 252 | cyclopropylmethyl | 2 |
| 253 | 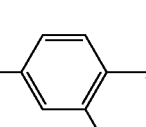 cyclopentyl | 2 |
| 254 | 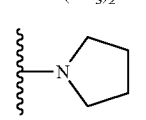 cyclohexyl | 2 |
| 255 | phenyl | 2 |
| 256 | 2-methylphenyl | 2 |
| 257 | 4-methylphenyl | 2 |
| 258 | 4-OCF₃-phenyl | 2 |
| 259 | 4-t-butylphenyl | 2 |
| 260 | 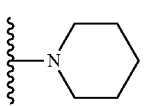 2-OCF₃-phenyl | 2 |
| 261 | 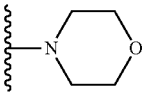 2-F-phenyl | 2 |

TABLE 5-continued

| Compound | R⁶ | Position |
|---|---|---|
| 262 | 2-naphthyl | 2 |
| 263 | —NH₂ | 2 |
| 264 | —NHCH₃ | 2 |
| 265 | —N(CH₃)₂ | 2 |
| 266 | pyrrolidin-1-yl | 2 |
| 267 | piperidin-1-yl | 2 |
| 268 | morpholin-4-yl | 2 |
| 269 | Methyl | 3 |
| 270 | Ethyl | 3 |
| 271 | Isopropyl | 3 |
| 272 | Butyl | 3 |
| 273 | t-Butyl | 3 |
| 274 | Propyl | 3 |
| 275 | Benzyl | 3 |
| 276 | Vinyl | 3 |
| 277 | Allyl | 3 |
| 278 | —CF₃ | 3 |
| 279 | cyclopropyl | 3 |
| 280 | 1-methylcyclopropyl | 3 |
| 281 | cyclopropylmethyl | 3 |
| 282 | cyclopentyl | 3 |
| 283 | cyclohexyl | 3 |
| 284 | phenyl | 3 |
| 285 | 3-methylphenyl | 3 |

TABLE 5-continued

| Compound | R⁶ | Position |
|---|---|---|
| 286 | 4-methylphenyl | 3 |
| 287 | 4-trifluoromethoxyphenyl | 3 |
| 288 | 4-t-butylphenyl | 3 |
| 289 | 2-trifluoromethoxyphenyl | 3 |
| 290 | 2-fluorophenyl | 3 |
| 291 | 2-naphthyl | 3 |
| 292 | —NH₂ | 3 |
| 293 | —NHCH₃ | 3 |
| 294 | —N(CH₃)₂ | 3 |
| 295 | pyrrolidin-1-yl | 3 |
| 296 | piperidin-1-yl | 3 |
| 297 | morpholin-4-yl | 3 | and
(b) compounds of Formula (XV), (XV)

and pharmaceutically acceptable salts thereof, wherein $R^6$ and the substitution position of the —C(O)NHS(O)$_2$R$^6$ group are delineated for each compound in Table 6,

TABLE 6

| Compound | R$^6$ | Position |
|---|---|---|
| 298 | —NH$_2$ | 1 |
| 299 | —NHCH$_3$ | 1 |
| 300 | —N(CH$_3$)$_2$ | 1 |
| 301 | pyrrolidinyl | 1 |
| 302 | piperidinyl | 1 |
| 303 | morpholinyl | 1 |
| 304 | —NH$_2$ | 2 |
| 305 | —NHCH$_3$ | 2 |
| 306 | —N(CH$_3$)$_2$ | 2 |
| 307 | pyrrolidinyl | 2 |
| 308 | piperidinyl | 2 |
| 309 | morpholinyl | 2 |
| 310 | —NH$_2$ | 3 |
| 311 | —NHCH$_3$ | 3 |
| 312 | —N(CH$_3$)$_2$ | 3 |
| 313 | pyrrolidinyl | 3 |
| 314 | piperidinyl | 3 |
| 315 | morpholinyl | 3. |

9. The compound of claim 1, which is selected from (a) compounds of Formula (XVI),

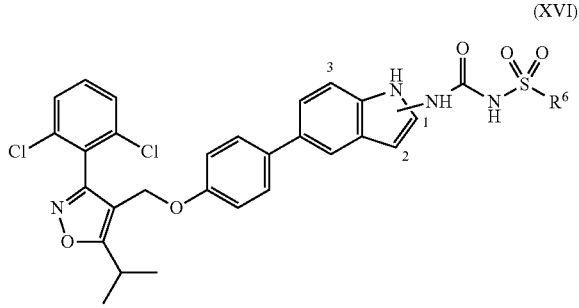

(XVI)

and pharmaceutically acceptable salts thereof, wherein $R^6$ and the substitution position of the —NHC(O)NHS(O)$_2$R$^6$ group are delineated for each compound in Table 7,

TABLE 7

| Compound | R$^6$ | Position |
|---|---|---|
| 316 | Methyl | 1 |
| 317 | Ethyl | 1 |
| 318 | Isopropyl | 1 |
| 319 | Butyl | 1 |
| 320 | t-Butyl | 1 |
| 321 | Propyl | 1 |
| 322 | Benzyl | 1 |
| 323 | Vinyl | 1 |
| 324 | Allyl | 1 |
| 325 | —CF$_3$ | 1 |
| 326 | cyclopropyl | 1 |
| 327 | cyclopropyl | 1 |
| 328 | cyclopropylmethyl | 1 |
| 329 | cyclopentyl | 1 |
| 330 | cyclohexyl | 1 |
| 331 | phenyl | 1 |
| 332 | o-tolyl | 1 |
| 333 | p-tolyl | 1 |

TABLE 7-continued

| Compound | R⁶ | Position |
|---|---|---|
| 334 | 4-(OCF₃)-phenyl | 1 |
| 335 | 4-(t-Bu)-phenyl | 1 |
| 336 | 2-(OCF₃)-phenyl | 1 |
| 337 | 2-F-phenyl | 1 |
| 338 | 2-naphthyl | 1 |
| 339 | —NH₂ | 1 |
| 340 | —NHCH₃ | 1 |
| 341 | —N(CH₃)₂ | 1 |
| 342 | pyrrolidin-1-yl | 1 |
| 343 | piperidin-1-yl | 1 |
| 344 | morpholin-4-yl | 1 |
| 345 | Methyl | 2 |
| 346 | Ethyl | 2 |
| 347 | Isopropyl | 2 |
| 348 | Butyl | 2 |
| 349 | t-Butyl | 2 |
| 350 | Propyl | 2 |
| 351 | Benzyl | 2 |
| 352 | Vinyl | 2 |
| 353 | Allyl | 2 |
| 354 | —CF₃ | 2 |
| 355 | cyclopropyl | 2 |
| 356 | cyclopropyl | 2 |
| 357 | cyclopropylmethyl | 2 |
| 358 | cyclopentyl | 2 |
| 359 | cyclohexyl | 2 |
| 360 | phenyl | 2 |
| 361 | 2-methylphenyl | 2 |
| 362 | 4-methylphenyl | 2 |
| 363 | 4-(OCF₃)-phenyl | 2 |
| 364 | 4-(t-Bu)-phenyl | 2 |
| 365 | 2-(OCF₃)-phenyl | 2 |
| 366 | 2-F-phenyl | 2 |
| 367 | 2-naphthyl | 2 |
| 368 | —NH₂ | 2 |
| 369 | —NHCH₃ | 2 |
| 370 | —N(CH₃)₂ | 2 |
| 371 | pyrrolidin-1-yl | 2 |

TABLE 7-continued

| Compound | R⁶ | Position |
|---|---|---|
| 372 | 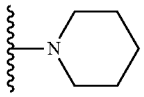 (piperidinyl-N) | 2 |
| 373 | 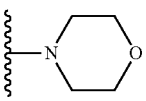 (morpholinyl-N) | 2 |
| 374 | Methyl | 3 |
| 375 | Ethyl | 3 |
| 376 | Isopropyl | 3 |
| 377 | Butyl | 3 |
| 378 | t-Butyl | 3 |
| 379 | Propyl | 3 |
| 380 | Benzyl | 3 |
| 381 | Vinyl | 3 |
| 382 | Allyl | 3 |
| 383 | —CF₃ | 3 |
| 384 | 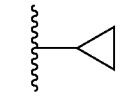 [SMILES: *C1CC1] (cyclopropyl) | 3 |
| 385 | 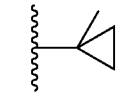 [SMILES: *C1(C)CC1] (cyclopropyl) | 3 |
| 386 |  (cyclopropylmethyl) | 3 |
| 387 | 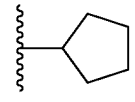 (cyclopentyl) | 3 |
| 388 | 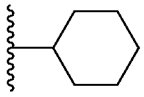 (cyclohexyl) | 3 |
| 389 | 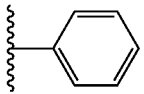 (phenyl) | 3 |
| 390 | 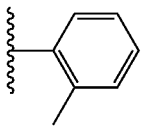 [SMILES: *c1ccccc1C] (o-tolyl) | 3 |
| 391 | 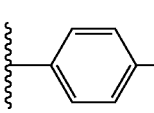 (p-tolyl) | 3 |
| 392 | 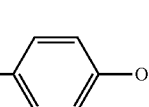 (4-OCF₃-phenyl) | 3 |
| 393 | 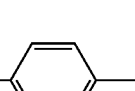 (4-t-butyl-phenyl) | 3 |
| 394 | 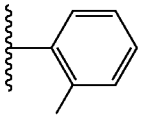 (2-OCF₃-phenyl) | 3 |
| 395 | 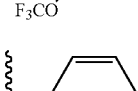 (2-F-phenyl) | 3 |
| 396 | 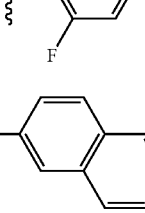 (naphthyl) | 3 |
| 397 | —NH₂ | 3 |
| 398 | —NHCH₃ | 3 |
| 399 | —N(CH₃)₂ | 3 |
| 400 | 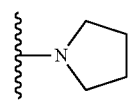 (pyrrolidinyl-N) | 3 |
| 401 | 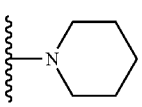 (piperidinyl-N) | 3 |
| 402 | 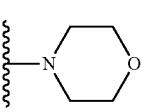 (morpholinyl-N) | 3 | and
(b) compounds of Formula (XVII),

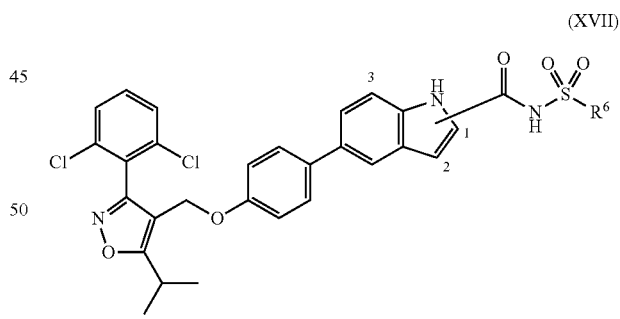

(XVII)

and pharmaceutically acceptable salts thereof, wherein R⁶ and the substitution position of the —C(O)NHS(O)₂R⁶ group are delineated for each compound in Table 8,

TABLE 8

| Compound | R⁶ | Position |
|---|---|---|
| 403 | —NH₂ | 1 |
| 404 | —NHCH₃ | 1 |
| 405 | —N(CH₃)₂ | 1 |

TABLE 8-continued

| Compound | R⁶ | Position |
|---|---|---|
| 406 | pyrrolidinyl (N-linked) | 1 |
| 407 | piperidinyl (N-linked) | 1 |
| 408 | morpholinyl (N-linked) | 1 |
| 409 | —NH₂ | 2 |
| 410 | —NHCH₃ | 2 |
| 411 | —N(CH₃)₂ | 2 |
| 412 | pyrrolidinyl (N-linked) | 2 |
| 413 | piperidinyl (N-linked) | 2 |
| 414 | morpholinyl (N-linked) | 2 |
| 415 | —NH₂ | 3 |
| 416 | —NHCH₃ | 3 |
| 417 | —N(CH₃)₂ | 3 |
| 418 | pyrrolidinyl (N-linked) | 3 |
| 419 | piperidinyl (N-linked) | 3 |
| 420 | morpholinyl (N-linked) | 3. |

10. The compound of claim 1, which is selected from
(a) compounds of Formula (XVIII),

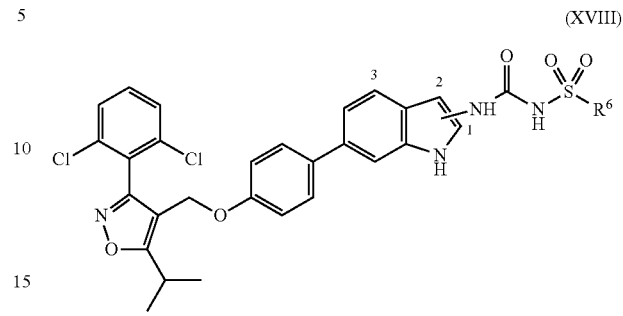

and pharmaceutically acceptable salts thereof, wherein R⁶ and the substitution position of the —NHC(O)NHS(O)₂R⁶ group are delineated for each compound in Table 9,

TABLE 9

| Compound | R⁶ | Position |
|---|---|---|
| 421 | Methyl | 1 |
| 422 | Ethyl | 1 |
| 423 | Isopropyl | 1 |
| 424 | Butyl | 1 |
| 425 | t-Butyl | 1 |
| 426 | Propyl | 1 |
| 427 | Benzyl | 1 |
| 428 | Vinyl | 1 |
| 429 | Allyl | 1 |
| 430 | —CF₃ | 1 |
| 431 | cyclopropyl | 1 |
| 432 | cyclopropyl | 1 |
| 433 | cyclopropylmethyl | 1 |
| 434 | cyclopentyl | 1 |
| 435 | cyclohexyl | 1 |
| 436 | phenyl | 1 |
| 437 | m-tolyl | 1 |

TABLE 9-continued

| Compound | R⁶ | Position |
|---|---|---|
| 438 | 4-methylphenyl | 1 |
| 439 | 4-OCF₃-phenyl | 1 |
| 440 | 4-t-butylphenyl | 1 |
| 441 | 2-OCF₃-phenyl | 1 |
| 442 | 2-fluorophenyl | 1 |
| 443 | 2-naphthyl | 1 |
| 444 | —NH₂ | 1 |
| 445 | —NHCH₃ | 1 |
| 446 | —N(CH₃)₂ | 1 |
| 447 | pyrrolidin-1-yl | 1 |
| 448 | piperidin-1-yl | 1 |
| 449 | morpholin-4-yl | 1 |
| 450 | Methyl | 2 |
| 451 | Ethyl | 2 |
| 452 | Isopropyl | 2 |
| 453 | Butyl | 2 |
| 454 | t-Butyl | 2 |
| 455 | Propyl | 2 |
| 456 | Benzyl | 2 |
| 457 | Vinyl | 2 |
| 458 | Allyl | 2 |
| 459 | —CF₃ | 2 |
| 460 | cyclopropyl | 2 |
| 461 | 1-methylcyclopropyl | 2 |
| 462 | cyclopropylmethyl | 2 |
| 463 | cyclopentyl | 2 |
| 464 | cyclohexyl | 2 |
| 465 | phenyl | 2 |
| 466 | 2-methylphenyl | 2 |
| 467 | 4-methylphenyl | 2 |
| 468 | 4-OCF₃-phenyl | 2 |
| 469 | 4-t-butylphenyl | 2 |
| 470 | 2-OCF₃-phenyl | 2 |
| 471 | 2-fluorophenyl | 2 |
| 472 | 2-naphthyl | 2 |
| 473 | —NH₂ | 2 |
| 474 | —NHCH₃ | 2 |
| 475 | —N(CH₃)₂ | 2 |

TABLE 9-continued
| Compound | R⁶ | Position |
|---|---|---|
| 476 | 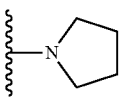 | 2 |
| 477 | 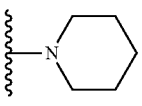 | 2 |
| 478 | 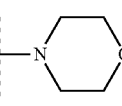 | 2 |
| 479 | Methyl | 3 |
| 480 | Ethyl | 3 |
| 481 | Isopropyl | 3 |
| 482 | Butyl | 3 |
| 483 | t-Butyl | 3 |
| 484 | Propyl | 3 |
| 485 | Benzyl | 3 |
| 486 | Vinyl | 3 |
| 487 | Allyl | 3 |
| 488 | —CF₃ | 3 |
| 489 | 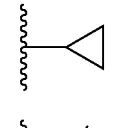 | 3 |
| 490 | 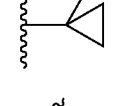 | 3 |
| 491 | 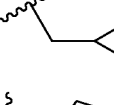 | 3 |
| 492 | 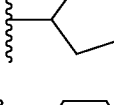 | 3 |
| 493 | 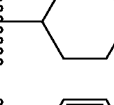 | 3 |
| 494 | 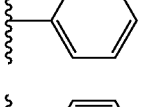 | 3 |
| 495 | 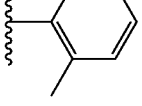 | 3 |
| 496 | 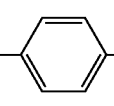 | 3 |
| 497 | 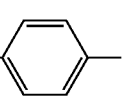 | 3 |
| 498 | 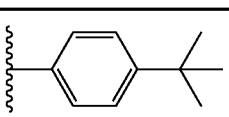 | 3 |
| 499 | 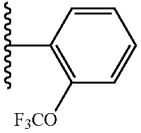 | 3 |
| 500 | 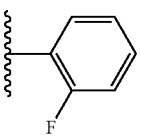 [SMILES: *c1ccccc1F] | 3 |
| 501 | 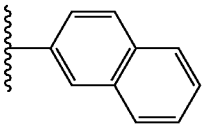 [SMILES: *c1ccc2ccccc2c1] | 3 |
| 502 | —NH₂ | 3 |
| 503 | —NHCH₃ | 3 |
| 504 | —N(CH₃)₂ | 3 |
| 505 | 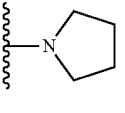 [SMILES: *N1CCCC1] | 3 |
| 506 | 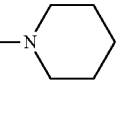 | 3 |
| 507 | 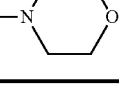 | 3 |
and
(b) compounds of Formula (XIX),
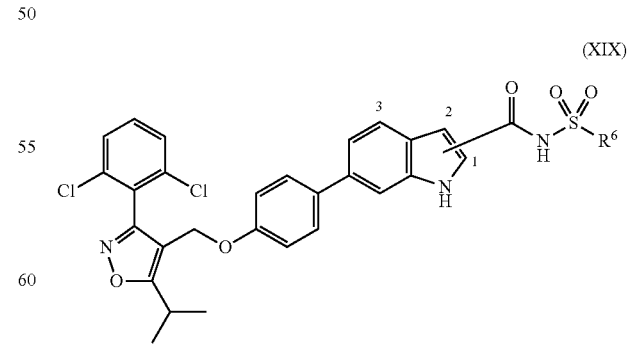
(XIX)
and pharmaceutically acceptable salts thereof, wherein R⁶ and the substitution position of the —C(O)NHS(O)₂R⁶ group are delineated for each compound in Table 10,

TABLE 10

| Compound | R⁶ | Position |
|---|---|---|
| 508 | —NH₂ | 1 |
| 509 | —NHCH₃ | 1 |
| 510 | —N(CH₃)₂ | 1 |
| 511 | 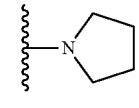 | 1 |
| 512 | 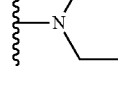 | 1 |
| 513 | 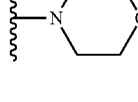 | 1 |
| 514 | —NH₂ | 2 |
| 515 | —NHCH₃ | 2 |
| 516 | —N(CH₃)₂ | 2 |
| 517 | 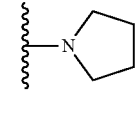 | 2 |
| 518 |  | 2 |
| 519 | 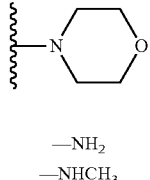 | 2 |
| 520 | —NH₂ | 3 |
| 521 | —NHCH₃ | 3 |
| 522 | —N(CH₃)₂ | 3 |
| 523 | 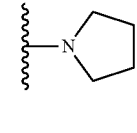 | 3 |
| 524 |  | 3 |
| 525 |  | 3. |

11. The compound of claim 1, which is selected from (a) compounds of Formula (XX),

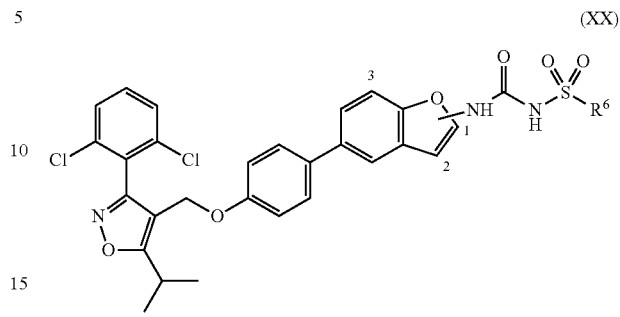

and pharmaceutically acceptable salts thereof, wherein R⁶ and the substitution position of the —NHC(O)NHS(O)₂R⁶ group are delineated for each compound in Table 11,

TABLE 11

| Compound | R⁶ | Position |
|---|---|---|
| 526 | Methyl | 1 |
| 527 | Ethyl | 1 |
| 528 | Isopropyl | 1 |
| 529 | Butyl | 1 |
| 530 | t-Butyl | 1 |
| 531 | Propyl | 1 |
| 532 | Benzyl | 1 |
| 533 | Vinyl | 1 |
| 534 | Allyl | 1 |
| 535 | —CF₃ | 1 |
| 536 |  | 1 |
| 537 |  | 1 |
| 538 | 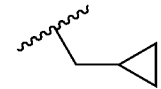 | 1 |
| 539 | 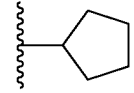 | 1 |
| 540 | 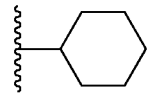 [SMILES: *C1CCCCC1] | 1 |
| 541 | 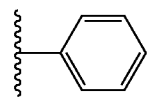 | 1 |
| 542 | 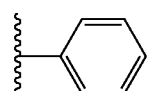 | 1 |

TABLE 11-continued

| Compound | R⁶ | Position |
|---|---|---|
| 543 | 4-methylphenyl | 1 |
| 544 | 4-(OCF₃)phenyl | 1 |
| 545 | 4-(t-butyl)phenyl | 1 |
| 546 | 2-(OCF₃)phenyl | 1 |
| 547 | 2-fluorophenyl | 1 |
| 548 | naphthalen-2-yl | 1 |
| 549 | —NH₂ | 1 |
| 550 | —NHCH₃ | 1 |
| 551 | —N(CH₃)₂ | 1 |
| 552 | pyrrolidin-1-yl | 1 |
| 553 | piperidin-1-yl | 1 |
| 554 | morpholin-4-yl | 1 |
| 555 | Methyl | 2 |
| 556 | Ethyl | 2 |
| 557 | Isopropyl | 2 |
| 558 | Butyl | 2 |
| 559 | t-Butyl | 2 |
| 560 | Propyl | 2 |
| 561 | Benzyl | 2 |
| 562 | Vinyl | 2 |
| 563 | Allyl | 2 |
| 564 | —CF₃ | 2 |
| 565 | cyclopropyl | 2 |
| 566 | 1-methylcyclopropyl | 2 |
| 567 | cyclopropylmethyl | 2 |
| 568 | cyclopentyl | 2 |
| 569 | cyclohexyl | 2 |
| 570 | phenyl | 2 |
| 571 | 2-methylphenyl | 2 |
| 572 | 4-methylphenyl | 2 |
| 573 | 4-(OCF₃)phenyl | 2 |
| 574 | 4-(t-butyl)phenyl | 2 |
| 575 | 2-(OCF₃)phenyl | 2 |
| 576 | 2-fluorophenyl | 2 |
| 577 | naphthalen-2-yl | 2 |
| 578 | —NH₂ | 2 |
| 579 | —NHCH₃ | 2 |
| 580 | —N(CH₃)₂ | 2 |

TABLE 11-continued

| Compound | R⁶ | Position |
|---|---|---|
| 581 | pyrrolidinyl (N-linked) | 2 |
| 582 | piperidinyl (N-linked) | 2 |
| 583 | morpholinyl (N-linked) | 2 |
| 584 | Methyl | 3 |
| 585 | Ethyl | 3 |
| 586 | Isopropyl | 3 |
| 587 | Butyl | 3 |
| 588 | t-Butyl | 3 |
| 589 | Propyl | 3 |
| 590 | Benzyl | 3 |
| 591 | Vinyl | 3 |
| 592 | Allyl | 3 |
| 593 | —CF₃ | 3 |
| 594 | cyclopropyl | 3 |
| 595 | 1-methylcyclopropyl | 3 |
| 596 | cyclopropylmethyl | 3 |
| 597 | cyclopentyl | 3 |
| 598 | cyclohexyl | 3 |
| 599 | phenyl | 3 |
| 600 | 2-methylphenyl | 3 |
| 601 | 4-methylphenyl | 3 |
| 602 | 4-(OCF₃)phenyl | 3 |
| 603 | 4-t-butylphenyl | 3 |
| 604 | 2-(OCF₃)phenyl | 3 |
| 605 | 2-fluorophenyl | 3 |
| 606 | 2-naphthyl | 3 |
| 607 | —NH₂ | 3 |
| 608 | —NHCH₃ | 3 |
| 609 | —N(CH₃)₂ | 3 |
| 610 | pyrrolidinyl (N-linked) | 3 |
| 611 | piperidinyl (N-linked) | 3 |
| 612 | morpholinyl (N-linked) | 3 | and (b) compounds of Formula (XXI),

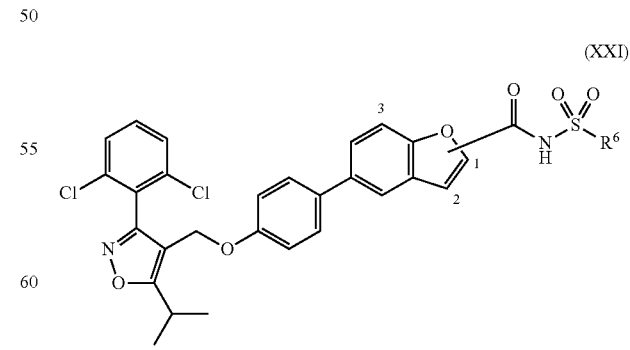

and pharmaceutically acceptable salts thereof, wherein R⁶ and the substitution position of the —C(O)NHS(O)₂R⁶ group are delineated for each compound in Table 12,

TABLE 12

| Compound | R⁶ | Position |
|---|---|---|
| 613 | —NH₂ | 1 |
| 614 | —NHCH₃ | 1 |
| 615 | —N(CH₃)₂ | 1 |
| 616 | pyrrolidinyl | 1 |
| 617 | piperidinyl | 1 |
| 618 | morpholinyl | 1 |
| 619 | —NH₂ | 2 |
| 620 | —NHCH₃ | 2 |
| 621 | —N(CH₃)₂ | 2 |
| 622 | pyrrolidinyl | 2 |
| 623 | piperidinyl | 2 |
| 624 | morpholinyl | 2 |
| 625 | —NH₂ | 3 |
| 626 | —NHCH₃ | 3 |
| 627 | —N(CH₃)₂ | 3 |
| 628 | pyrrolidinyl | 3 |
| 629 | piperidinyl | 3 |
| 630 | morpholinyl | 3 |

12. The compound of claim 1, which is selected from (a) compounds of Formula (XXII),

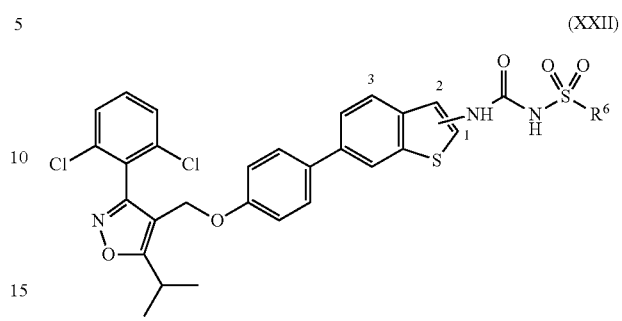

and pharmaceutically acceptable salts thereof, wherein R⁶ and the substitution position of the —NHC(O)NHS(O)₂R⁶ group are delineated for each compound in Table 13,

TABLE 13

| Compound | R⁶ | Position |
|---|---|---|
| 631 | Methyl | 1 |
| 632 | Ethyl | 1 |
| 633 | Isopropyl | 1 |
| 634 | Butyl | 1 |
| 635 | t-Butyl | 1 |
| 636 | Propyl | 1 |
| 637 | Benzyl | 1 |
| 638 | Vinyl | 1 |
| 639 | Allyl | 1 |
| 640 | —CF₃ | 1 |
| 641 | cyclopropyl | 1 |
| 642 | methylcyclopropyl | 1 |
| 643 | cyclopropylmethyl | 1 |
| 644 | cyclopentyl | 1 |
| 645 | cyclohexyl | 1 |
| 646 | phenyl | 1 |
| 647 | methylphenyl | 1 |

TABLE 13-continued

| Compound | R⁶ | Position |
|---|---|---|
| 648 | 4-methylphenyl | 1 |
| 649 | 4-(OCF₃)phenyl | 1 |
| 650 | 4-t-butylphenyl | 1 |
| 651 | 2-(OCF₃)phenyl (F₃CO) | 1 |
| 652 | 2-fluorophenyl | 1 |
| 653 | naphthalen-2-yl | 1 |
| 654 | —NH₂ | 1 |
| 655 | —NHCH₃ | 1 |
| 656 | —N(CH₃)₂ | 1 |
| 657 | pyrrolidin-1-yl | 1 |
| 658 | piperidin-1-yl | 1 |
| 659 | morpholin-4-yl | 1 |
| 660 | Methyl | 2 |
| 661 | Ethyl | 2 |
| 662 | Isopropyl | 2 |
| 663 | Butyl | 2 |
| 664 | t-Butyl | 2 |
| 665 | Propyl | 2 |
| 666 | Benzyl | 2 |
| 667 | Vinyl | 2 |
| 668 | Allyl | 2 |
| 669 | —CF₃ | 2 |
| 670 | cyclopropyl | 2 |
| 671 | 1-methylcyclopropyl | 2 |
| 672 | cyclopropylmethyl | 2 |
| 673 | cyclopentyl | 2 |
| 674 | cyclohexyl | 2 |
| 675 | phenyl | 2 |
| 676 | 2-methylphenyl | 2 |
| 677 | 4-methylphenyl | 2 |
| 678 | 4-(OCF₃)phenyl | 2 |
| 679 | 4-t-butylphenyl | 2 |
| 680 | 2-(OCF₃)phenyl (F₃CO) | 2 |
| 681 | 2-fluorophenyl | 2 |
| 682 | naphthalen-2-yl | 2 |
| 683 | —NH₂ | 2 |
| 684 | —NHCH₃ | 2 |
| 685 | —N(CH₃)₂ | 2 |

TABLE 13-continued
| Compound | R⁶ | Position |
|---|---|---|
| 686 | 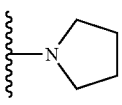 [SMILES: *N1CCCC1] pyrrolidin-1-yl | 2 |
| 687 | 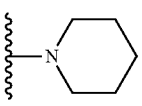 piperidin-1-yl | 2 |
| 688 | 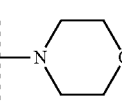 morpholin-4-yl | 2 |
| 689 | Methyl | 3 |
| 690 | Ethyl | 3 |
| 691 | Isopropyl | 3 |
| 692 | Butyl | 3 |
| 693 | t-Butyl | 3 |
| 694 | Propyl | 3 |
| 695 | Benzyl | 3 |
| 696 | Vinyl | 3 |
| 697 | Allyl | 3 |
| 698 | —CF₃ | 3 |
| 699 | 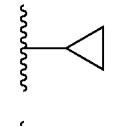 | 3 |
| 700 | 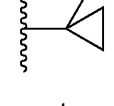 | 3 |
| 701 | 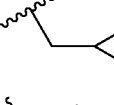 | 3 |
| 702 | 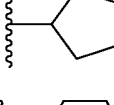 | 3 |
| 703 | 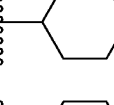 | 3 |
| 704 | 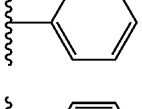 | 3 |
| 705 | 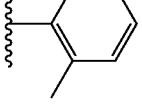 | 3 |
| 706 | 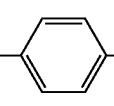 | 3 |
| 707 | 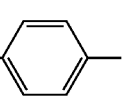 | 3 |
| 708 | 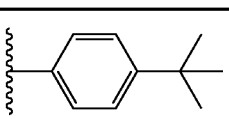 | 3 |
| 709 | 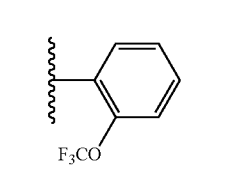 [SMILES: *c1ccccc1OC(F)(F)F] | 3 |
| 710 | 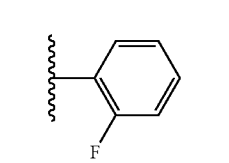 [SMILES: *c1ccccc1F] | 3 |
| 711 | 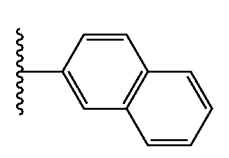 [SMILES: *c1ccc2ccccc2c1] | 3 |
| 712 | —NH₂ | 3 |
| 713 | —NHCH₃ | 3 |
| 714 | —N(CH₃)₂ | 3 |
| 715 | 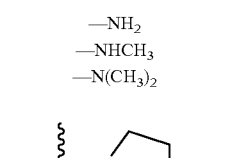 | 3 |
| 716 | 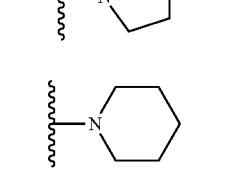 | 3 |
| 717 | 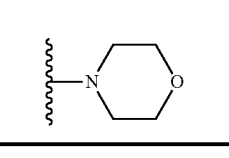 | 3 |
and
(b) compounds of Formula (XXIII),
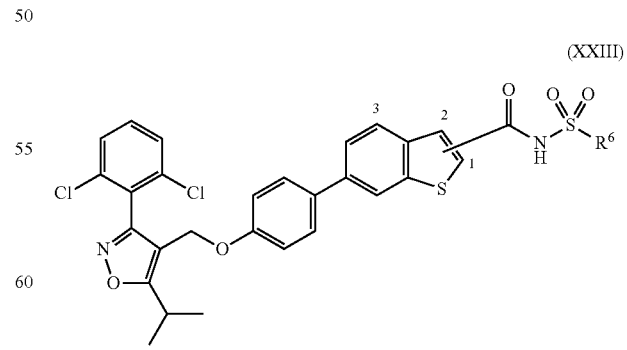
(XXIII)
and pharmaceutically acceptable salts thereof, wherein R⁶ and the substitution position of the —C(O)NHS(O)₂R⁶ group are delineated for each compound in Table 14,

TABLE 14

| Compound | R⁶ | Position |
|---|---|---|
| 718 | —NH₂ | 1 |
| 719 | —NHCH₃ | 1 |
| 720 | —N(CH₃)₂ | 1 |
| 721 | pyrrolidinyl | 1 |
| 722 | piperidinyl | 1 |
| 723 | morpholinyl | 1 |
| 724 | —NH₂ | 2 |
| 725 | —NHCH₃ | 2 |
| 726 | —N(CH₃)₂ | 2 |
| 727 | pyrrolidinyl | 2 |
| 728 | piperidinyl | 2 |
| 729 | morpholinyl | 2 |
| 730 | —NH₂ | 3 |
| 731 | —NHCH₃ | 3 |
| 732 | —N(CH₃)₂ | 3 |
| 733 | pyrrolidinyl | 3 |
| 734 | piperidinyl | 3 |
| 735 | morpholinyl | 3. |

13. The compound of claim 1, which is selected from
(a) compounds of Formula (XXIV),

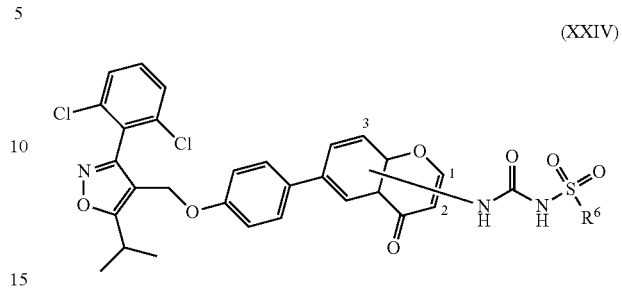

(XXIV)

and pharmaceutically acceptable salts thereof, wherein R⁶ and the substitution position of the —NHC(O)NHS(O)₂R⁶ group are delineated for each compound in Table 15,

TABLE 15

| Compound | R⁶ | Position |
|---|---|---|
| 736 | Methyl | 1 |
| 737 | Ethyl | 1 |
| 738 | Isopropyl | 1 |
| 739 | Butyl | 1 |
| 740 | t-Butyl | 1 |
| 741 | Propyl | 1 |
| 742 | Benzyl | 1 |
| 743 | Vinyl | 1 |
| 744 | Allyl | 1 |
| 745 | —CF₃ | 1 |
| 746 | cyclopropyl | 1 |
| 747 | methylcyclopropyl | 1 |
| 748 | cyclopropylmethyl | 1 |
| 749 | cyclopentyl | 1 |
| 750 | cyclohexyl | 1 |
| 751 | phenyl | 1 |
| 752 | methylphenyl | 1 |

TABLE 15-continued

| Compound | R⁶ | Position |
|---|---|---|
| 753 | 4-methylphenyl | 1 |
| 754 | 4-(OCF₃)phenyl | 1 |
| 755 | 4-tert-butylphenyl | 1 |
| 756 | 2-(OCF₃)phenyl | 1 |
| 757 | 2-fluorophenyl | 1 |
| 758 | naphthalen-2-yl | 1 |
| 759 | —NH₂ | 1 |
| 760 | —NHCH₃ | 1 |
| 761 | —N(CH₃)₂ | 1 |
| 762 | pyrrolidin-1-yl | 1 |
| 763 | piperidin-1-yl | 1 |
| 764 | morpholin-4-yl | 1 |
| 765 | Methyl | 2 |
| 766 | Ethyl | 2 |
| 767 | Isopropyl | 2 |
| 768 | Butyl | 2 |
| 769 | t-Butyl | 2 |
| 770 | Propyl | 2 |
| 771 | Benzyl | 2 |
| 772 | Vinyl | 2 |
| 773 | Allyl | 2 |
| 774 | —CF₃ | 2 |
| 775 | cyclopropyl | 2 |
| 776 | cyclopropyl (other attachment) | 2 |
| 777 | cyclopropylmethyl | 2 |
| 778 | cyclopentyl | 2 |
| 779 | cyclohexyl | 2 |
| 780 | phenyl | 2 |
| 781 | 2-methylphenyl | 2 |
| 782 | 4-methylphenyl | 2 |
| 783 | 4-(OCF₃)phenyl | 2 |
| 784 | 4-tert-butylphenyl | 2 |
| 785 | 2-(OCF₃)phenyl | 2 |
| 786 | 2-fluorophenyl | 2 |
| 787 | naphthalen-2-yl | 2 |
| 788 | —NH₂ | 2 |
| 789 | —NHCH₃ | 2 |
| 790 | —N(CH₃)₂ | 2 |

TABLE 15-continued
| Compound | R⁶ | Position |
|---|---|---|
| 791 | 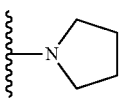 | 2 |
| 792 | 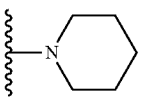 [SMILES: *N1CCCCC1] | 2 |
| 793 | 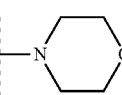 | 2 |
| 794 | Methyl | 3 |
| 795 | Ethyl | 3 |
| 796 | Isopropyl | 3 |
| 797 | Butyl | 3 |
| 798 | t-Butyl | 3 |
| 799 | Propyl | 3 |
| 800 | Benzyl | 3 |
| 801 | Vinyl | 3 |
| 802 | Allyl | 3 |
| 803 | —CF₃ | 3 |
| 804 | 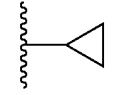 [SMILES: *C1CC1] | 3 |
| 805 | 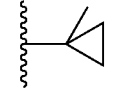 [SMILES: *C1(C)CC1] | 3 |
| 806 | 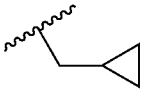 [SMILES: *CC1CC1] | 3 |
| 807 | 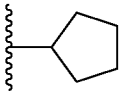 [SMILES: *C1CCCC1] | 3 |
| 808 | 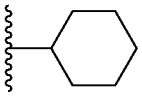 | 3 |
| 809 | 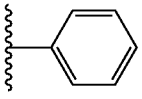 | 3 |
| 810 | 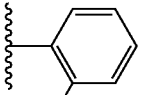 | 3 |
| 811 | 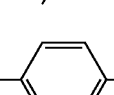 | 3 |
| 812 | 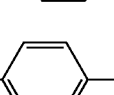 | 3 |
| 813 | 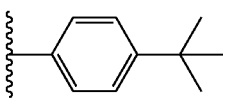 [SMILES: *c1ccc(C(C)(C)C)cc1] | 3 |
| 814 | 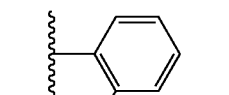 | 3 |
| 815 | 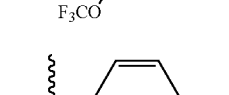 | 3 |
| 816 | 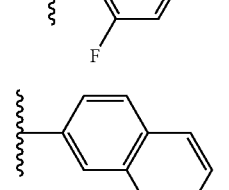 | 3 |
| 817 | —NH₂ | 3 |
| 818 | —NHCH₃ | 3 |
| 819 | —N(CH₃)₂ | 3 |
| 820 | 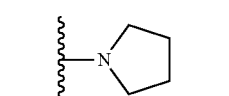 | 3 |
| 821 | 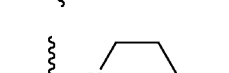 | 3 |
| 822 | 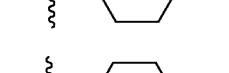 | 3 |
and
(b) compounds of Formula (XXV),
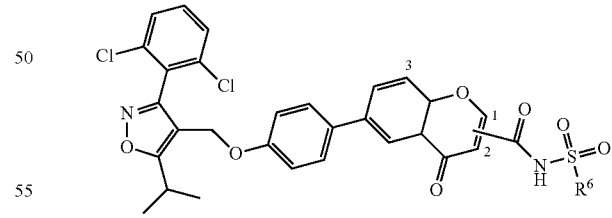
(XXV)
and pharmaceutically acceptable salt thereof wherein R⁶ and the substitution position of the —C(O)NHS(O)₂R⁶ group are delineated for each compound in Table 16,
TABLE 16
| Compound | R⁶ | Position |
|---|---|---|
| 823 | —NH2 | 1 |
| 824 | —NHCH3 | 1 |

TABLE 16-continued

| Compound | R⁶ | Position |
|---|---|---|
| 825 | —N(CH3)2 | 1 |
| 826 | pyrrolidinyl | 1 |
| 827 | piperidinyl | 1 |
| 828 | morpholinyl | 1 |
| 829 | —NH2 | 2 |
| 830 | —NHCH3 | 2 |
| 831 | —N(CH3)2 | 2 |
| 832 | pyrrolidinyl | 2 |
| 833 | piperidinyl | 2 |
| 834 | morpholinyl | 2 |
| 835 | —NH2 | 3 |
| 836 | —NHCH3 | 3 |
| 837 | —N(CH3)2 | 3 |
| 838 | pyrrolidinyl | 3 |
| 839 | piperidinyl | 3 |
| 840 | morpholinyl | 3. |

14. The compound of claim 1, which is selected from (a) compounds of Formula (XXVI),

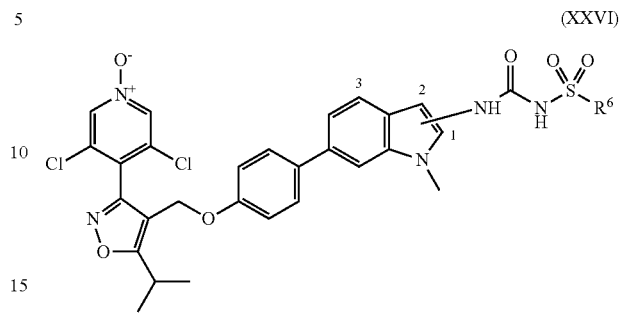

(XXVI)

and pharmaceutically acceptable salts thereof, wherein R⁶ and the substitution position of the —NHC(O)NHS(O)₂R⁶ group are delineated for each compound in Table 17,

TABLE 17

| Compound | R⁶ | Position |
|---|---|---|
| 841 | Methyl | 1 |
| 842 | Ethyl | 1 |
| 843 | Isopropyl | 1 |
| 844 | Butyl | 1 |
| 845 | t-Butyl | 1 |
| 846 | Propyl | 1 |
| 847 | Benzyl | 1 |
| 848 | Vinyl | 1 |
| 849 | Allyl | 1 |
| 850 | —CF3 | 1 |
| 851 | cyclopropyl | 1 |
| 852 | methylcyclopropyl | 1 |
| 853 | cyclopropylmethyl | 1 |
| 854 | cyclopentyl | 1 |
| 855 | cyclohexyl | 1 |
| 856 | phenyl | 1 |
| 857 | methylphenyl | 1 |

TABLE 17-continued

| Compound | R⁶ | Position |
|---|---|---|
| 858 | 4-methylphenyl | 1 |
| 859 | 4-(OCF₃)phenyl | 1 |
| 860 | 4-t-butylphenyl | 1 |
| 861 | 2-(OCF₃)phenyl | 1 |
| 862 | 2-fluorophenyl | 1 |
| 863 | 2-naphthyl | 1 |
| 864 | —NH2 | 1 |
| 865 | —NHCH3 | 1 |
| 866 | —N(CH3)2 | 1 |
| 867 | pyrrolidin-1-yl | 1 |
| 868 | piperidin-1-yl | 1 |
| 869 | morpholin-4-yl | 1 |
| 870 | Methyl | 2 |
| 871 | Ethyl | 2 |
| 872 | Isopropyl | 2 |
| 873 | Butyl | 2 |
| 874 | t-Butyl | 2 |
| 875 | Propyl | 2 |
| 876 | Benzyl | 2 |
| 877 | Vinyl | 2 |
| 878 | Allyl | 2 |
| 879 | —CF3 | 2 |
| 880 | cyclopropyl | 2 |
| 881 | cyclopropyl | 2 |
| 882 | cyclopropylmethyl | 2 |
| 883 | cyclopentyl | 2 |
| 884 | cyclohexyl | 2 |
| 885 | phenyl | 2 |
| 886 | 2-methylphenyl | 2 |
| 887 | 4-methylphenyl | 2 |
| 888 | 4-(OCF₃)phenyl | 2 |
| 889 | 4-t-butylphenyl | 2 |
| 890 | 2-(OCF₃)phenyl | 2 |
| 891 | 2-fluorophenyl | 2 |
| 892 | 2-naphthyl | 2 |
| 893 | —NH2 | 2 |
| 894 | —NHCH3 | 2 |
| 895 | —N(CH3)2 | 2 |

TABLE 17-continued

| Compound | R⁶ | Position |
|---|---|---|
| 896 | 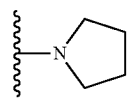 [SMILES: *N1CCCC1] pyrrolidine (N-linked) | 2 |
| 897 | 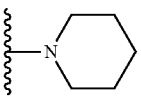 piperidine (N-linked) | 2 |
| 898 | 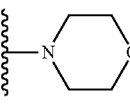 morpholine (N-linked) | 2 |
| 899 | Methyl | 3 |
| 900 | Ethyl | 3 |
| 901 | Isopropyl | 3 |
| 902 | Butyl | 3 |
| 903 | t-Butyl | 3 |
| 904 | Propyl | 3 |
| 905 | Benzyl | 3 |
| 906 | Vinyl | 3 |
| 907 | Allyl | 3 |
| 908 | —CF3 | 3 |
| 909 | 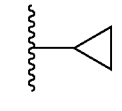 [SMILES: *C1CC1] cyclopropyl | 3 |
| 910 | 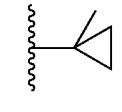 [SMILES: *C1(C)CC1] 1-methylcyclopropyl | 3 |
| 911 | 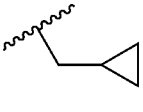 [SMILES: *CC1CC1] cyclopropylmethyl | 3 |
| 912 | 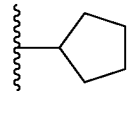 [SMILES: *C1CCCC1] cyclopentyl | 3 |
| 913 | 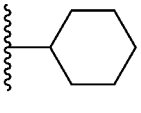 cyclohexyl | 3 |
| 914 | 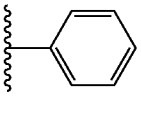 phenyl | 3 |
| 915 | 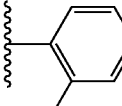 2-methylphenyl | 3 |
| 916 | 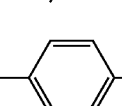 4-methylphenyl | 3 |
| 917 | 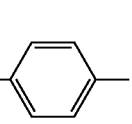 4-(trifluoromethoxy)phenyl | 3 |

TABLE 17-continued

| Compound | R⁶ | Position |
|---|---|---|
| 918 | 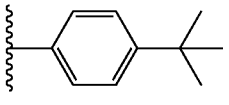 4-tert-butylphenyl | 3 |
| 919 | 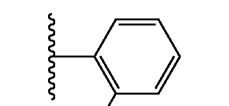 2-(trifluoromethoxy)phenyl | 3 |
| 920 | 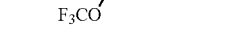 2-fluorophenyl | 3 |
| 921 | naphthyl | 3 |
| 922 | —NH2 | 3 |
| 923 | —NHCH3 | 3 |
| 924 | —N(CH3)2 | 3 |
| 925 | pyrrolidine (N-linked) | 3 |
| 926 | piperidine (N-linked) | 3 |
| 927 | morpholine (N-linked) | 3 | and
(b) compounds of Formula (XXVII),

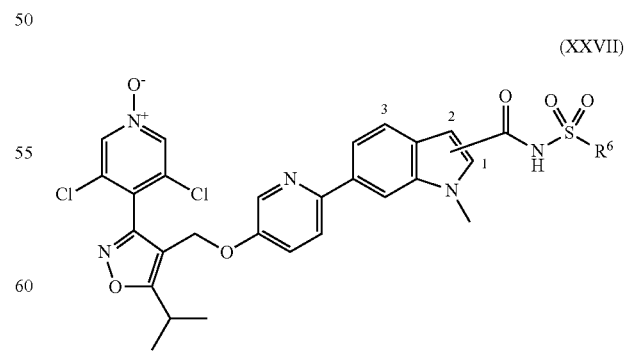

(XXVII)

and pharmaceutically acceptable salts thereof, wherein R⁶ and the substitution position of the —C(O)NHS(O)₂R⁶ group are delineated for each compound in Table 18,

TABLE 18

| Compound | R⁶ | Position |
|---|---|---|
| 928 | —NH₂ | 1 |
| 929 | —NHCH₃ | 1 |
| 930 | —N(CH₃)₂ | 1 |
| 931 | pyrrolidin-1-yl | 1 |
| 932 | piperidin-1-yl | 1 |
| 933 | morpholin-4-yl | 1 |
| 934 | —NH₂ | 2 |
| 935 | —NHCH₃ | 2 |
| 936 | —N(CH₃)₂ | 2 |
| 937 | pyrrolidin-1-yl | 2 |
| 938 | piperidin-1-yl | 2 |
| 939 | morpholin-4-yl | 2 |
| 940 | —NH₂ | 3 |
| 941 | —NHCH₃ | 3 |
| 942 | —N(CH₃)₂ | 3 |
| 943 | pyrrolidin-1-yl | 3 |
| 944 | piperidin-1-yl | 3 |
| 945 | morpholin-4-yl | 3 |

15. A method for treating disease or condition selected from primary biliary cirrhosis, cerebrotendinous xanthomatosis, primary sclerosing cholangitis, alcoholic liver disease, nonalcoholic fatty liver disease, nonalcoholic steatohepatitis, atherosclerosis, arteriosclerosis, dyslipidemia, hypercholesterolemia, hypertriglyceridemia, insulin resistance, Type I and Type II diabetes and obesity in a subject in need thereof, comprising administering to the subject a therapeutically effective amount of a compound according to claim 1.

16. The method according to claim 15, wherein the disease or condition is selected from primary biliary cirrhosis and primary sclerosing cholangitis.

17. The method according to claim 15, wherein the disease or condition is selected from the group consisting of atherosclerosis, hypercholesterolemia, and hypertriglyceridemia.

18. The method according to claim 15, wherein the disease or condition is selected from the group consisting of Type I diabetes, Type II diabetes, and obesity.

19. A pharmaceutical composition comprising a compound according to claim 1 and a pharmaceutically acceptable carrier.

20. The method according to claim 15, wherein the disease or condition is primary biliary cirrhosis.

21. The method according to claim 15, wherein the disease or condition is nonalcoholic steatohepatitis.

22. The method according to claim 15, wherein the disease or condition is nonalcoholic fatty liver disease.

* * * * *

UNITED STATES PATENT AND TRADEMARK OFFICE
CERTIFICATE OF CORRECTION

PATENT NO. : 10,080,743 B2
APPLICATION NO. : 15/497359
DATED : September 25, 2018
INVENTOR(S) : Yat Sun Or et al.

Page 1 of 1

It is certified that error appears in the above-identified patent and that said Letters Patent is hereby corrected as shown below:

In the Claims

Column 82, Claim 1, Line 40: please replace Formula I " 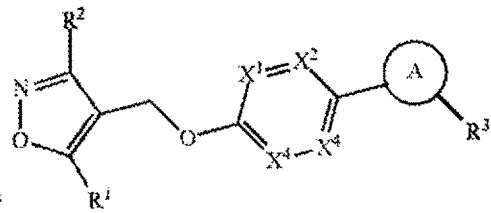 "

with -- 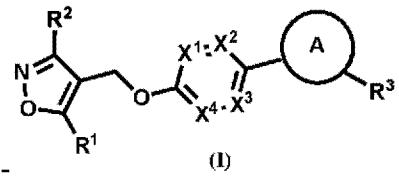 (I) --;

Column 89, Claim 6, compound 50: please replace " 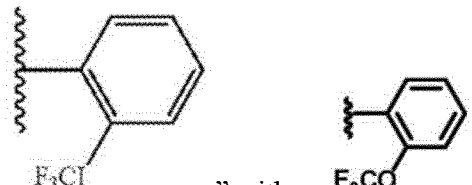 " with -- 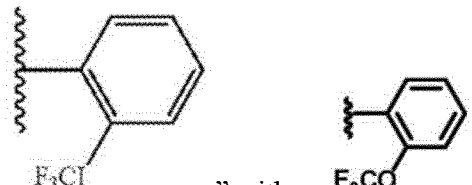 --; and Column 90, Claim 6, compound 79: please replace " 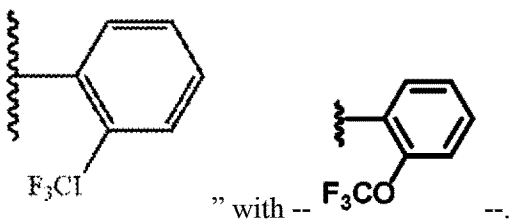 " with -- 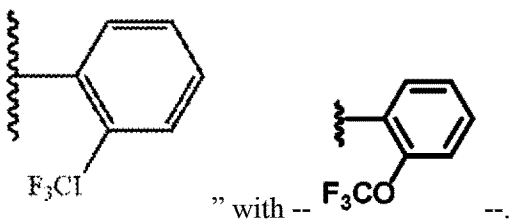 --.

Signed and Sealed this
Twenty-fifth Day of December, 2018

Andrei Iancu
*Director of the United States Patent and Trademark Office*